United States Patent [19]
Clardy et al.

[11] Patent Number: 5,939,528
[45] Date of Patent: Aug. 17, 1999

[54] CRYSTALLINE FRAP COMPLEX

[75] Inventors: Jon C. Clardy, Ithaca, N.Y.; Jungwon Choi, Seoul, Rep. of Korea

[73] Assignee: Cornell Research Foundation, Inc., Ithaca, N.Y.

[21] Appl. No.: 08/963,601

[22] Filed: Oct. 31, 1997

Related U.S. Application Data

[62] Division of application No. 08/735,848, Oct. 23, 1996.
[51] Int. Cl.$^6$ .................................................. C07K 14/47
[52] U.S. Cl. ........................ 530/350; 536/23.1; 536/23.5
[58] Field of Search ........................ 530/350; 536/23.1, 536/23.5

[56] References Cited

PUBLICATIONS

Choi et al. "Structure of the FKBP12–Rapamycin complex interacting with the binding domain of human FRAP" Science 273, 239–242, Jul. 12, 1996.

Van Duyne "Atomic structure of the human immunophilin FKBP–12 complex with FK506 and rapamycin" J. Mol. Biol. 229, 105–124, 1993.

Wilson et al. Comparative X–ray structure of the major binding protein for the immunosuppressant FK506 . . . Acta Cryst. D51, 551–521, 1995.

*Primary Examiner*—Robert A. Wax
*Assistant Examiner*—Nashaat T. Nashed
*Attorney, Agent, or Firm*—David L. Berstein

[57] ABSTRACT

The invention relates to the human protein FRAP, and in particular to the FKBP12-rapamycin binding domain thereof and to the ternary complex formed by the FRB domain, rapamycin and FKBP12. A new crystalline composition comprising the ternary complex, coordinates defining its three dimensional structure in atomic detail, and uses thereof are disclosed.

3 Claims, 39 Drawing Sheets

Fig 4-1

| ATOM | 1 | N | GLY | A | 1 | 5.987 | 28.058 | 50.014 | 1.00 | 24.95 | N |
|---|---|---|---|---|---|---|---|---|---|---|---|
| ATOM | 2 | CA | GLY | A | 1 | 5.986 | 26.568 | 49.849 | 1.00 | 14.30 | C |
| ATOM | 3 | C | GLY | A | 1 | 4.588 | 25.968 | 49.843 | 1.00 | 12.34 | C |
| ATOM | 4 | O | GLY | A | 1 | 3.587 | 26.690 | 49.931 | 1.00 | 3.24 | O |
| ATOM | 5 | 1H | GLY | A | 1 | 5.460 | 28.281 | 50.881 | 0.00 | 0.00 | H |
| ATOM | 6 | 2H | GLY | A | 1 | 6.961 | 28.429 | 50.048 | 0.00 | 0.00 | H |
| ATOM | 7 | 3H | GLY | A | 1 | 5.463 | 28.482 | 49.221 | 0.00 | 0.00 | H |
| ATOM | 8 | N | VAL | A | 2 | 4.539 | 24.648 | 49.684 | 1.00 | 9.85 | N |
| ATOM | 9 | CA | VAL | A | 2 | 3.311 | 23.862 | 49.748 | 1.00 | 11.89 | C |
| ATOM | 10 | C | VAL | A | 2 | 3.549 | 22.668 | 50.692 | 1.00 | 15.67 | C |
| ATOM | 11 | O | VAL | A | 2 | 4.576 | 21.989 | 50.605 | 1.00 | 16.61 | O |
| ATOM | 12 | CB | VAL | A | 2 | 2.889 | 23.360 | 48.318 | 1.00 | 9.17 | C |
| ATOM | 13 | CG1 | VAL | A | 2 | 4.114 | 23.006 | 47.492 | 1.00 | 14.93 | C |
| ATOM | 14 | CG2 | VAL | A | 2 | 1.975 | 22.155 | 48.411 | 1.00 | 2.00 | C |
| ATOM | 15 | H | VAL | A | 2 | 5.366 | 24.143 | 49.539 | 0.00 | 0.00 | H |
| ATOM | 16 | N | GLN | A | 3 | 2.643 | 22.482 | 51.646 | 1.00 | 17.91 | N |
| ATOM | 17 | CA | GLN | A | 3 | 2.789 | 21.445 | 52.664 | 1.00 | 20.42 | C |
| ATOM | 18 | C | GLN | A | 3 | 1.817 | 20.280 | 52.454 | 1.00 | 17.06 | C |
| ATOM | 19 | O | GLN | A | 3 | 0.608 | 20.466 | 52.367 | 1.00 | 17.79 | O |
| ATOM | 20 | CB | GLN | A | 3 | 2.600 | 22.065 | 54.056 | 1.00 | 26.51 | C |
| ATOM | 21 | CG | GLN | A | 3 | 2.416 | 21.064 | 55.181 | 1.00 | 34.77 | C |
| ATOM | 22 | CD | GLN | A | 3 | 3.718 | 20.451 | 55.660 | 1.00 | 41.28 | C |
| ATOM | 23 | OE1 | GLN | A | 3 | 4.754 | 20.581 | 55.015 | 1.00 | 44.41 | O |
| ATOM | 24 | NE2 | GLN | A | 3 | 3.665 | 19.760 | 56.792 | 1.00 | 42.31 | N |
| ATOM | 25 | H | GLN | A | 3 | 1.852 | 23.045 | 51.649 | 0.00 | 0.00 | H |
| ATOM | 26 | 1HE2 | GLN | A | 3 | 4.510 | 19.373 | 57.085 | 0.00 | 0.00 | H |
| ATOM | 27 | 2HE2 | GLN | A | 3 | 2.812 | 19.651 | 57.241 | 0.00 | 0.00 | H |
| ATOM | 28 | N | VAL | A | 4 | 2.363 | 19.082 | 52.313 | 1.00 | 14.50 | N |
| ATOM | 29 | CA | VAL | A | 4 | 1.540 | 17.890 | 52.127 | 1.00 | 13.12 | C |
| ATOM | 30 | C | VAL | A | 4 | 1.544 | 17.037 | 53.401 | 1.00 | 12.15 | C |
| ATOM | 31 | O | VAL | A | 4 | 2.600 | 16.705 | 53.947 | 1.00 | 15.65 | O |
| ATOM | 32 | CB | VAL | A | 4 | 2.054 | 17.030 | 50.930 | 1.00 | 10.68 | C |
| ATOM | 33 | CG1 | VAL | A | 4 | 0.924 | 16.172 | 50.364 | 1.00 | 7.51 | C |
| ATOM | 34 | CG2 | VAL | A | 4 | 2.630 | 17.930 | 49.842 | 1.00 | 9.85 | C |
| ATOM | 35 | H | VAL | A | 4 | 3.336 | 19.008 | 52.381 | 0.00 | 0.00 | H |
| ATOM | 36 | N | GLU | A | 5 | 0.363 | 16.733 | 53.914 | 1.00 | 6.97 | N |
| ATOM | 37 | CA | GLU | A | 5 | 0.275 | 15.856 | 55.071 | 1.00 | 5.19 | C |
| ATOM | 38 | C | GLU | A | 5 | -0.743 | 14.752 | 54.848 | 1.00 | 3.46 | C |
| ATOM | 39 | O | GLU | A | 5 | -1.937 | 15.023 | 54.745 | 1.00 | 4.04 | O |
| ATOM | 40 | CB | GLU | A | 5 | -0.096 | 16.664 | 56.308 | 1.00 | 8.81 | C |
| ATOM | 41 | CG | GLU | A | 5 | 0.621 | 17.998 | 56.389 | 1.00 | 13.30 | C |
| ATOM | 42 | CD | GLU | A | 5 | 0.346 | 18.726 | 57.674 | 1.00 | 15.76 | C |
| ATOM | 43 | OE1 | GLU | A | 5 | -0.710 | 19.385 | 57.778 | 1.00 | 22.20 | O |
| ATOM | 44 | OE2 | GLU | A | 5 | 1.188 | 18.629 | 58.586 | 1.00 | 22.97 | O |
| ATOM | 45 | H | GLU | A | 5 | -0.430 | 17.182 | 53.551 | 0.00 | 0.00 | H |
| ATOM | 46 | N | THR | A | 6 | -0.271 | 13.511 | 54.805 | 1.00 | 2.00 | N |
| ATOM | 47 | CA | THR | A | 6 | -1.125 | 12.365 | 54.508 | 1.00 | 5.26 | C |
| ATOM | 48 | C | THR | A | 6 | -2.355 | 12.240 | 55.415 | 1.00 | 9.57 | C |
| ATOM | 49 | O | THR | A | 6 | -2.281 | 12.454 | 56.629 | 1.00 | 15.36 | O |
| ATOM | 50 | CB | THR | A | 6 | -0.337 | 11.045 | 54.575 | 1.00 | 3.67 | C |
| ATOM | 51 | OG1 | THR | A | 6 | 0.881 | 11.178 | 53.836 | 1.00 | 13.50 | O |
| ATOM | 52 | CG2 | THR | A | 6 | -1.132 | 9.919 | 53.972 | 1.00 | 2.01 | C |
| ATOM | 53 | H | THR | A | 6 | 0.666 | 13.372 | 55.050 | 0.00 | 0.00 | H |
| ATOM | 54 | HG1 | THR | A | 6 | 1.493 | 10.508 | 54.158 | 0.00 | 0.00 | H |
| ATOM | 55 | N | ILE | A | 7 | -3.509 | 12.099 | 54.772 | 1.00 | 8.03 | N |
| ATOM | 56 | CA | ILE | A | 7 | -4.755 | 11.709 | 55.423 | 1.00 | 7.62 | C |
| ATOM | 57 | C | ILE | A | 7 | -4.979 | 10.199 | 55.249 | 1.00 | 11.96 | C |
| ATOM | 58 | O | ILE | A | 7 | -5.686 | 9.576 | 56.034 | 1.00 | 17.57 | O |

Fig 4-2

| | | | | | | | | | | |
|---|---|---|---|---|---|---|---|---|---|---|
| ATOM | 59 | CB | ILE | A | 7 | -5.965 | 12.465 | 54.799 | 1.00 5.96 | C |
| ATOM | 60 | CG1 | ILE | A | 7 | -5.918 | 13.947 | 55.170 | 1.00 2.00 | C |
| ATOM | 61 | CG2 | ILE | A | 7 | -7.275 | 11.841 | 55.244 | 1.00 2.71 | C |
| ATOM | 62 | CD1 | ILE | A | 7 | -7.008 | 14.764 | 54.527 | 1.00 2.01 | C |
| ATOM | 63 | H | ILE | A | 7 | -3.506 | 12.334 | 53.824 | 0.00 0.00 | H |
| ATOM | 64 | N | SER | A | 8 | -4.469 | 9.648 | 54.151 | 1.00 12.78 | N |
| ATOM | 65 | CA | SER | A | 8 | -4.629 | 8.226 | 53.842 | 1.00 12.24 | C |
| ATOM | 66 | C | SER | A | 8 | -3.685 | 7.798 | 52.707 | 1.00 19.11 | C |
| ATOM | 67 | O | SER | A | 8 | -3.607 | 8.454 | 51.664 | 1.00 17.14 | O |
| ATOM | 68 | CB | SER | A | 8 | -6.079 | 7.930 | 53.450 | 1.00 6.63 | C |
| ATOM | 69 | OG | SER | A | 8 | -6.236 | 6.581 | 53.064 | 1.00 12.33 | O |
| ATOM | 70 | H | SER | A | 8 | -4.039 | 10.240 | 53.499 | 0.00 0.00 | H |
| ATOM | 71 | HG | SER | A | 8 | -7.179 | 6.384 | 53.022 | 0.00 0.00 | H |
| ATOM | 72 | N | PRO | A | 9 | -2.830 | 6.798 | 52.965 | 1.00 23.27 | N |
| ATOM | 73 | CA | PRO | A | 9 | -1.706 | 6.548 | 52.055 | 1.00 25.68 | C |
| ATOM | 74 | C | PRO | A | 9 | -2.056 | 5.766 | 50.778 | 1.00 28.63 | C |
| ATOM | 75 | O | PRO | A | 9 | -3.034 | 5.014 | 50.737 | 1.00 30.17 | O |
| ATOM | 76 | CB | PRO | A | 9 | -0.709 | 5.793 | 52.932 | 1.00 25.08 | C |
| ATOM | 77 | CG | PRO | A | 9 | -1.572 | 5.093 | 53.920 | 1.00 26.18 | C |
| ATOM | 78 | CD | PRO | A | 9 | -2.665 | 6.076 | 54.238 | 1.00 22.82 | C |
| ATOM | 79 | N | GLY | A | 10 | -1.272 | 5.988 | 49.728 | 1.00 28.78 | N |
| ATOM | 80 | CA | GLY | A | 10 | -1.373 | 5.168 | 48.531 | 1.00 32.81 | C |
| ATOM | 81 | C | GLY | A | 10 | -0.241 | 4.154 | 48.412 | 1.00 34.72 | C |
| ATOM | 82 | O | GLY | A | 10 | 0.479 | 3.916 | 49.386 | 1.00 37.49 | O |
| ATOM | 83 | H | GLY | A | 10 | -0.602 | 6.696 | 49.796 | 0.00 0.00 | H |
| ATOM | 84 | N | ASP | A | 11 | -0.018 | 3.626 | 47.208 | 1.00 30.71 | N |
| ATOM | 85 | CA | ASP | A | 11 | 0.992 | 2.585 | 47.006 | 1.00 28.23 | C |
| ATOM | 86 | C | ASP | A | 11 | 2.438 | 3.073 | 47.085 | 1.00 29.86 | C |
| ATOM | 87 | O | ASP | A | 11 | 3.364 | 2.273 | 47.190 | 1.00 31.65 | O |
| ATOM | 88 | CB | ASP | A | 11 | 0.767 | 1.862 | 45.675 | 1.00 23.26 | C |
| ATOM | 89 | CG | ASP | A | 11 | 0.713 | 2.804 | 44.493 | 1.00 21.83 | C |
| ATOM | 90 | OD1 | ASP | A | 11 | 1.591 | 3.686 | 44.377 | 1.00 13.66 | O |
| ATOM | 91 | OD2 | ASP | A | 11 | -0.204 | 2.635 | 43.659 | 1.00 23.38 | O |
| ATOM | 92 | H | ASP | A | 11 | -0.664 | 3.846 | 46.504 | 0.00 0.00 | H |
| ATOM | 93 | N | GLY | A | 12 | 2.637 | 4.372 | 46.898 | 1.00 31.53 | N |
| ATOM | 94 | CA | GLY | A | 12 | 3.958 | 4.948 | 47.081 | 1.00 34.79 | C |
| ATOM | 95 | C | GLY | A | 12 | 4.976 | 4.585 | 46.015 | 1.00 37.89 | C |
| ATOM | 96 | O | GLY | A | 12 | 6.183 | 4.621 | 46.262 | 1.00 38.20 | O |
| ATOM | 97 | H | GLY | A | 12 | 1.858 | 4.932 | 46.696 | 0.00 0.00 | H |
| ATOM | 98 | N | ARG | A | 13 | 4.488 | 4.222 | 44.833 | 1.00 40.35 | N |
| ATOM | 99 | CA | ARG | A | 13 | 5.357 | 4.030 | 43.667 | 1.00 43.98 | C |
| ATOM | 100 | C | ARG | A | 13 | 4.720 | 4.537 | 42.369 | 1.00 40.88 | C |
| ATOM | 101 | O | ARG | A | 13 | 5.414 | 4.995 | 41.459 | 1.00 41.05 | O |
| ATOM | 102 | CB | ARG | A | 13 | 5.756 | 2.552 | 43.526 | 1.00 48.12 | C |
| ATOM | 103 | CG | ARG | A | 13 | 4.624 | 1.555 | 43.724 | 1.00 56.08 | C |
| ATOM | 104 | CD | ARG | A | 13 | 5.130 | 0.296 | 44.418 | 1.00 64.50 | C |
| ATOM | 105 | NE | ARG | A | 13 | 4.963 | 0.361 | 45.870 | 1.00 70.55 | N |
| ATOM | 106 | CZ | ARG | A | 13 | 4.154 | -0.435 | 46.567 | 1.00 73.54 | C |
| ATOM | 107 | NH1 | ARG | A | 13 | 3.490 | -1.415 | 45.961 | 1.00 75.14 | N |
| ATOM | 108 | NH2 | ARG | A | 13 | 4.023 | -0.266 | 47.877 | 1.00 74.82 | N |
| ATOM | 109 | H | ARG | A | 13 | 3.572 | 3.918 | 44.840 | 0.00 0.00 | H |
| ATOM | 110 | HE | ARG | A | 13 | 5.508 | 1.005 | 46.370 | 0.00 0.00 | H |
| ATOM | 111 | 1HH1 | ARG | A | 13 | 3.595 | -1.557 | 44.977 | 0.00 0.00 | H |
| ATOM | 112 | 2HH1 | ARG | A | 13 | 2.873 | -2.001 | 46.485 | 0.00 0.00 | H |
| ATOM | 113 | 1HH2 | ARG | A | 13 | 4.540 | 0.450 | 48.341 | 0.00 0.00 | H |
| ATOM | 114 | 2HH2 | ARG | A | 13 | 3.414 | -0.864 | 48.399 | 0.00 0.00 | H |
| ATOM | 115 | N | THR | A | 14 | 3.392 | 4.531 | 42.328 | 1.00 36.51 | N |
| ATOM | 116 | CA | THR | A | 14 | 2.654 | 5.085 | 41.199 | 1.00 31.82 | C |
| ATOM | 117 | C | THR | A | 14 | 2.416 | 6.589 | 41.356 | 1.00 28.19 | C |
| ATOM | 118 | O | THR | A | 14 | 1.373 | 7.023 | 41.846 | 1.00 25.30 | O |

Fig 4-3

| ATOM | 119 | CB | THR A | 14 | 1.296 | 4.362 | 41.010 | 1.00 | 34.22 | C |
|------|-----|-----|-----|-----|-------|-------|--------|------|-------|---|
| ATOM | 120 | OG1 | THR A | 14 | 1.477 | 2.945 | 41.172 | 1.00 | 31.38 | O |
| ATOM | 121 | CG2 | THR A | 14 | 0.722 | 4.651 | 39.621 | 1.00 | 29.70 | C |
| ATOM | 122 | H | THR A | 14 | 2.944 | 3.906 | 42.915 | 0.00 | 0.00 | H |
| ATOM | 123 | HG1 | THR A | 14 | 0.659 | 2.484 | 40.952 | 0.00 | 0.00 | H |
| ATOM | 124 | N | PHE A | 15 | 3.430 | 7.364 | 41.000 | 1.00 | 27.12 | N |
| ATOM | 125 | CA | PHE A | 15 | 3.354 | 8.822 | 40.970 | 1.00 | 30.73 | C |
| ATOM | 126 | C | PHE A | 15 | 2.902 | 9.358 | 39.596 | 1.00 | 34.59 | C |
| ATOM | 127 | O | PHE A | 15 | 3.176 | 8.739 | 38.557 | 1.00 | 32.29 | O |
| ATOM | 128 | CB | PHE A | 15 | 4.725 | 9.405 | 41.330 | 1.00 | 30.56 | C |
| ATOM | 129 | CG | PHE A | 15 | 5.202 | 9.018 | 42.701 | 1.00 | 31.81 | C |
| ATOM | 130 | CD1 | PHE A | 15 | 5.732 | 7.756 | 42.936 | 1.00 | 31.84 | C |
| ATOM | 131 | CD2 | PHE A | 15 | 5.046 | 9.885 | 43.775 | 1.00 | 31.26 | C |
| ATOM | 132 | CE1 | PHE A | 15 | 6.089 | 7.363 | 44.218 | 1.00 | 31.05 | C |
| ATOM | 133 | CE2 | PHE A | 15 | 5.400 | 9.499 | 45.062 | 1.00 | 28.40 | C |
| ATOM | 134 | CZ | PHE A | 15 | 5.919 | 8.237 | 45.283 | 1.00 | 31.16 | C |
| ATOM | 135 | H | PHE A | 15 | 4.257 | 6.922 | 40.707 | 0.00 | 0.00 | H |
| ATOM | 136 | N | PRO A | 16 | 2.232 | 10.532 | 39.571 | 1.00 | 35.21 | N |
| ATOM | 137 | CA | PRO A | 16 | 1.814 | 11.122 | 38.296 | 1.00 | 36.14 | C |
| ATOM | 138 | C | PRO A | 16 | 2.998 | 11.672 | 37.512 | 1.00 | 38.59 | C |
| ATOM | 139 | O | PRO A | 16 | 3.580 | 12.683 | 37.895 | 1.00 | 40.62 | O |
| ATOM | 140 | CB | PRO A | 16 | 0.852 | 12.243 | 38.710 | 1.00 | 33.90 | C |
| ATOM | 141 | CG | PRO A | 16 | 0.905 | 12.310 | 40.215 | 1.00 | 34.16 | C |
| ATOM | 142 | CD | PRO A | 16 | 2.068 | 11.493 | 40.671 | 1.00 | 32.43 | C |
| ATOM | 143 | N | LYS A | 17 | 3.408 | 10.958 | 36.467 | 1.00 | 44.97 | N |
| ATOM | 144 | CA | LYS A | 17 | 4.463 | 11.441 | 35.572 | 1.00 | 49.95 | C |
| ATOM | 145 | C | LYS A | 17 | 4.031 | 12.703 | 34.823 | 1.00 | 50.23 | C |
| ATOM | 146 | O | LYS A | 17 | 2.882 | 12.813 | 34.389 | 1.00 | 51.36 | O |
| ATOM | 147 | CB | LYS A | 17 | 4.856 | 10.356 | 34.563 | 1.00 | 53.22 | C |
| ATOM | 148 | CG | LYS A | 17 | 5.973 | 9.427 | 35.030 | 1.00 | 61.47 | C |
| ATOM | 149 | CD | LYS A | 17 | 5.425 | 8.075 | 35.497 | 1.00 | 69.15 | C |
| ATOM | 150 | CE | LYS A | 17 | 6.545 | 7.050 | 35.721 | 1.00 | 73.13 | C |
| ATOM | 151 | NZ | LYS A | 17 | 6.050 | 5.706 | 36.174 | 1.00 | 72.77 | N |
| ATOM | 152 | H | LYS A | 17 | 3.044 | 10.054 | 36.366 | 0.00 | 0.00 | H |
| ATOM | 153 | 1HZ | LYS A | 17 | 5.395 | 5.316 | 35.466 | 0.00 | 0.00 | H |
| ATOM | 154 | 2HZ | LYS A | 17 | 6.857 | 5.061 | 36.292 | 0.00 | 0.00 | H |
| ATOM | 155 | 3HZ | LYS A | 17 | 5.550 | 5.803 | 37.081 | 0.00 | 0.00 | H |
| ATOM | 156 | N | ARG A | 18 | 4.938 | 13.672 | 34.718 | 1.00 | 48.43 | N |
| ATOM | 157 | CA | ARG A | 18 | 4.666 | 14.908 | 33.986 | 1.00 | 46.13 | C |
| ATOM | 158 | C | ARG A | 18 | 3.965 | 14.637 | 32.652 | 1.00 | 44.43 | C |
| ATOM | 159 | O | ARG A | 18 | 4.440 | 13.832 | 31.844 | 1.00 | 44.85 | O |
| ATOM | 160 | CB | ARG A | 18 | 5.968 | 15.671 | 33.732 | 1.00 | 47.22 | C |
| ATOM | 161 | CG | ARG A | 18 | 5.755 | 17.034 | 33.092 | 1.00 | 53.52 | C |
| ATOM | 162 | CD | ARG A | 18 | 7.030 | 17.572 | 32.467 | 1.00 | 60.93 | C |
| ATOM | 163 | NE | ARG A | 18 | 8.005 | 18.008 | 33.466 | 1.00 | 68.56 | N |
| ATOM | 164 | CZ | ARG A | 18 | 7.995 | 19.201 | 34.054 | 1.00 | 71.82 | C |
| ATOM | 165 | NH1 | ARG A | 18 | 7.000 | 20.052 | 33.826 | 1.00 | 74.07 | N |
| ATOM | 166 | NH2 | ARG A | 18 | 8.954 | 19.528 | 34.910 | 1.00 | 73.41 | N |
| ATOM | 167 | H | ARG A | 18 | 5.782 | 13.553 | 35.190 | 0.00 | 0.00 | H |
| ATOM | 168 | HE | ARG A | 18 | 8.698 | 17.375 | 33.748 | 0.00 | 0.00 | H |
| ATOM | 169 | 1HH1 | ARG A | 18 | 6.256 | 19.798 | 33.207 | 0.00 | 0.00 | H |
| ATOM | 170 | 2HH1 | ARG A | 18 | 6.994 | 20.950 | 34.267 | 0.00 | 0.00 | H |
| ATOM | 171 | 1HH2 | ARG A | 18 | 9.674 | 18.876 | 35.143 | 0.00 | 0.00 | H |
| ATOM | 172 | 2HH2 | ARG A | 18 | 8.923 | 20.425 | 35.358 | 0.00 | 0.00 | H |
| ATOM | 173 | N | GLY A | 19 | 2.775 | 15.209 | 32.491 | 1.00 | 41.63 | N |
| ATOM | 174 | CA | GLY A | 19 | 2.037 | 15.058 | 31.246 | 1.00 | 36.64 | C |
| ATOM | 175 | C | GLY A | 19 | 0.878 | 14.072 | 31.281 | 1.00 | 33.71 | C |
| ATOM | 176 | O | GLY A | 19 | 0.242 | 13.821 | 30.256 | 1.00 | 31.30 | O |
| ATOM | 177 | H | GLY A | 19 | 2.437 | 15.781 | 33.210 | 0.00 | 0.00 | H |
| ATOM | 178 | N | GLN A | 20 | 0.603 | 13.509 | 32.454 | 1.00 | 31.51 | N |

Fig 4-4

```
ATOM    179  CA   GLN A  20      -0.571  12.655  32.647  1.00 27.89           C
ATOM    180  C    GLN A  20      -1.784  13.458  33.096  1.00 26.36           C
ATOM    181  O    GLN A  20      -1.641  14.558  33.652  1.00 23.69           O
ATOM    182  CB   GLN A  20      -0.290  11.586  33.702  1.00 27.47           C
ATOM    183  CG   GLN A  20       0.907  10.723  33.416  1.00 29.05           C
ATOM    184  CD   GLN A  20       0.945   9.516  34.305  1.00 28.73           C
ATOM    185  OE1  GLN A  20       1.852   9.355  35.112  1.00 29.95           O
ATOM    186  NE2  GLN A  20      -0.064   8.672  34.191  1.00 29.76           N
ATOM    187  H    GLN A  20       1.278  13.579  33.162  0.00  0.00           H
ATOM    188  1HE2 GLN A  20      -0.025   7.895  34.776  0.00  0.00           H
ATOM    189  2HE2 GLN A  20      -0.781   8.854  33.542  0.00  0.00           H
ATOM    190  N    THR A  21      -2.957  12.836  32.994  1.00 23.74           N
ATOM    191  CA   THR A  21      -4.185  13.406  33.551  1.00 19.78           C
ATOM    192  C    THR A  21      -4.502  12.869  34.945  1.00 19.51           C
ATOM    193  O    THR A  21      -4.895  11.707  35.112  1.00 21.36           O
ATOM    194  CB   THR A  21      -5.398  13.137  32.648  1.00 18.09           C
ATOM    195  OG1  THR A  21      -5.103  13.576  31.319  1.00 25.65           O
ATOM    196  CG2  THR A  21      -6.624  13.882  33.159  1.00 15.30           C
ATOM    197  H    THR A  21      -2.993  11.964  32.525  0.00  0.00           H
ATOM    198  HG1  THR A  21      -4.667  12.831  30.862  0.00  0.00           H
ATOM    199  N    CYS A  22      -4.390  13.744  35.939  1.00 15.33           N
ATOM    200  CA   CYS A  22      -4.794  13.421  37.302  1.00  7.92           C
ATOM    201  C    CYS A  22      -6.301  13.589  37.492  1.00  7.02           C
ATOM    202  O    CYS A  22      -6.840  14.676  37.284  1.00  8.66           O
ATOM    203  CB   CYS A  22      -4.056  14.322  38.281  1.00  4.88           C
ATOM    204  SG   CYS A  22      -2.300  14.464  37.959  1.00  9.58           S
ATOM    205  H    CYS A  22      -4.044  14.636  35.726  0.00  0.00           H
ATOM    206  N    VAL A  23      -6.991  12.485  37.760  1.00  4.33           N
ATOM    207  CA   VAL A  23      -8.371  12.542  38.232  1.00  6.31           C
ATOM    208  C    VAL A  23      -8.353  12.579  39.770  1.00 11.82           C
ATOM    209  O    VAL A  23      -7.678  11.765  40.416  1.00 17.38           O
ATOM    210  CB   VAL A  23      -9.180  11.314  37.743  1.00  3.87           C
ATOM    211  CG1  VAL A  23     -10.658  11.483  38.043  1.00  2.00           C
ATOM    212  CG2  VAL A  23      -8.972  11.121  36.264  1.00  5.84           C
ATOM    213  H    VAL A  23      -6.547  11.617  37.634  0.00  0.00           H
ATOM    214  N    VAL A  24      -8.946  13.622  40.342  1.00 10.13           N
ATOM    215  CA   VAL A  24      -8.896  13.840  41.782  1.00  5.89           C
ATOM    216  C    VAL A  24     -10.237  14.309  42.333  1.00  7.13           C
ATOM    217  O    VAL A  24     -11.078  14.804  41.583  1.00  8.15           O
ATOM    218  CB   VAL A  24      -7.806  14.883  42.170  1.00  3.59           C
ATOM    219  CG1  VAL A  24      -6.481  14.535  41.524  1.00  2.00           C
ATOM    220  CG2  VAL A  24      -8.238  16.276  41.784  1.00  2.66           C
ATOM    221  H    VAL A  24      -9.395  14.274  39.762  0.00  0.00           H
ATOM    222  N    HIS A  25     -10.481  14.041  43.617  1.00  8.15           N
ATOM    223  CA   HIS A  25     -11.588  14.671  44.346  1.00  5.84           C
ATOM    224  C    HIS A  25     -11.013  15.611  45.409  1.00  5.86           C
ATOM    225  O    HIS A  25     -10.085  15.233  46.125  1.00  8.08           O
ATOM    226  CB   HIS A  25     -12.462  13.611  45.015  1.00  2.00           C
ATOM    227  CG   HIS A  25     -13.789  13.412  44.351  1.00  2.00           C
ATOM    228  ND1  HIS A  25     -14.420  14.398  43.625  1.00  6.75           N
ATOM    229  CD2  HIS A  25     -14.625  12.348  44.335  1.00  2.01           C
ATOM    230  CE1  HIS A  25     -15.591  13.959  43.204  1.00  2.00           C
ATOM    231  NE2  HIS A  25     -15.738  12.715  43.619  1.00  2.00           N
ATOM    232  H    HIS A  25      -9.837  13.454  44.074  0.00  0.00           H
ATOM    233  HD1  HIS A  25     -13.990  15.194  43.216  0.00  0.00           H
ATOM    234  HE2  HIS A  25     -16.532  12.146  43.449  0.00  0.00           H
ATOM    235  N    TYR A  26     -11.456  16.867  45.414  1.00  2.00           N
ATOM    236  CA   TYR A  26     -10.956  17.840  46.389  1.00  2.00           C
ATOM    237  C    TYR A  26     -12.057  18.638  47.045  1.00  2.60           C
ATOM    238  O    TYR A  26     -13.162  18.746  46.515  1.00  2.96           O
```

Fig 4-5

```
ATOM    239  CB   TYR A  26      -9.950  18.827  45.770  1.00  3.39           C
ATOM    240  CG   TYR A  26     -10.570  19.839  44.824  1.00  8.68           C
ATOM    241  CD1  TYR A  26     -10.831  19.497  43.495  1.00 11.88           C
ATOM    242  CD2  TYR A  26     -11.017  21.080  45.279  1.00  7.15           C
ATOM    243  CE1  TYR A  26     -11.536  20.342  42.651  1.00  8.71           C
ATOM    244  CE2  TYR A  26     -11.725  21.939  44.434  1.00 11.31           C
ATOM    245  CZ   TYR A  26     -11.982  21.551  43.122  1.00  9.36           C
ATOM    246  OH   TYR A  26     -12.704  22.348  42.274  1.00  9.02           O
ATOM    247  H    TYR A  26     -12.071  17.155  44.712  0.00  0.00           H
ATOM    248  HH   TYR A  26     -12.792  21.935  41.411  0.00  0.00           H
ATOM    249  N    THR A  27     -11.778  19.056  48.276  1.00  8.98           N
ATOM    250  CA   THR A  27     -12.469  20.164  48.924  1.00  3.70           C
ATOM    251  C    THR A  27     -11.436  21.213  49.273  1.00  2.00           C
ATOM    252  O    THR A  27     -10.365  20.891  49.784  1.00  2.00           O
ATOM    253  CB   THR A  27     -13.138  19.737  50.219  1.00  3.82           C
ATOM    254  OG1  THR A  27     -13.987  18.606  49.972  1.00  5.37           O
ATOM    255  CG2  THR A  27     -13.957  20.891  50.779  1.00  2.73           C
ATOM    256  H    THR A  27     -11.030  18.611  48.735  0.00  0.00           H
ATOM    257  HG1  THR A  27     -13.409  17.851  49.785  0.00  0.00           H
ATOM    258  N    GLY A  28     -11.664  22.419  48.779  1.00  5.64           N
ATOM    259  CA   GLY A  28     -10.813  23.538  49.128  1.00  8.04           C
ATOM    260  C    GLY A  28     -11.438  24.437  50.175  1.00  8.15           C
ATOM    261  O    GLY A  28     -12.646  24.729  50.131  1.00  9.73           O
ATOM    262  H    GLY A  28     -12.274  22.498  48.038  0.00  0.00           H
ATOM    263  N    MET A  29     -10.619  24.887  51.117  1.00  4.38           N
ATOM    264  CA   MET A  29     -11.091  25.812  52.138  1.00  6.14           C
ATOM    265  C    MET A  29     -10.033  26.845  52.477  1.00  6.50           C
ATOM    266  O    MET A  29      -8.847  26.630  52.242  1.00  5.89           O
ATOM    267  CB   MET A  29     -11.512  25.047  53.404  1.00 11.72           C
ATOM    268  CG   MET A  29     -10.445  24.128  53.999  1.00 14.88           C
ATOM    269  SD   MET A  29     -11.065  22.500  54.510  1.00  7.90           S
ATOM    270  CE   MET A  29     -12.824  22.854  54.721  1.00  5.60           C
ATOM    271  H    MET A  29      -9.683  24.601  51.122  0.00  0.00           H
ATOM    272  N    LEU A  30     -10.477  28.013  52.923  1.00 11.28           N
ATOM    273  CA   LEU A  30      -9.561  29.028  53.443  1.00 14.74           C
ATOM    274  C    LEU A  30      -9.042  28.573  54.805  1.00 14.12           C
ATOM    275  O    LEU A  30      -9.664  27.732  55.453  1.00 16.16           O
ATOM    276  CB   LEU A  30     -10.281  30.379  53.572  1.00 12.99           C
ATOM    277  CG   LEU A  30     -10.887  30.967  52.292  1.00 10.36           C
ATOM    278  CD1  LEU A  30     -12.064  31.842  52.668  1.00 12.99           C
ATOM    279  CD2  LEU A  30      -9.848  31.761  51.510  1.00  3.34           C
ATOM    280  H    LEU A  30     -11.444  28.168  52.902  0.00  0.00           H
ATOM    281  N    GLU A  31      -7.944  29.169  55.262  1.00 14.66           N
ATOM    282  CA   GLU A  31      -7.266  28.722  56.483  1.00 17.28           C
ATOM    283  C    GLU A  31      -8.187  28.313  57.642  1.00 18.96           C
ATOM    284  O    GLU A  31      -8.008  27.258  58.262  1.00 18.93           O
ATOM    285  CB   GLU A  31      -6.294  29.799  56.962  1.00 14.61           C
ATOM    286  CG   GLU A  31      -5.818  29.586  58.382  1.00 22.25           C
ATOM    287  CD   GLU A  31      -4.510  30.284  58.698  1.00 26.77           C
ATOM    288  OE1  GLU A  31      -4.245  31.362  58.107  1.00 21.74           O
ATOM    289  OE2  GLU A  31      -3.774  29.762  59.576  1.00 23.08           O
ATOM    290  H    GLU A  31      -7.506  29.828  54.682  0.00  0.00           H
ATOM    291  N    ASP A  32      -9.238  29.090  57.855  1.00 17.34           N
ATOM    292  CA   ASP A  32     -10.116  28.866  58.996  1.00 19.84           C
ATOM    293  C    ASP A  32     -11.096  27.713  58.816  1.00 18.08           C
ATOM    294  O    ASP A  32     -11.986  27.541  59.638  1.00 17.85           O
ATOM    295  CB   ASP A  32     -10.894  30.142  59.308  1.00 27.98           C
ATOM    296  CG   ASP A  32     -11.601  30.704  58.090  1.00 34.72           C
ATOM    297  OD1  ASP A  32     -12.727  30.254  57.801  1.00 32.49           O
ATOM    298  OD2  ASP A  32     -11.023  31.588  57.415  1.00 43.34           O
```

Fig 4-6

| ATOM | 299 | H | ASP | A | 32 | -9.405 | 29.814 | 57.223 | 0.00 | 0.00 | H |
|---|---|---|---|---|---|---|---|---|---|---|---|
| ATOM | 300 | N | GLY | A | 33 | -10.994 | 26.998 | 57.697 | 1.00 | 18.90 | N |
| ATOM | 301 | CA | GLY | A | 33 | -11.909 | 25.896 | 57.417 | 1.00 | 14.65 | C |
| ATOM | 302 | C | GLY | A | 33 | -13.146 | 26.270 | 56.616 | 1.00 | 10.95 | C |
| ATOM | 303 | O | GLY | A | 33 | -14.020 | 25.437 | 56.370 | 1.00 | 11.28 | O |
| ATOM | 304 | H | GLY | A | 33 | -10.204 | 27.111 | 57.137 | 0.00 | 0.00 | H |
| ATOM | 305 | N | LYS | A | 34 | -13.235 | 27.536 | 56.230 | 1.00 | 5.53 | N |
| ATOM | 306 | CA | LYS | A | 34 | -14.320 | 27.999 | 55.379 | 1.00 | 7.65 | C |
| ATOM | 307 | C | LYS | A | 34 | -14.222 | 27.369 | 53.991 | 1.00 | 7.56 | C |
| ATOM | 308 | O | LYS | A | 34 | -13.290 | 27.653 | 53.232 | 1.00 | 3.26 | O |
| ATOM | 309 | CB | LYS | A | 34 | -14.270 | 29.521 | 55.255 | 1.00 | 15.91 | C |
| ATOM | 310 | CG | LYS | A | 34 | -15.468 | 30.131 | 54.554 | 1.00 | 23.47 | C |
| ATOM | 311 | CD | LYS | A | 34 | -15.360 | 31.646 | 54.513 | 1.00 | 34.71 | C |
| ATOM | 312 | CE | LYS | A | 34 | -15.213 | 32.245 | 55.918 | 1.00 | 38.38 | C |
| ATOM | 313 | NZ | LYS | A | 34 | -13.805 | 32.635 | 56.227 | 1.00 | 41.83 | N |
| ATOM | 314 | H | LYS | A | 34 | -12.565 | 28.159 | 56.564 | 0.00 | 0.00 | H |
| ATOM | 315 | 1HZ | LYS | A | 34 | -13.475 | 33.324 | 55.520 | 0.00 | 0.00 | H |
| ATOM | 316 | 2HZ | LYS | A | 34 | -13.749 | 33.055 | 57.176 | 0.00 | 0.00 | H |
| ATOM | 317 | 3HZ | LYS | A | 34 | -13.196 | 31.792 | 56.185 | 0.00 | 0.00 | H |
| ATOM | 318 | N | LYS | A | 35 | -15.067 | 26.371 | 53.757 | 1.00 | 8.73 | N |
| ATOM | 319 | CA | LYS | A | 35 | -15.178 | 25.719 | 52.459 | 1.00 | 8.15 | C |
| ATOM | 320 | C | LYS | A | 35 | -15.520 | 26.736 | 51.378 | 1.00 | 13.32 | C |
| ATOM | 321 | O | LYS | A | 35 | -16.387 | 27.596 | 51.587 | 1.00 | 16.59 | O |
| ATOM | 322 | CB | LYS | A | 35 | -16.269 | 24.657 | 52.511 | 1.00 | 2.40 | C |
| ATOM | 323 | CG | LYS | A | 35 | -16.379 | 23.854 | 51.249 | 1.00 | 7.41 | C |
| ATOM | 324 | CD | LYS | A | 35 | -17.142 | 22.573 | 51.484 | 1.00 | 11.33 | C |
| ATOM | 325 | CE | LYS | A | 35 | -18.637 | 22.803 | 51.464 | 1.00 | 15.67 | C |
| ATOM | 326 | NZ | LYS | A | 35 | -19.352 | 21.501 | 51.304 | 1.00 | 20.77 | N |
| ATOM | 327 | H | LYS | A | 35 | -15.554 | 26.012 | 54.530 | 0.00 | 0.00 | H |
| ATOM | 328 | 1HZ | LYS | A | 35 | -19.004 | 21.025 | 50.450 | 0.00 | 0.00 | H |
| ATOM | 329 | 2HZ | LYS | A | 35 | -19.180 | 20.892 | 52.129 | 0.00 | 0.00 | H |
| ATOM | 330 | 3HZ | LYS | A | 35 | -20.373 | 21.681 | 51.212 | 0.00 | 0.00 | H |
| ATOM | 331 | N | PHE | A | 36 | -14.796 | 26.690 | 50.257 | 1.00 | 12.19 | N |
| ATOM | 332 | CA | PHE | A | 36 | -15.167 | 27.504 | 49.098 | 1.00 | 8.93 | C |
| ATOM | 333 | C | PHE | A | 36 | -15.553 | 26.696 | 47.861 | 1.00 | 11.24 | C |
| ATOM | 334 | O | PHE | A | 36 | -16.499 | 27.050 | 47.152 | 1.00 | 9.15 | O |
| ATOM | 335 | CB | PHE | A | 36 | -14.077 | 28.541 | 48.753 | 1.00 | 4.86 | C |
| ATOM | 336 | CG | PHE | A | 36 | -12.728 | 27.959 | 48.415 | 1.00 | 3.36 | C |
| ATOM | 337 | CD1 | PHE | A | 36 | -12.470 | 27.442 | 47.151 | 1.00 | 7.57 | C |
| ATOM | 338 | CD2 | PHE | A | 36 | -11.660 | 28.108 | 49.295 | 1.00 | 4.33 | C |
| ATOM | 339 | CE1 | PHE | A | 36 | -11.167 | 27.092 | 46.766 | 1.00 | 5.95 | C |
| ATOM | 340 | CE2 | PHE | A | 36 | -10.350 | 27.758 | 48.916 | 1.00 | 5.11 | C |
| ATOM | 341 | CZ | PHE | A | 36 | -10.110 | 27.250 | 47.648 | 1.00 | 2.00 | C |
| ATOM | 342 | H | PHE | A | 36 | -13.981 | 26.149 | 50.278 | 0.00 | 0.00 | H |
| ATOM | 343 | N | ASP | A | 37 | -14.972 | 25.507 | 47.738 | 1.00 | 11.21 | N |
| ATOM | 344 | CA | ASP | A | 37 | -15.201 | 24.672 | 46.568 | 1.00 | 8.81 | C |
| ATOM | 345 | C | ASP | A | 37 | -14.874 | 23.199 | 46.864 | 1.00 | 2.00 | C |
| ATOM | 346 | O | ASP | A | 37 | -13.905 | 22.904 | 47.545 | 1.00 | 2.01 | O |
| ATOM | 347 | CB | ASP | A | 37 | -14.340 | 25.220 | 45.416 | 1.00 | 12.70 | C |
| ATOM | 348 | CG | ASP | A | 37 | -14.583 | 24.518 | 44.091 | 1.00 | 11.57 | C |
| ATOM | 349 | OD1 | ASP | A | 37 | -15.679 | 23.968 | 43.855 | 1.00 | 7.88 | O |
| ATOM | 350 | OD2 | ASP | A | 37 | -13.665 | 24.565 | 43.254 | 1.00 | 15.66 | O |
| ATOM | 351 | H | ASP | A | 37 | -14.365 | 25.202 | 48.445 | 0.00 | 0.00 | H |
| ATOM | 352 | N | SER | A | 38 | -15.751 | 22.291 | 46.450 | 1.00 | 2.52 | N |
| ATOM | 353 | CA | SER | A | 38 | -15.461 | 20.850 | 46.493 | 1.00 | 2.33 | C |
| ATOM | 354 | C | SER | A | 38 | -16.108 | 20.110 | 45.349 | 1.00 | 2.00 | C |
| ATOM | 355 | O | SER | A | 38 | -17.313 | 20.210 | 45.168 | 1.00 | 2.31 | O |
| ATOM | 356 | CB | SER | A | 38 | -15.954 | 20.223 | 47.800 | 1.00 | 12.19 | C |
| ATOM | 357 | OG | SER | A | 38 | -15.979 | 18.804 | 47.722 | 1.00 | 9.54 | O |
| ATOM | 358 | H | SER | A | 38 | -16.607 | 22.613 | 46.095 | 0.00 | 0.00 | H |

Fig 4-7

| ATOM | 359 | HG | SER A | 38 | -15.613 | 18.490 | 48.571 | 0.00 | 0.00 | H |
| --- | --- | --- | --- | --- | --- | --- | --- | --- | --- | --- |
| ATOM | 360 | N | SER A | 39 | -15.339 | 19.252 | 44.684 | 1.00 | 2.00 | N |
| ATOM | 361 | CA | SER A | 39 | -15.840 | 18.414 | 43.584 | 1.00 | 3.72 | C |
| ATOM | 362 | C | SER A | 39 | -16.762 | 17.317 | 44.088 | 1.00 | 9.63 | C |
| ATOM | 363 | O | SER A | 39 | -17.547 | 16.751 | 43.324 | 1.00 | 6.74 | O |
| ATOM | 364 | CB | SER A | 39 | -14.682 | 17.758 | 42.825 | 1.00 | 3.50 | C |
| ATOM | 365 | OG | SER A | 39 | -13.861 | 16.976 | 43.683 | 1.00 | 3.28 | O |
| ATOM | 366 | H | SER A | 39 | -14.397 | 19.223 | 44.967 | 0.00 | 0.00 | H |
| ATOM | 367 | HG | SER A | 39 | -14.195 | 17.054 | 44.589 | 0.00 | 0.00 | H |
| ATOM | 368 | N | ARG A | 40 | -16.624 | 16.994 | 45.376 | 1.00 | 13.48 | N |
| ATOM | 369 | CA | ARG A | 40 | -17.441 | 15.972 | 46.025 | 1.00 | 12.15 | C |
| ATOM | 370 | C | ARG A | 40 | -18.883 | 16.433 | 46.270 | 1.00 | 17.11 | C |
| ATOM | 371 | O | ARG A | 40 | -19.798 | 15.612 | 46.350 | 1.00 | 17.06 | O |
| ATOM | 372 | CB | ARG A | 40 | -16.800 | 15.538 | 47.345 | 1.00 | 4.43 | C |
| ATOM | 373 | CG | ARG A | 40 | -15.385 | 15.003 | 47.220 | 1.00 | 2.00 | C |
| ATOM | 374 | CD | ARG A | 40 | -14.978 | 14.243 | 48.484 | 1.00 | 3.29 | C |
| ATOM | 375 | NE | ARG A | 40 | -13.546 | 13.940 | 48.561 | 1.00 | 4.66 | N |
| ATOM | 376 | CZ | ARG A | 40 | -13.031 | 12.714 | 48.497 | 1.00 | 2.00 | C |
| ATOM | 377 | NH1 | ARG A | 40 | -13.812 | 11.673 | 48.262 | 1.00 | 2.00 | N |
| ATOM | 378 | NH2 | ARG A | 40 | -11.727 | 12.527 | 48.631 | 1.00 | 2.00 | N |
| ATOM | 379 | H | ARG A | 40 | -16.027 | 17.536 | 45.944 | 0.00 | 0.00 | H |
| ATOM | 380 | HE | ARG A | 40 | -12.924 | 14.683 | 48.660 | 0.00 | 0.00 | H |
| ATOM | 381 | 1HH1 | ARG A | 40 | -14.794 | 11.785 | 48.128 | 0.00 | 0.00 | H |
| ATOM | 382 | 2HH1 | ARG A | 40 | -13.417 | 10.752 | 48.214 | 0.00 | 0.00 | H |
| ATOM | 383 | 1HH2 | ARG A | 40 | -11.112 | 13.308 | 48.782 | 0.00 | 0.00 | H |
| ATOM | 384 | 2HH2 | ARG A | 40 | -11.374 | 11.597 | 48.585 | 0.00 | 0.00 | H |
| ATOM | 385 | N | ASP A | 41 | -19.085 | 17.746 | 46.370 | 1.00 | 20.79 | N |
| ATOM | 386 | CA | ASP A | 41 | -20.435 | 18.315 | 46.454 | 1.00 | 26.68 | C |
| ATOM | 387 | C | ASP A | 41 | -21.187 | 18.206 | 45.124 | 1.00 | 30.48 | C |
| ATOM | 388 | O | ASP A | 41 | -22.416 | 18.085 | 45.106 | 1.00 | 31.53 | O |
| ATOM | 389 | CB | ASP A | 41 | -20.375 | 19.784 | 46.879 | 1.00 | 26.55 | C |
| ATOM | 390 | CG | ASP A | 41 | -19.641 | 19.993 | 48.195 | 1.00 | 34.97 | C |
| ATOM | 391 | OD1 | ASP A | 41 | -19.251 | 19.001 | 48.852 | 1.00 | 38.14 | O |
| ATOM | 392 | OD2 | ASP A | 41 | -19.426 | 21.167 | 48.559 | 1.00 | 36.52 | O |
| ATOM | 393 | H | ASP A | 41 | -18.307 | 18.340 | 46.438 | 0.00 | 0.00 | H |
| ATOM | 394 | N | ARG A | 42 | -20.447 | 18.307 | 44.018 | 1.00 | 31.99 | N |
| ATOM | 395 | CA | ARG A | 42 | -21.006 | 18.124 | 42.676 | 1.00 | 26.25 | C |
| ATOM | 396 | C | ARG A | 42 | -21.051 | 16.642 | 42.320 | 1.00 | 25.62 | C |
| ATOM | 397 | O | ARG A | 42 | -21.679 | 16.252 | 41.338 | 1.00 | 29.04 | O |
| ATOM | 398 | CB | ARG A | 42 | -20.168 | 18.865 | 41.625 | 1.00 | 22.17 | C |
| ATOM | 399 | CG | ARG A | 42 | -19.815 | 20.302 | 41.976 | 1.00 | 26.16 | C |
| ATOM | 400 | CD | ARG A | 42 | -18.697 | 20.840 | 41.089 | 1.00 | 29.95 | C |
| ATOM | 401 | NE | ARG A | 42 | -17.703 | 19.814 | 40.769 | 1.00 | 40.62 | N |
| ATOM | 402 | CZ | ARG A | 42 | -16.491 | 20.058 | 40.273 | 1.00 | 44.80 | C |
| ATOM | 403 | NH1 | ARG A | 42 | -16.070 | 21.306 | 40.089 | 1.00 | 47.04 | N |
| ATOM | 404 | NH2 | ARG A | 42 | -15.684 | 19.045 | 39.978 | 1.00 | 43.55 | N |
| ATOM | 405 | H | ARG A | 42 | -19.519 | 18.595 | 44.120 | 0.00 | 0.00 | H |
| ATOM | 406 | HE | ARG A | 42 | -17.911 | 18.869 | 40.922 | 0.00 | 0.00 | H |
| ATOM | 407 | 1HH1 | ARG A | 42 | -16.655 | 22.080 | 40.328 | 0.00 | 0.00 | H |
| ATOM | 408 | 2HH1 | ARG A | 42 | -15.156 | 21.465 | 39.719 | 0.00 | 0.00 | H |
| ATOM | 409 | 1HH2 | ARG A | 42 | -16.002 | 18.108 | 40.125 | 0.00 | 0.00 | H |
| ATOM | 410 | 2HH2 | ARG A | 42 | -14.773 | 19.213 | 39.600 | 0.00 | 0.00 | H |
| ATOM | 411 | N | ASN A | 43 | -20.302 | 15.832 | 43.064 | 1.00 | 20.94 | N |
| ATOM | 412 | CA | ASN A | 43 | -20.290 | 14.392 | 42.840 | 1.00 | 21.52 | C |
| ATOM | 413 | C | ASN A | 43 | -19.628 | 14.078 | 41.498 | 1.00 | 20.93 | C |
| ATOM | 414 | O | ASN A | 43 | -20.087 | 13.228 | 40.740 | 1.00 | 21.51 | O |
| ATOM | 415 | CB | ASN A | 43 | -21.724 | 13.852 | 42.869 | 1.00 | 23.52 | C |
| ATOM | 416 | CG | ASN A | 43 | -21.808 | 12.455 | 43.431 | 1.00 | 28.90 | C |
| ATOM | 417 | OD1 | ASN A | 43 | -20.789 | 11.802 | 43.662 | 1.00 | 28.67 | O |
| ATOM | 418 | ND2 | ASN A | 43 | -23.025 | 11.987 | 43.662 | 1.00 | 33.33 | N |

Fig 4-8

```
ATOM    419  H    ASN A   43     -19.786  16.217  43.793  0.00   0.00           H
ATOM    420  1HD2 ASN A   43     -23.041  11.094  44.043  0.00   0.00           H
ATOM    421  2HD2 ASN A   43     -23.786  12.557  43.466  0.00   0.00           H
ATOM    422  N    LYS A   44     -18.475  14.696  41.275  1.00  20.83           N
ATOM    423  CA   LYS A   44     -17.874  14.757  39.947  1.00  19.75           C
ATOM    424  C    LYS A   44     -16.361  15.014  40.049  1.00  17.91           C
ATOM    425  O    LYS A   44     -15.928  16.029  40.596  1.00  21.43           O
ATOM    426  CB   LYS A   44     -18.554  15.879  39.148  1.00  24.43           C
ATOM    427  CG   LYS A   44     -18.478  15.755  37.638  1.00  23.61           C
ATOM    428  CD   LYS A   44     -18.796  17.084  36.965  1.00  29.64           C
ATOM    429  CE   LYS A   44     -20.212  17.565  37.282  1.00  34.29           C
ATOM    430  NZ   LYS A   44     -20.543  18.848  36.583  1.00  38.07           N
ATOM    431  H    LYS A   44     -18.152  15.288  41.984  0.00   0.00           H
ATOM    432  1HZ  LYS A   44     -19.853  19.580  36.854  0.00   0.00           H
ATOM    433  2HZ  LYS A   44     -20.497  18.697  35.555  0.00   0.00           H
ATOM    434  3HZ  LYS A   44     -21.496  19.168  36.846  0.00   0.00           H
ATOM    435  N    PRO A   45     -15.545  14.014  39.695  1.00  16.30           N
ATOM    436  CA   PRO A   45     -14.093  14.182  39.830  1.00  17.48           C
ATOM    437  C    PRO A   45     -13.496  15.228  38.887  1.00  15.55           C
ATOM    438  O    PRO A   45     -13.942  15.399  37.753  1.00  17.90           O
ATOM    439  CB   PRO A   45     -13.539  12.779  39.557  1.00  14.90           C
ATOM    440  CG   PRO A   45     -14.679  11.871  39.886  1.00  19.40           C
ATOM    441  CD   PRO A   45     -15.909  12.612  39.438  1.00  17.34           C
ATOM    442  N    PHE A   46     -12.501  15.942  39.389  1.00  11.92           N
ATOM    443  CA   PHE A   46     -11.825  16.989  38.637  1.00  10.26           C
ATOM    444  C    PHE A   46     -10.644  16.371  37.898  1.00  10.45           C
ATOM    445  O    PHE A   46      -9.984  15.479  38.421  1.00  16.71           O
ATOM    446  CB   PHE A   46     -11.346  18.068  39.615  1.00   7.26           C
ATOM    447  CG   PHE A   46     -10.549  19.165  38.980  1.00   2.00           C
ATOM    448  CD1  PHE A   46     -11.180  20.149  38.222  1.00   2.00           C
ATOM    449  CD2  PHE A   46      -9.192  19.284  39.246  1.00   2.00           C
ATOM    450  CE1  PHE A   46     -10.475  21.243  37.749  1.00   2.00           C
ATOM    451  CE2  PHE A   46      -8.472  20.369  38.779  1.00   2.30           C
ATOM    452  CZ   PHE A   46      -9.117  21.357  38.030  1.00   5.96           C
ATOM    453  H    PHE A   46     -12.151  15.695  40.268  0.00   0.00           H
ATOM    454  N    LYS A   47     -10.421  16.782  36.655  1.00   9.72           N
ATOM    455  CA   LYS A   47      -9.293  16.255  35.893  1.00   4.83           C
ATOM    456  C    LYS A   47      -8.435  17.389  35.395  1.00   2.00           C
ATOM    457  O    LYS A   47      -8.943  18.449  35.061  1.00   2.00           O
ATOM    458  CB   LYS A   47      -9.770  15.421  34.700  1.00   5.22           C
ATOM    459  CG   LYS A   47     -10.510  14.147  35.058  1.00   8.65           C
ATOM    460  CD   LYS A   47     -11.587  13.853  34.032  1.00  11.93           C
ATOM    461  CE   LYS A   47     -11.326  12.543  33.312  1.00  10.86           C
ATOM    462  NZ   LYS A   47     -11.608  11.397  34.216  1.00  15.06           N
ATOM    463  H    LYS A   47     -11.004  17.458  36.253  0.00   0.00           H
ATOM    464  1HZ  LYS A   47     -12.594  11.462  34.542  0.00   0.00           H
ATOM    465  2HZ  LYS A   47     -11.471  10.498  33.712  0.00   0.00           H
ATOM    466  3HZ  LYS A   47     -10.981  11.442  35.042  0.00   0.00           H
ATOM    467  N    PHE A   48      -7.125  17.205  35.472  1.00   2.00           N
ATOM    468  CA   PHE A   48      -6.191  18.157  34.896  1.00   6.26           C
ATOM    469  C    PHE A   48      -4.866  17.469  34.538  1.00  10.81           C
ATOM    470  O    PHE A   48      -4.480  16.476  35.159  1.00  16.65           O
ATOM    471  CB   PHE A   48      -5.964  19.323  35.875  1.00   2.45           C
ATOM    472  CG   PHE A   48      -4.948  19.036  36.942  1.00   4.20           C
ATOM    473  CD1  PHE A   48      -5.254  18.188  38.005  1.00   2.00           C
ATOM    474  CD2  PHE A   48      -3.650  19.548  36.837  1.00   2.00           C
ATOM    475  CE1  PHE A   48      -4.282  17.837  38.936  1.00   2.00           C
ATOM    476  CE2  PHE A   48      -2.664  19.200  37.769  1.00   2.59           C
ATOM    477  CZ   PHE A   48      -2.983  18.340  38.817  1.00   2.53           C
ATOM    478  H    PHE A   48      -6.799  16.438  35.994  0.00   0.00           H
```

Fig 4-9

```
ATOM    479  N   MET A  49      -4.181  17.984  33.526  1.00 13.39           N
ATOM    480  CA  MET A  49      -2.892  17.437  33.113  1.00 16.66           C
ATOM    481  C   MET A  49      -1.768  18.109  33.898  1.00 16.05           C
ATOM    482  O   MET A  49      -1.749  19.332  34.046  1.00 17.38           O
ATOM    483  CB  MET A  49      -2.690  17.663  31.614  1.00 22.76           C
ATOM    484  CG  MET A  49      -1.538  16.885  31.016  1.00 32.61           C
ATOM    485  SD  MET A  49      -0.985  17.585  29.454  1.00 46.48           S
ATOM    486  CE  MET A  49      -0.812  16.105  28.435  1.00 45.16           C
ATOM    487  H   MET A  49      -4.543  18.774  33.084  0.00  0.00           H
ATOM    488  N   LEU A  50      -0.852  17.314  34.433  1.00 16.03           N
ATOM    489  CA  LEU A  50       0.166  17.848  35.336  1.00 16.25           C
ATOM    490  C   LEU A  50       1.398  18.380  34.606  1.00 18.27           C
ATOM    491  O   LEU A  50       2.130  17.629  33.962  1.00 17.62           O
ATOM    492  CB  LEU A  50       0.587  16.777  36.350  1.00 16.08           C
ATOM    493  CG  LEU A  50       1.737  17.151  37.290  1.00 15.77           C
ATOM    494  CD1 LEU A  50       1.189  17.731  38.587  1.00 17.22           C
ATOM    495  CD2 LEU A  50       2.591  15.923  37.561  1.00 17.09           C
ATOM    496  H   LEU A  50      -0.925  16.348  34.258  0.00  0.00           H
ATOM    497  N   GLY A  51       1.659  19.671  34.773  1.00 24.68           N
ATOM    498  CA  GLY A  51       2.832  20.281  34.163  1.00 28.29           C
ATOM    499  C   GLY A  51       2.511  21.451  33.246  1.00 30.06           C
ATOM    500  O   GLY A  51       3.312  22.367  33.092  1.00 31.10           O
ATOM    501  H   GLY A  51       1.071  20.196  35.347  0.00  0.00           H
ATOM    502  N   LYS A  52       1.283  21.482  32.739  1.00 31.85           N
ATOM    503  CA  LYS A  52       0.883  22.452  31.724  1.00 30.54           C
ATOM    504  C   LYS A  52       0.475  23.795  32.323  1.00 27.06           C
ATOM    505  O   LYS A  52      -0.349  24.498  31.741  1.00 30.79           O
ATOM    506  CB  LYS A  52      -0.281  21.887  30.899  1.00 33.91           C
ATOM    507  CG  LYS A  52      -0.110  20.427  30.479  1.00 38.74           C
ATOM    508  CD  LYS A  52       1.015  20.263  29.458  1.00 44.12           C
ATOM    509  CE  LYS A  52       1.708  18.913  29.584  1.00 44.68           C
ATOM    510  NZ  LYS A  52       2.954  18.849  28.767  1.00 46.84           N
ATOM    511  H   LYS A  52       0.651  20.805  33.051  0.00  0.00           H
ATOM    512  1HZ LYS A  52       2.732  19.066  27.773  0.00  0.00           H
ATOM    513  2HZ LYS A  52       3.632  19.546  29.134  0.00  0.00           H
ATOM    514  3HZ LYS A  52       3.361  17.895  28.831  0.00  0.00           H
ATOM    515  N   GLN A  53       1.025  24.130  33.490  1.00 21.58           N
ATOM    516  CA  GLN A  53       0.572  25.282  34.279  1.00 18.83           C
ATOM    517  C   GLN A  53      -0.950  25.457  34.313  1.00 15.57           C
ATOM    518  O   GLN A  53      -1.456  26.570  34.380  1.00 17.17           O
ATOM    519  CB  GLN A  53       1.219  26.571  33.768  1.00 25.35           C
ATOM    520  CG  GLN A  53       2.599  26.848  34.333  1.00 34.50           C
ATOM    521  CD  GLN A  53       3.585  25.737  34.025  1.00 42.12           C
ATOM    522  OE1 GLN A  53       3.854  25.432  32.865  1.00 46.61           O
ATOM    523  NE2 GLN A  53       4.096  25.098  35.067  1.00 46.53           N
ATOM    524  H   GLN A  53       1.847  23.671  33.747  0.00  0.00           H
ATOM    525  1HE2 GLN A  53      4.723  24.391  34.821  0.00  0.00           H
ATOM    526  2HE2 GLN A  53      3.837  25.352  35.970  0.00  0.00           H
ATOM    527  N   GLU A  54      -1.672  24.344  34.338  1.00 12.00           N
ATOM    528  CA  GLU A  54      -3.126  24.378  34.306  1.00  6.49           C
ATOM    529  C   GLU A  54      -3.741  24.762  35.642  1.00  5.69           C
ATOM    530  O   GLU A  54      -4.873  25.238  35.696  1.00  4.44           O
ATOM    531  CB  GLU A  54      -3.666  23.022  33.878  1.00  6.66           C
ATOM    532  CG  GLU A  54      -4.296  23.020  32.516  1.00  4.63           C
ATOM    533  CD  GLU A  54      -4.414  21.628  31.960  1.00 11.57           C
ATOM    534  OE1 GLU A  54      -5.339  20.896  32.368  1.00 10.83           O
ATOM    535  OE2 GLU A  54      -3.543  21.242  31.157  1.00 18.19           O
ATOM    536  H   GLU A  54      -1.188  23.505  34.304  0.00  0.00           H
ATOM    537  N   VAL A  55      -3.035  24.444  36.722  1.00  4.70           N
ATOM    538  CA  VAL A  55      -3.513  24.731  38.071  1.00  6.95           C
```

Fig 4-10

```
ATOM    539  C    VAL A   55      -2.500   25.559   38.849   1.00   9.75           C
ATOM    540  O    VAL A   55      -1.369   25.737   38.408   1.00   9.34           O
ATOM    541  CB   VAL A   55      -3.774   23.446   38.849   1.00   3.43           C
ATOM    542  CG1  VAL A   55      -4.995   22.759   38.309   1.00   9.22           C
ATOM    543  CG2  VAL A   55      -2.573   22.538   38.761   1.00   2.21           C
ATOM    544  H    VAL A   55      -2.142   24.084   36.580   0.00   0.00           H
ATOM    545  N    ILE A   56      -2.887   26.026   40.031   1.00  12.04           N
ATOM    546  CA   ILE A   56      -1.964   26.785   40.869   1.00  10.94           C
ATOM    547  C    ILE A   56      -0.734   25.962   41.286   1.00  12.55           C
ATOM    548  O    ILE A   56      -0.759   24.729   41.270   1.00  15.13           O
ATOM    549  CB   ILE A   56      -2.674   27.365   42.123   1.00   9.38           C
ATOM    550  CG1  ILE A   56      -3.377   26.263   42.920   1.00   4.02           C
ATOM    551  CG2  ILE A   56      -3.665   28.449   41.701   1.00   9.44           C
ATOM    552  CD1  ILE A   56      -4.003   26.756   44.206   1.00   2.00           C
ATOM    553  H    ILE A   56      -3.799   25.844   40.322   0.00   0.00           H
ATOM    554  N    ARG A   57       0.353   26.651   41.615   1.00  10.58           N
ATOM    555  CA   ARG A   57       1.648   26.013   41.850   1.00  12.39           C
ATOM    556  C    ARG A   57       1.700   25.006   43.014   1.00  15.27           C
ATOM    557  O    ARG A   57       2.321   23.946   42.901   1.00  16.77           O
ATOM    558  CB   ARG A   57       2.707   27.091   42.058   1.00  13.28           C
ATOM    559  CG   ARG A   57       4.115   26.573   42.013   1.00  16.07           C
ATOM    560  CD   ARG A   57       5.090   27.708   42.068   1.00  18.63           C
ATOM    561  NE   ARG A   57       6.447   27.196   42.189   1.00  29.56           N
ATOM    562  CZ   ARG A   57       7.535   27.957   42.208   1.00  29.74           C
ATOM    563  NH1  ARG A   57       7.430   29.277   42.124   1.00  24.22           N
ATOM    564  NH2  ARG A   57       8.728   27.390   42.332   1.00  34.84           N
ATOM    565  H    ARG A   57       0.284   27.627   41.637   0.00   0.00           H
ATOM    566  HE   ARG A   57       6.567   26.228   42.278   0.00   0.00           H
ATOM    567 1HH1  ARG A   57       6.534   29.712   42.038   0.00   0.00           H
ATOM    568 2HH1  ARG A   57       8.258   29.836   42.149   0.00   0.00           H
ATOM    569 1HH2  ARG A   57       8.794   26.398   42.443   0.00   0.00           H
ATOM    570 2HH2  ARG A   57       9.551   27.954   42.380   0.00   0.00           H
ATOM    571  N    GLY A   58       1.084   25.349   44.142   1.00  13.48           N
ATOM    572  CA   GLY A   58       0.973   24.402   45.240   1.00  12.25           C
ATOM    573  C    GLY A   58       0.326   23.080   44.849   1.00   9.23           C
ATOM    574  O    GLY A   58       0.633   22.043   45.438   1.00   8.04           O
ATOM    575  H    GLY A   58       0.719   26.253   44.227   0.00   0.00           H
ATOM    576  N    TRP A   59      -0.567   23.124   43.856   1.00   6.52           N
ATOM    577  CA   TRP A   59      -1.177   21.927   43.269   1.00   2.00           C
ATOM    578  C    TRP A   59      -0.215   21.196   42.365   1.00   3.20           C
ATOM    579  O    TRP A   59      -0.186   19.969   42.345   1.00   9.79           O
ATOM    580  CB   TRP A   59      -2.399   22.294   42.443   1.00   2.00           C
ATOM    581  CG   TRP A   59      -3.672   22.138   43.172   1.00   2.87           C
ATOM    582  CD1  TRP A   59      -4.093   22.857   44.252   1.00   2.00           C
ATOM    583  CD2  TRP A   59      -4.707   21.189   42.889   1.00   4.49           C
ATOM    584  NE1  TRP A   59      -5.327   22.413   44.659   1.00   4.48           N
ATOM    585  CE2  TRP A   59      -5.725   21.386   43.843   1.00   5.98           C
ATOM    586  CE3  TRP A   59      -4.874   20.193   41.921   1.00   2.00           C
ATOM    587  CZ2  TRP A   59      -6.897   20.615   43.859   1.00   7.28           C
ATOM    588  CZ3  TRP A   59      -6.043   19.433   41.939   1.00   4.10           C
ATOM    589  CH2  TRP A   59      -7.033   19.648   42.900   1.00   2.01           C
ATOM    590  H    TRP A   59      -0.838   24.004   43.525   0.00   0.00           H
ATOM    591  HE1  TRP A   59      -5.830   22.768   45.422   0.00   0.00           H
ATOM    592  N    GLU A   60       0.507   21.955   41.550   1.00   3.19           N
ATOM    593  CA   GLU A   60       1.484   21.388   40.636   1.00   5.73           C
ATOM    594  C    GLU A   60       2.538   20.587   41.395   1.00   8.89           C
ATOM    595  O    GLU A   60       2.703   19.395   41.150   1.00  14.67           O
ATOM    596  CB   GLU A   60       2.142   22.502   39.819   1.00  10.18           C
ATOM    597  CG   GLU A   60       2.585   22.086   38.415   1.00  13.55           C
ATOM    598  CD   GLU A   60       1.463   22.147   37.398   1.00  16.71           C
```

Fig 4-11

| ATOM | 599 | OE1 | GLU | A | 60 | 0.393 | 21.551 | 37.640 | 1.00 | 19.83 | O |
|---|---|---|---|---|---|---|---|---|---|---|---|
| ATOM | 600 | OE2 | GLU | A | 60 | 1.649 | 22.793 | 36.348 | 1.00 | 22.45 | O |
| ATOM | 601 | H | GLU | A | 60 | 0.323 | 22.919 | 41.539 | 0.00 | 0.00 | H |
| ATOM | 602 | N | GLU | A | 61 | 3.116 | 21.189 | 42.428 | 1.00 | 11.93 | N |
| ATOM | 603 | CA | GLU | A | 61 | 4.123 | 20.510 | 43.249 | 1.00 | 15.22 | C |
| ATOM | 604 | C | GLU | A | 61 | 3.519 | 19.581 | 44.315 | 1.00 | 14.96 | C |
| ATOM | 605 | O | GLU | A | 61 | 4.101 | 18.558 | 44.663 | 1.00 | 21.59 | O |
| ATOM | 606 | CB | GLU | A | 61 | 5.053 | 21.533 | 43.916 | 1.00 | 18.18 | C |
| ATOM | 607 | CG | GLU | A | 61 | 5.177 | 22.868 | 43.171 | 1.00 | 28.20 | C |
| ATOM | 608 | CD | GLU | A | 61 | 6.615 | 23.314 | 42.926 | 1.00 | 31.43 | C |
| ATOM | 609 | OE1 | GLU | A | 61 | 7.478 | 23.101 | 43.807 | 1.00 | 35.07 | O |
| ATOM | 610 | OE2 | GLU | A | 61 | 6.865 | 23.933 | 41.867 | 1.00 | 34.62 | O |
| ATOM | 611 | H | GLU | A | 61 | 2.859 | 22.117 | 42.606 | 0.00 | 0.00 | H |
| ATOM | 612 | N | GLY | A | 62 | 2.355 | 19.938 | 44.840 | 1.00 | 16.29 | N |
| ATOM | 613 | CA | GLY | A | 62 | 1.687 | 19.077 | 45.801 | 1.00 | 12.82 | C |
| ATOM | 614 | C | GLY | A | 62 | 1.281 | 17.734 | 45.219 | 1.00 | 12.55 | C |
| ATOM | 615 | O | GLY | A | 62 | 1.782 | 16.697 | 45.639 | 1.00 | 12.58 | O |
| ATOM | 616 | H | GLY | A | 62 | 1.970 | 20.809 | 44.617 | 0.00 | 0.00 | H |
| ATOM | 617 | N | VAL | A | 63 | 0.438 | 17.764 | 44.190 | 1.00 | 12.60 | N |
| ATOM | 618 | CA | VAL | A | 63 | -0.092 | 16.550 | 43.570 | 1.00 | 12.62 | C |
| ATOM | 619 | C | VAL | A | 63 | 0.996 | 15.674 | 42.921 | 1.00 | 15.97 | C |
| ATOM | 620 | O | VAL | A | 63 | 0.927 | 14.446 | 42.958 | 1.00 | 18.69 | O |
| ATOM | 621 | CB | VAL | A | 63 | -1.164 | 16.899 | 42.511 | 1.00 | 7.73 | C |
| ATOM | 622 | CG1 | VAL | A | 63 | -1.788 | 15.628 | 41.954 | 1.00 | 7.25 | C |
| ATOM | 623 | CG2 | VAL | A | 63 | -2.234 | 17.780 | 43.122 | 1.00 | 3.26 | C |
| ATOM | 624 | H | VAL | A | 63 | 0.172 | 18.639 | 43.830 | 0.00 | 0.00 | H |
| ATOM | 625 | N | ALA | A | 64 | 2.048 | 16.305 | 42.416 | 1.00 | 15.67 | N |
| ATOM | 626 | CA | ALA | A | 64 | 3.196 | 15.570 | 41.905 | 1.00 | 14.59 | C |
| ATOM | 627 | C | ALA | A | 64 | 3.856 | 14.687 | 42.976 | 1.00 | 16.87 | C |
| ATOM | 628 | O | ALA | A | 64 | 4.548 | 13.726 | 42.656 | 1.00 | 19.52 | O |
| ATOM | 629 | CB | ALA | A | 64 | 4.201 | 16.542 | 41.338 | 1.00 | 13.86 | C |
| ATOM | 630 | H | ALA | A | 64 | 2.009 | 17.279 | 42.315 | 0.00 | 0.00 | H |
| ATOM | 631 | N | GLN | A | 65 | 3.657 | 15.026 | 44.245 | 1.00 | 16.81 | N |
| ATOM | 632 | CA | GLN | A | 65 | 4.202 | 14.233 | 45.353 | 1.00 | 14.57 | C |
| ATOM | 633 | C | GLN | A | 65 | 3.325 | 13.037 | 45.706 | 1.00 | 11.92 | C |
| ATOM | 634 | O | GLN | A | 65 | 3.694 | 12.226 | 46.553 | 1.00 | 12.99 | O |
| ATOM | 635 | CB | GLN | A | 65 | 4.359 | 15.097 | 46.606 | 1.00 | 15.78 | C |
| ATOM | 636 | CG | GLN | A | 65 | 5.473 | 16.118 | 46.542 | 1.00 | 27.03 | C |
| ATOM | 637 | CD | GLN | A | 65 | 5.524 | 16.996 | 47.782 | 1.00 | 35.69 | C |
| ATOM | 638 | OE1 | GLN | A | 65 | 5.543 | 16.500 | 48.910 | 1.00 | 39.86 | O |
| ATOM | 639 | NE2 | GLN | A | 65 | 5.516 | 18.307 | 47.580 | 1.00 | 36.82 | N |
| ATOM | 640 | H | GLN | A | 65 | 3.161 | 15.844 | 44.449 | 0.00 | 0.00 | H |
| ATOM | 641 | 1HE2 | GLN | A | 65 | 5.596 | 18.845 | 48.387 | 0.00 | 0.00 | H |
| ATOM | 642 | 2HE2 | GLN | A | 65 | 5.428 | 18.638 | 46.667 | 0.00 | 0.00 | H |
| ATOM | 643 | N | MET | A | 66 | 2.094 | 13.034 | 45.210 | 1.00 | 8.83 | N |
| ATOM | 644 | CA | MET | A | 66 | 1.119 | 12.044 | 45.646 | 1.00 | 9.40 | C |
| ATOM | 645 | C | MET | A | 66 | 1.186 | 10.788 | 44.774 | 1.00 | 13.38 | C |
| ATOM | 646 | O | MET | A | 66 | 1.705 | 10.831 | 43.660 | 1.00 | 16.22 | O |
| ATOM | 647 | CB | MET | A | 66 | -0.286 | 12.651 | 45.616 | 1.00 | 5.56 | C |
| ATOM | 648 | CG | MET | A | 66 | -0.487 | 13.766 | 46.628 | 1.00 | 3.07 | C |
| ATOM | 649 | SD | MET | A | 66 | -2.084 | 14.610 | 46.495 | 1.00 | 12.38 | S |
| ATOM | 650 | CE | MET | A | 66 | -3.186 | 13.301 | 46.911 | 1.00 | 12.15 | C |
| ATOM | 651 | H | MET | A | 66 | 1.872 | 13.655 | 44.491 | 0.00 | 0.00 | H |
| ATOM | 652 | N | SER | A | 67 | 0.832 | 9.643 | 45.346 | 1.00 | 13.44 | N |
| ATOM | 653 | CA | SER | A | 67 | 0.727 | 8.409 | 44.565 | 1.00 | 11.42 | C |
| ATOM | 654 | C | SER | A | 67 | -0.721 | 7.926 | 44.518 | 1.00 | 12.45 | C |
| ATOM | 655 | O | SER | A | 67 | -1.556 | 8.364 | 45.309 | 1.00 | 14.85 | O |
| ATOM | 656 | CB | SER | A | 67 | 1.649 | 7.317 | 45.134 | 1.00 | 7.60 | C |
| ATOM | 657 | OG | SER | A | 67 | 1.250 | 6.897 | 46.427 | 1.00 | 7.91 | O |
| ATOM | 658 | H | SER | A | 67 | 0.710 | 9.638 | 46.319 | 0.00 | 0.00 | H |

Fig 4-12

| | | | | | | | | | | |
|---|---|---|---|---|---|---|---|---|---|---|
| ATOM | 659 | HG | SER A | 67 | 1.986 | 7.045 | 47.038 | 0.00 | 0.00 | H |
| ATOM | 660 | N | VAL A | 68 | -1.055 | 7.115 | 43.523 | 1.00 | 12.38 | N |
| ATOM | 661 | CA | VAL A | 68 | -2.457 | 6.756 | 43.314 | 1.00 | 10.06 | C |
| ATOM | 662 | C | VAL A | 68 | -3.080 | 6.069 | 44.532 | 1.00 | 9.51 | C |
| ATOM | 663 | O | VAL A | 68 | -2.603 | 5.033 | 44.999 | 1.00 | 13.72 | O |
| ATOM | 664 | CB | VAL A | 68 | -2.647 | 5.854 | 42.067 | 1.00 | 5.10 | C |
| ATOM | 665 | CG1 | VAL A | 68 | -4.130 | 5.630 | 41.800 | 1.00 | 5.86 | C |
| ATOM | 666 | CG2 | VAL A | 68 | -2.010 | 6.489 | 40.874 | 1.00 | 2.65 | C |
| ATOM | 667 | H | VAL A | 68 | -0.361 | 6.855 | 42.883 | 0.00 | 0.00 | H |
| ATOM | 668 | N | GLY A | 69 | -4.190 | 6.630 | 44.992 | 1.00 | 7.92 | N |
| ATOM | 669 | CA | GLY A | 69 | -4.872 | 6.114 | 46.162 | 1.00 | 8.54 | C |
| ATOM | 670 | C | GLY A | 69 | -4.755 | 7.061 | 47.344 | 1.00 | 7.63 | C |
| ATOM | 671 | O | GLY A | 69 | -5.649 | 7.132 | 48.185 | 1.00 | 12.92 | O |
| ATOM | 672 | H | GLY A | 69 | -4.587 | 7.362 | 44.469 | 0.00 | 0.00 | H |
| ATOM | 673 | N | GLN A | 70 | -3.694 | 7.859 | 47.354 | 1.00 | 3.17 | N |
| ATOM | 674 | CA | GLN A | 70 | -3.357 | 8.660 | 48.515 | 1.00 | 2.00 | C |
| ATOM | 675 | C | GLN A | 70 | -4.299 | 9.830 | 48.671 | 1.00 | 2.00 | C |
| ATOM | 676 | O | GLN A | 70 | -4.749 | 10.400 | 47.691 | 1.00 | 3.88 | O |
| ATOM | 677 | CB | GLN A | 70 | -1.927 | 9.161 | 48.395 | 1.00 | 2.57 | C |
| ATOM | 678 | CG | GLN A | 70 | -1.483 | 10.064 | 49.524 | 1.00 | 10.26 | C |
| ATOM | 679 | CD | GLN A | 70 | -0.066 | 10.555 | 49.331 | 1.00 | 10.61 | C |
| ATOM | 680 | OE1 | GLN A | 70 | 0.673 | 10.028 | 48.505 | 1.00 | 18.69 | O |
| ATOM | 681 | NE2 | GLN A | 70 | 0.310 | 11.586 | 50.067 | 1.00 | 11.45 | N |
| ATOM | 682 | H | GLN A | 70 | -3.135 | 7.917 | 46.548 | 0.00 | 0.00 | H |
| ATOM | 683 | 1HE2 | GLN A | 70 | 1.237 | 11.850 | 49.896 | 0.00 | 0.00 | H |
| ATOM | 684 | 2HE2 | GLN A | 70 | -0.298 | 11.997 | 50.702 | 0.00 | 0.00 | H |
| ATOM | 685 | N | ARG A | 71 | -4.711 | 10.082 | 49.904 | 1.00 | 5.36 | N |
| ATOM | 686 | CA | ARG A | 71 | -5.486 | 11.274 | 50.246 | 1.00 | 5.53 | C |
| ATOM | 687 | C | ARG A | 71 | -4.650 | 12.208 | 51.114 | 1.00 | 3.03 | C |
| ATOM | 688 | O | ARG A | 71 | -4.006 | 11.764 | 52.060 | 1.00 | 4.39 | O |
| ATOM | 689 | CB | ARG A | 71 | -6.753 | 10.873 | 50.997 | 1.00 | 2.00 | C |
| ATOM | 690 | CG | ARG A | 71 | -7.697 | 12.010 | 51.228 | 1.00 | 2.00 | C |
| ATOM | 691 | CD | ARG A | 71 | -9.066 | 11.504 | 51.639 | 1.00 | 3.25 | C |
| ATOM | 692 | NE | ARG A | 71 | -9.812 | 12.542 | 52.347 | 1.00 | 8.85 | N |
| ATOM | 693 | CZ | ARG A | 71 | -11.134 | 12.564 | 52.475 | 1.00 | 18.29 | C |
| ATOM | 694 | NH1 | ARG A | 71 | -11.888 | 11.640 | 51.890 | 1.00 | 23.05 | N |
| ATOM | 695 | NH2 | ARG A | 71 | -11.708 | 13.525 | 53.183 | 1.00 | 25.79 | N |
| ATOM | 696 | H | ARG A | 71 | -4.639 | 9.362 | 50.543 | 0.00 | 0.00 | H |
| ATOM | 697 | HE | ARG A | 71 | -9.309 | 13.289 | 52.735 | 0.00 | 0.00 | H |
| ATOM | 698 | 1HH1 | ARG A | 71 | -11.460 | 10.906 | 51.361 | 0.00 | 0.00 | H |
| ATOM | 699 | 2HH1 | ARG A | 71 | -12.879 | 11.654 | 52.011 | 0.00 | 0.00 | H |
| ATOM | 700 | 1HH2 | ARG A | 71 | -11.149 | 14.237 | 53.609 | 0.00 | 0.00 | H |
| ATOM | 701 | 2HH2 | ARG A | 71 | -12.702 | 13.542 | 53.282 | 0.00 | 0.00 | H |
| ATOM | 702 | N | ALA A | 72 | -4.628 | 13.489 | 50.774 | 1.00 | 2.46 | N |
| ATOM | 703 | CA | ALA A | 72 | -3.725 | 14.428 | 51.425 | 1.00 | 2.00 | C |
| ATOM | 704 | C | ALA A | 72 | -4.326 | 15.803 | 51.654 | 1.00 | 4.21 | C |
| ATOM | 705 | O | ALA A | 72 | -5.376 | 16.145 | 51.119 | 1.00 | 10.57 | O |
| ATOM | 706 | CB | ALA A | 72 | -2.456 | 14.557 | 50.636 | 1.00 | 2.00 | C |
| ATOM | 707 | H | ALA A | 72 | -5.218 | 13.805 | 50.054 | 0.00 | 0.00 | H |
| ATOM | 708 | N | LYS A | 73 | -3.766 | 16.490 | 52.632 | 1.00 | 8.68 | N |
| ATOM | 709 | CA | LYS A | 73 | -4.121 | 17.861 | 52.917 | 1.00 | 4.13 | C |
| ATOM | 710 | C | LYS A | 73 | -2.943 | 18.713 | 52.488 | 1.00 | 4.72 | C |
| ATOM | 711 | O | LYS A | 73 | -1.794 | 18.396 | 52.814 | 1.00 | 6.20 | O |
| ATOM | 712 | CB | LYS A | 73 | -4.387 | 18.018 | 54.410 | 1.00 | 6.40 | C |
| ATOM | 713 | CG | LYS A | 73 | -4.104 | 19.408 | 54.956 | 1.00 | 13.82 | C |
| ATOM | 714 | CD | LYS A | 73 | -4.807 | 19.628 | 56.287 | 1.00 | 15.85 | C |
| ATOM | 715 | CE | LYS A | 73 | -4.136 | 20.729 | 57.086 | 1.00 | 18.32 | C |
| ATOM | 716 | NZ | LYS A | 73 | -5.033 | 21.240 | 58.148 | 1.00 | 22.33 | N |
| ATOM | 717 | H | LYS A | 73 | -3.101 | 16.042 | 53.199 | 0.00 | 0.00 | H |
| ATOM | 718 | 1HZ | LYS A | 73 | -5.920 | 21.583 | 57.728 | 0.00 | 0.00 | H |

Fig 4-13

| ATOM | 719 | 2HZ | LYS | A | 73 | -5.238 | 20.469 | 58.817 | 0.00 | 0.00 | H |
|------|-----|-----|-----|---|----|--------|--------|--------|------|------|---|
| ATOM | 720 | 3HZ | LYS | A | 73 | -4.569 | 22.019 | 58.657 | 0.00 | 0.00 | H |
| ATOM | 721 | N | LEU | A | 74 | -3.212 | 19.628 | 51.566 | 1.00 | 6.47 | N |
| ATOM | 722 | CA | LEU | A | 74 | -2.218 | 20.582 | 51.082 | 1.00 | 8.06 | C |
| ATOM | 723 | C | LEU | A | 74 | -2.403 | 21.962 | 51.695 | 1.00 | 8.90 | C |
| ATOM | 724 | O | LEU | A | 74 | -3.449 | 22.600 | 51.515 | 1.00 | 14.56 | O |
| ATOM | 725 | CB | LEU | A | 74 | -2.303 | 20.706 | 49.560 | 1.00 | 12.85 | C |
| ATOM | 726 | CG | LEU | A | 74 | -1.440 | 19.791 | 48.695 | 1.00 | 11.86 | C |
| ATOM | 727 | CD1 | LEU | A | 74 | -1.789 | 18.330 | 48.947 | 1.00 | 11.50 | C |
| ATOM | 728 | CD2 | LEU | A | 74 | -1.663 | 20.157 | 47.241 | 1.00 | 12.57 | C |
| ATOM | 729 | H | LEU | A | 74 | -4.064 | 19.565 | 51.121 | 0.00 | 0.00 | H |
| ATOM | 730 | N | THR | A | 75 | -1.385 | 22.431 | 52.405 | 1.00 | 7.32 | N |
| ATOM | 731 | CA | THR | A | 75 | -1.383 | 23.796 | 52.913 | 1.00 | 6.76 | C |
| ATOM | 732 | C | THR | A | 75 | -0.513 | 24.654 | 52.000 | 1.00 | 6.27 | C |
| ATOM | 733 | O | THR | A | 75 | 0.683 | 24.416 | 51.846 | 1.00 | 5.48 | O |
| ATOM | 734 | CB | THR | A | 75 | -0.905 | 23.830 | 54.397 | 1.00 | 6.87 | C |
| ATOM | 735 | OG1 | THR | A | 75 | -1.957 | 23.327 | 55.227 | 1.00 | 2.01 | O |
| ATOM | 736 | CG2 | THR | A | 75 | -0.556 | 25.238 | 54.861 | 1.00 | 3.73 | C |
| ATOM | 737 | H | THR | A | 75 | -0.717 | 21.784 | 52.717 | 0.00 | 0.00 | H |
| ATOM | 738 | HG1 | THR | A | 75 | -2.720 | 23.901 | 55.117 | 0.00 | 0.00 | H |
| ATOM | 739 | N | ILE | A | 76 | -1.180 | 25.508 | 51.234 | 1.00 | 10.43 | N |
| ATOM | 740 | CA | ILE | A | 76 | -0.542 | 26.284 | 50.167 | 1.00 | 11.16 | C |
| ATOM | 741 | C | ILE | A | 76 | -0.454 | 27.788 | 50.522 | 1.00 | 12.21 | C |
| ATOM | 742 | O | ILE | A | 76 | -1.476 | 28.460 | 50.752 | 1.00 | 13.89 | O |
| ATOM | 743 | CB | ILE | A | 76 | -1.326 | 26.090 | 48.830 | 1.00 | 6.31 | C |
| ATOM | 744 | CG1 | ILE | A | 76 | -1.388 | 24.601 | 48.459 | 1.00 | 5.62 | C |
| ATOM | 745 | CG2 | ILE | A | 76 | -0.653 | 26.827 | 47.719 | 1.00 | 9.44 | C |
| ATOM | 746 | CD1 | ILE | A | 76 | -2.630 | 24.205 | 47.691 | 1.00 | 2.00 | C |
| ATOM | 747 | H | ILE | A | 76 | -2.141 | 25.633 | 51.388 | 0.00 | 0.00 | H |
| ATOM | 748 | N | SER | A | 77 | 0.768 | 28.287 | 50.692 | 1.00 | 10.50 | N |
| ATOM | 749 | CA | SER | A | 77 | 0.947 | 29.700 | 51.009 | 1.00 | 11.73 | C |
| ATOM | 750 | C | SER | A | 77 | 0.681 | 30.566 | 49.790 | 1.00 | 12.45 | C |
| ATOM | 751 | O | SER | A | 77 | 0.922 | 30.149 | 48.662 | 1.00 | 15.48 | O |
| ATOM | 752 | CB | SER | A | 77 | 2.354 | 29.978 | 51.571 | 1.00 | 11.33 | C |
| ATOM | 753 | OG | SER | A | 77 | 3.405 | 29.669 | 50.667 | 1.00 | 18.57 | O |
| ATOM | 754 | H | SER | A | 77 | 1.535 | 27.692 | 50.566 | 0.00 | 0.00 | H |
| ATOM | 755 | HG | SER | A | 77 | 4.140 | 30.103 | 51.109 | 0.00 | 0.00 | H |
| ATOM | 756 | N | PRO | A | 78 | 0.151 | 31.778 | 49.998 | 1.00 | 14.32 | N |
| ATOM | 757 | CA | PRO | A | 78 | -0.362 | 32.607 | 48.906 | 1.00 | 14.95 | C |
| ATOM | 758 | C | PRO | A | 78 | 0.574 | 32.728 | 47.710 | 1.00 | 15.21 | C |
| ATOM | 759 | O | PRO | A | 78 | 0.109 | 32.790 | 46.576 | 1.00 | 20.63 | O |
| ATOM | 760 | CB | PRO | A | 78 | -0.594 | 33.957 | 49.573 | 1.00 | 15.74 | C |
| ATOM | 761 | CG | PRO | A | 78 | 0.309 | 33.944 | 50.759 | 1.00 | 15.85 | C |
| ATOM | 762 | CD | PRO | A | 78 | 0.192 | 32.544 | 51.251 | 1.00 | 18.10 | C |
| ATOM | 763 | N | ASP | A | 79 | 1.882 | 32.698 | 47.956 | 1.00 | 13.60 | N |
| ATOM | 764 | CA | ASP | A | 79 | 2.877 | 32.679 | 46.874 | 1.00 | 19.42 | C |
| ATOM | 765 | C | ASP | A | 79 | 2.616 | 31.548 | 45.877 | 1.00 | 17.87 | C |
| ATOM | 766 | O | ASP | A | 79 | 2.547 | 31.777 | 44.676 | 1.00 | 20.31 | O |
| ATOM | 767 | CB | ASP | A | 79 | 4.305 | 32.510 | 47.424 | 1.00 | 28.97 | C |
| ATOM | 768 | CG | ASP | A | 79 | 4.599 | 33.401 | 48.629 | 1.00 | 37.43 | C |
| ATOM | 769 | OD1 | ASP | A | 79 | 3.792 | 34.306 | 48.939 | 1.00 | 45.91 | O |
| ATOM | 770 | OD2 | ASP | A | 79 | 5.657 | 33.195 | 49.270 | 1.00 | 39.71 | O |
| ATOM | 771 | H | ASP | A | 79 | 2.162 | 32.697 | 48.889 | 0.00 | 0.00 | H |
| ATOM | 772 | N | TYR | A | 80 | 2.442 | 30.335 | 46.392 | 1.00 | 15.45 | N |
| ATOM | 773 | CA | TYR | A | 80 | 2.142 | 29.178 | 45.557 | 1.00 | 12.31 | C |
| ATOM | 774 | C | TYR | A | 80 | 0.657 | 29.033 | 45.227 | 1.00 | 9.68 | C |
| ATOM | 775 | O | TYR | A | 80 | 0.194 | 27.936 | 44.907 | 1.00 | 9.28 | O |
| ATOM | 776 | CB | TYR | A | 80 | 2.611 | 27.897 | 46.234 | 1.00 | 10.17 | C |
| ATOM | 777 | CG | TYR | A | 80 | 4.082 | 27.626 | 46.070 | 1.00 | 9.13 | C |
| ATOM | 778 | CD1 | TYR | A | 80 | 5.022 | 28.600 | 46.373 | 1.00 | 5.08 | C |

Fig 4-14

| | | | | | | | | | |
|---|---|---|---|---|---|---|---|---|---|
| ATOM | 779 | CD2 | TYR A | 80 | 4.536 | 26.347 | 45.781 | 1.00 12.62 | C |
| ATOM | 780 | CE1 | TYR A | 80 | 6.373 | 28.303 | 46.419 | 1.00  6.16 | C |
| ATOM | 781 | CE2 | TYR A | 80 | 5.889 | 26.037 | 45.827 | 1.00 15.72 | C |
| ATOM | 782 | CZ | TYR A | 80 | 6.801 | 27.021 | 46.159 | 1.00 13.97 | C |
| ATOM | 783 | OH | TYR A | 80 | 8.124 | 26.683 | 46.343 | 1.00 19.55 | O |
| ATOM | 784 | H | TYR A | 80 | 2.347 | 30.254 | 47.356 | 0.00  0.00 | H |
| ATOM | 785 | HH | TYR A | 80 | 8.729 | 27.408 | 46.126 | 0.00  0.00 | H |
| ATOM | 786 | N | ALA A | 81 | -0.104 | 30.115 | 45.344 | 1.00  9.06 | N |
| ATOM | 787 | CA | ALA A | 81 | -1.536 | 30.071 | 45.028 | 1.00  8.94 | C |
| ATOM | 788 | C | ALA A | 81 | -1.973 | 31.342 | 44.290 | 1.00 11.59 | C |
| ATOM | 789 | O | ALA A | 81 | -1.507 | 31.630 | 43.192 | 1.00 14.63 | O |
| ATOM | 790 | CB | ALA A | 81 | -2.362 | 29.899 | 46.312 | 1.00 10.95 | C |
| ATOM | 791 | H | ALA A | 81 | 0.347 | 31.010 | 45.423 | 0.00  0.00 | H |
| ATOM | 792 | N | TYR A | 82 | -2.886 | 32.106 | 44.874 | 1.00 13.59 | N |
| ATOM | 793 | CA | TYR A | 82 | -3.462 | 33.239 | 44.147 | 1.00 15.87 | C |
| ATOM | 794 | C | TYR A | 82 | -2.869 | 34.591 | 44.552 | 1.00 15.70 | C |
| ATOM | 795 | O | TYR A | 82 | -3.388 | 35.646 | 44.183 | 1.00 15.54 | O |
| ATOM | 796 | CB | TYR A | 82 | -4.982 | 33.249 | 44.324 | 1.00 15.49 | C |
| ATOM | 797 | CG | TYR A | 82 | -5.676 | 32.084 | 43.658 | 1.00 19.64 | C |
| ATOM | 798 | CD1 | TYR A | 82 | -5.724 | 31.975 | 42.262 | 1.00 19.36 | C |
| ATOM | 799 | CD2 | TYR A | 82 | -6.283 | 31.091 | 44.415 | 1.00 18.02 | C |
| ATOM | 800 | CE1 | TYR A | 82 | -6.357 | 30.904 | 41.648 | 1.00 12.44 | C |
| ATOM | 801 | CE2 | TYR A | 82 | -6.918 | 30.013 | 43.804 | 1.00 16.50 | C |
| ATOM | 802 | CZ | TYR A | 82 | -6.946 | 29.930 | 42.425 | 1.00 12.60 | C |
| ATOM | 803 | OH | TYR A | 82 | -7.546 | 28.871 | 41.800 | 1.00 12.06 | O |
| ATOM | 804 | H | TYR A | 82 | -3.142 | 32.049 | 45.838 | 0.00  0.00 | H |
| ATOM | 805 | HH | TYR A | 82 | -7.818 | 28.255 | 42.478 | 0.00  0.00 | H |
| ATOM | 806 | N | GLY A | 83 | -1.763 | 34.539 | 45.288 | 1.00 17.13 | N |
| ATOM | 807 | CA | GLY A | 83 | -0.972 | 35.719 | 45.566 | 1.00 15.64 | C |
| ATOM | 808 | C | GLY A | 83 | -1.681 | 36.878 | 46.233 | 1.00 20.32 | C |
| ATOM | 809 | O | GLY A | 83 | -2.708 | 36.728 | 46.910 | 1.00 23.74 | O |
| ATOM | 810 | H | GLY A | 83 | -1.475 | 33.662 | 45.571 | 0.00  0.00 | H |
| ATOM | 811 | N | ALA A | 84 | -1.099 | 38.055 | 46.055 | 1.00 19.06 | N |
| ATOM | 812 | CA | ALA A | 84 | -1.639 | 39.270 | 46.628 | 1.00 15.70 | C |
| ATOM | 813 | C | ALA A | 84 | -2.965 | 39.637 | 45.982 | 1.00 13.85 | C |
| ATOM | 814 | O | ALA A | 84 | -3.823 | 40.230 | 46.618 | 1.00 14.46 | O |
| ATOM | 815 | CB | ALA A | 84 | -0.640 | 40.394 | 46.455 | 1.00 19.93 | C |
| ATOM | 816 | H | ALA A | 84 | -0.306 | 38.078 | 45.480 | 0.00  0.00 | H |
| ATOM | 817 | N | THR A | 85 | -3.131 | 39.247 | 44.726 | 1.00 17.88 | N |
| ATOM | 818 | CA | THR A | 85 | -4.308 | 39.623 | 43.934 | 1.00 24.03 | C |
| ATOM | 819 | C | THR A | 85 | -5.537 | 38.787 | 44.254 | 1.00 24.35 | C |
| ATOM | 820 | O | THR A | 85 | -6.660 | 39.189 | 43.954 | 1.00 27.70 | O |
| ATOM | 821 | CB | THR A | 85 | -4.036 | 39.482 | 42.419 | 1.00 21.29 | C |
| ATOM | 822 | OG1 | THR A | 85 | -3.482 | 38.185 | 42.150 | 1.00 28.80 | O |
| ATOM | 823 | CG2 | THR A | 85 | -3.054 | 40.541 | 41.956 | 1.00 16.23 | C |
| ATOM | 824 | H | THR A | 85 | -2.470 | 38.659 | 44.303 | 0.00  0.00 | H |
| ATOM | 825 | HG1 | THR A | 85 | -4.132 | 37.483 | 42.316 | 0.00  0.00 | H |
| ATOM | 826 | N | GLY A | 86 | -5.304 | 37.579 | 44.761 | 1.00 25.09 | N |
| ATOM | 827 | CA | GLY A | 86 | -6.388 | 36.655 | 45.020 | 1.00 19.79 | C |
| ATOM | 828 | C | GLY A | 86 | -7.151 | 36.310 | 43.759 | 1.00 21.57 | C |
| ATOM | 829 | O | GLY A | 86 | -6.589 | 36.200 | 42.659 | 1.00 18.32 | O |
| ATOM | 830 | H | GLY A | 86 | -4.382 | 37.292 | 44.914 | 0.00  0.00 | H |
| ATOM | 831 | N | HIS A | 87 | -8.454 | 36.149 | 43.930 | 1.00 21.72 | N |
| ATOM | 832 | CA | HIS A | 87 | -9.355 | 35.858 | 42.828 | 1.00 24.25 | C |
| ATOM | 833 | C | HIS A | 87 | -10.727 | 36.387 | 43.212 | 1.00 22.13 | C |
| ATOM | 834 | O | HIS A | 87 | -11.356 | 35.891 | 44.152 | 1.00 27.18 | O |
| ATOM | 835 | CB | HIS A | 87 | -9.432 | 34.350 | 42.568 | 1.00 25.61 | C |
| ATOM | 836 | CG | HIS A | 87 | -10.134 | 33.994 | 41.292 | 1.00 29.60 | C |
| ATOM | 837 | ND1 | HIS A | 87 | -9.564 | 34.185 | 40.050 | 1.00 31.39 | N |
| ATOM | 838 | CD2 | HIS A | 87 | -11.360 | 33.466 | 41.064 | 1.00 27.65 | C |

Fig 4-15

```
ATOM    839  CE1 HIS A  87     -10.405  33.783  39.115  1.00 32.76           C
ATOM    840  NE2 HIS A  87     -11.503  33.347  39.703  1.00 30.12           N
ATOM    841  H   HIS A  87      -8.780  36.318  44.827  0.00  0.00           H
ATOM    842  HD1 HIS A  87      -8.690  34.592  39.843  0.00  0.00           H
ATOM    843  HE2 HIS A  87     -12.329  33.167  39.202  0.00  0.00           H
ATOM    844  N   PRO A  88     -11.105  37.531  42.639  1.00 19.63           N
ATOM    845  CA  PRO A  88     -11.989  38.403  43.410  1.00 18.79           C
ATOM    846  C   PRO A  88     -13.399  37.848  43.580  1.00 18.22           C
ATOM    847  O   PRO A  88     -13.974  37.286  42.650  1.00 21.77           O
ATOM    848  CB  PRO A  88     -11.946  39.707  42.626  1.00 18.51           C
ATOM    849  CG  PRO A  88     -10.550  39.713  42.059  1.00 16.30           C
ATOM    850  CD  PRO A  88     -10.357  38.290  41.620  1.00 20.36           C
ATOM    851  N   GLY A  89     -13.851  37.819  44.828  1.00 15.16           N
ATOM    852  CA  GLY A  89     -15.160  37.271  45.120  1.00 12.28           C
ATOM    853  C   GLY A  89     -15.116  35.891  45.749  1.00 13.88           C
ATOM    854  O   GLY A  89     -16.142  35.385  46.211  1.00 13.05           O
ATOM    855  H   GLY A  89     -13.303  38.201  45.539  0.00  0.00           H
ATOM    856  N   ILE A  90     -13.932  35.289  45.812  1.00 12.11           N
ATOM    857  CA  ILE A  90     -13.831  33.928  46.328  1.00 17.75           C
ATOM    858  C   ILE A  90     -12.577  33.670  47.150  1.00 14.47           C
ATOM    859  O   ILE A  90     -12.663  33.134  48.247  1.00 15.69           O
ATOM    860  CB  ILE A  90     -13.950  32.875  45.177  1.00 23.54           C
ATOM    861  CG1 ILE A  90     -13.590  31.478  45.688  1.00 28.28           C
ATOM    862  CG2 ILE A  90     -13.063  33.252  44.007  1.00 24.28           C
ATOM    863  CD1 ILE A  90     -14.036  30.361  44.764  1.00 34.25           C
ATOM    864  H   ILE A  90     -13.164  35.742  45.410  0.00  0.00           H
ATOM    865  N   ILE A  91     -11.416  34.013  46.600  1.00 12.99           N
ATOM    866  CA  ILE A  91     -10.150  33.915  47.328  1.00  9.92           C
ATOM    867  C   ILE A  91      -9.584  35.324  47.520  1.00 15.34           C
ATOM    868  O   ILE A  91      -9.285  36.025  46.539  1.00 13.98           O
ATOM    869  CB  ILE A  91      -9.091  33.085  46.559  1.00  6.38           C
ATOM    870  CG1 ILE A  91      -9.681  31.762  46.041  1.00  4.55           C
ATOM    871  CG2 ILE A  91      -7.873  32.881  47.428  1.00  2.00           C
ATOM    872  CD1 ILE A  91     -10.163  30.821  47.084  1.00  3.68           C
ATOM    873  H   ILE A  91     -11.413  34.380  45.696  0.00  0.00           H
ATOM    874  N   PRO A  92      -9.520  35.797  48.781  1.00 17.29           N
ATOM    875  CA  PRO A  92      -9.007  37.143  49.062  1.00 12.40           C
ATOM    876  C   PRO A  92      -7.492  37.264  48.855  1.00 14.30           C
ATOM    877  O   PRO A  92      -6.815  36.290  48.516  1.00 17.48           O
ATOM    878  CB  PRO A  92      -9.421  37.381  50.514  1.00 10.67           C
ATOM    879  CG  PRO A  92      -9.477  36.019  51.107  1.00 11.96           C
ATOM    880  CD  PRO A  92      -9.964  35.110  50.011  1.00 14.17           C
ATOM    881  N   PRO A  93      -6.966  38.493  48.923  1.00 15.65           N
ATOM    882  CA  PRO A  93      -5.518  38.704  48.833  1.00 16.50           C
ATOM    883  C   PRO A  93      -4.743  37.999  49.933  1.00 16.97           C
ATOM    884  O   PRO A  93      -5.160  37.971  51.090  1.00 20.11           O
ATOM    885  CB  PRO A  93      -5.380  40.217  48.941  1.00 17.10           C
ATOM    886  CG  PRO A  93      -6.629  40.717  48.308  1.00 22.16           C
ATOM    887  CD  PRO A  93      -7.700  39.762  48.785  1.00 18.15           C
ATOM    888  N   HIS A  94      -3.609  37.424  49.563  1.00 15.46           N
ATOM    889  CA  HIS A  94      -2.701  36.830  50.538  1.00 14.40           C
ATOM    890  C   HIS A  94      -3.176  35.531  51.202  1.00 13.30           C
ATOM    891  O   HIS A  94      -2.380  34.843  51.836  1.00 16.61           O
ATOM    892  CB  HIS A  94      -2.366  37.855  51.608  1.00 12.10           C
ATOM    893  CG  HIS A  94      -1.762  39.103  51.061  1.00 15.95           C
ATOM    894  ND1 HIS A  94      -0.455  39.165  50.621  1.00 16.58           N
ATOM    895  CD2 HIS A  94      -2.313  40.308  50.781  1.00 16.10           C
ATOM    896  CE1 HIS A  94      -0.230  40.351  50.086  1.00 20.16           C
ATOM    897  NE2 HIS A  94      -1.342  41.063  50.171  1.00 21.63           N
ATOM    898  H   HIS A  94      -3.476  37.286  48.598  0.00  0.00           H
```

Fig 4-16

```
ATOM    899  HD1 HIS A  94       0.241  38.484  50.761  0.00   0.00           H
ATOM    900  HE2 HIS A  94      -1.470  41.979  49.833  0.00   0.00           H
ATOM    901  N   ALA A  95      -4.403  35.112  50.915  1.00   6.56           N
ATOM    902  CA  ALA A  95      -4.982  33.954  51.576  1.00   7.81           C
ATOM    903  C   ALA A  95      -4.132  32.683  51.516  1.00  10.01           C
ATOM    904  O   ALA A  95      -3.691  32.260  50.456  1.00  10.42           O
ATOM    905  CB  ALA A  95      -6.365  33.676  51.026  1.00   2.72           C
ATOM    906  H   ALA A  95      -4.911  35.568  50.215  0.00   0.00           H
ATOM    907  N   THR A  96      -3.801  32.165  52.691  1.00  12.98           N
ATOM    908  CA  THR A  96      -3.319  30.797  52.831  1.00  12.92           C
ATOM    909  C   THR A  96      -4.501  29.852  52.600  1.00  14.35           C
ATOM    910  O   THR A  96      -5.569  30.025  53.212  1.00  14.86           O
ATOM    911  CB  THR A  96      -2.740  30.568  54.254  1.00   9.93           C
ATOM    912  OG1 THR A  96      -1.655  31.480  54.472  1.00  11.98           O
ATOM    913  CG2 THR A  96      -2.240  29.139  54.430  1.00   3.68           C
ATOM    914  H   THR A  96      -3.847  32.758  53.468  0.00   0.00           H
ATOM    915  HG1 THR A  96      -1.236  31.644  53.620  0.00   0.00           H
ATOM    916  N   LEU A  97      -4.349  28.937  51.642  1.00   8.43           N
ATOM    917  CA  LEU A  97      -5.406  27.976  51.332  1.00   3.80           C
ATOM    918  C   LEU A  97      -5.083  26.557  51.814  1.00   5.71           C
ATOM    919  O   LEU A  97      -3.926  26.123  51.815  1.00   7.74           O
ATOM    920  CB  LEU A  97      -5.672  27.930  49.826  1.00   3.61           C
ATOM    921  CG  LEU A  97      -5.948  29.193  49.011  1.00   6.56           C
ATOM    922  CD1 LEU A  97      -5.831  28.841  47.534  1.00   2.62           C
ATOM    923  CD2 LEU A  97      -7.326  29.758  49.318  1.00   6.52           C
ATOM    924  H   LEU A  97      -3.495  28.902  51.157  0.00   0.00           H
ATOM    925  N   VAL A  98      -6.121  25.814  52.167  1.00   2.33           N
ATOM    926  CA  VAL A  98      -5.968  24.407  52.476  1.00   3.09           C
ATOM    927  C   VAL A  98      -6.801  23.602  51.491  1.00   7.78           C
ATOM    928  O   VAL A  98      -8.012  23.836  51.346  1.00   8.13           O
ATOM    929  CB  VAL A  98      -6.461  24.079  53.900  1.00   4.96           C
ATOM    930  CG1 VAL A  98      -6.144  22.638  54.230  1.00   2.00           C
ATOM    931  CG2 VAL A  98      -5.824  25.011  54.917  1.00   2.00           C
ATOM    932  H   VAL A  98      -7.012  26.221  52.183  0.00   0.00           H
ATOM    933  N   PHE A  99      -6.166  22.622  50.853  1.00   7.58           N
ATOM    934  CA  PHE A  99      -6.877  21.677  49.996  1.00   6.62           C
ATOM    935  C   PHE A  99      -6.849  20.239  50.519  1.00   5.20           C
ATOM    936  O   PHE A  99      -5.796  19.718  50.860  1.00   5.24           O
ATOM    937  CB  PHE A  99      -6.303  21.728  48.578  1.00   2.00           C
ATOM    938  CG  PHE A  99      -6.824  22.873  47.763  1.00   4.66           C
ATOM    939  CD1 PHE A  99      -8.069  22.787  47.138  1.00   2.68           C
ATOM    940  CD2 PHE A  99      -6.115  24.070  47.687  1.00   4.09           C
ATOM    941  CE1 PHE A  99      -8.598  23.874  46.462  1.00   2.00           C
ATOM    942  CE2 PHE A  99      -6.638  25.166  47.008  1.00   2.00           C
ATOM    943  CZ  PHE A  99      -7.879  25.068  46.399  1.00   2.00           C
ATOM    944  H   PHE A  99      -5.202  22.540  50.970  0.00   0.00           H
ATOM    945  N   ASP A 100      -8.014  19.613  50.627  1.00   3.90           N
ATOM    946  CA  ASP A 100      -8.070  18.167  50.830  1.00   7.59           C
ATOM    947  C   ASP A 100      -8.280  17.463  49.482  1.00   9.31           C
ATOM    948  O   ASP A 100      -9.379  17.490  48.934  1.00  10.21           O
ATOM    949  CB  ASP A 100      -9.205  17.817  51.804  1.00   6.95           C
ATOM    950  CG  ASP A 100      -9.424  16.310  51.966  1.00   7.89           C
ATOM    951  OD1 ASP A 100      -8.564  15.494  51.568  1.00  14.35           O
ATOM    952  OD2 ASP A 100     -10.480  15.937  52.511  1.00  12.55           O
ATOM    953  H   ASP A 100      -8.834  20.147  50.593  0.00   0.00           H
ATOM    954  N   VAL A 101      -7.232  16.832  48.954  1.00   9.09           N
ATOM    955  CA  VAL A 101      -7.306  16.202  47.633  1.00  11.24           C
ATOM    956  C   VAL A 101      -6.957  14.711  47.652  1.00  12.17           C
ATOM    957  O   VAL A 101      -5.962  14.296  48.251  1.00  12.83           O
ATOM    958  CB  VAL A 101      -6.417  16.956  46.557  1.00   7.24           C
```

Fig 4-17

```
ATOM    959  CG1 VAL A 101      -6.122   18.380   47.014  1.00   5.62           C
ATOM    960  CG2 VAL A 101      -5.118   16.208   46.278  1.00   3.42           C
ATOM    961  H   VAL A 101      -6.416   16.741   49.499  0.00   0.00           H
ATOM    962  N   GLU A 102      -7.796   13.913   47.001  1.00  11.69           N
ATOM    963  CA  GLU A 102      -7.527   12.490   46.813  1.00  14.51           C
ATOM    964  C   GLU A 102      -7.266   12.132   45.336  1.00  13.17           C
ATOM    965  O   GLU A 102      -8.100   12.392   44.465  1.00  15.41           O
ATOM    966  CB  GLU A 102      -8.697   11.660   47.356  1.00  12.86           C
ATOM    967  CG  GLU A 102      -8.562   10.171   47.074  1.00  18.32           C
ATOM    968  CD  GLU A 102      -9.681    9.340   47.666  1.00  20.79           C
ATOM    969  OE1 GLU A 102     -10.840    9.811   47.715  1.00  26.66           O
ATOM    970  OE2 GLU A 102      -9.402    8.187   48.052  1.00  23.60           O
ATOM    971  H   GLU A 102      -8.591   14.307   46.611  0.00   0.00           H
ATOM    972  N   LEU A 103      -6.147   11.465   45.079  1.00   9.34           N
ATOM    973  CA  LEU A 103      -5.763   11.096   43.722  1.00  13.72           C
ATOM    974  C   LEU A 103      -6.404    9.767   43.302  1.00  15.75           C
ATOM    975  O   LEU A 103      -5.838    8.698   43.511  1.00  16.07           O
ATOM    976  CB  LEU A 103      -4.226   11.024   43.593  1.00   6.09           C
ATOM    977  CG  LEU A 103      -3.643   10.842   42.180  1.00   4.19           C
ATOM    978  CD1 LEU A 103      -4.309   11.807   41.220  1.00   8.95           C
ATOM    979  CD2 LEU A 103      -2.149   11.088   42.180  1.00   3.73           C
ATOM    980  H   LEU A 103      -5.600   11.178   45.846  0.00   0.00           H
ATOM    981  N   LEU A 104      -7.579    9.856   42.685  1.00  18.31           N
ATOM    982  CA  LEU A 104      -8.342    8.680   42.257  1.00  16.33           C
ATOM    983  C   LEU A 104      -7.594    7.786   41.266  1.00  18.03           C
ATOM    984  O   LEU A 104      -7.390    6.599   41.516  1.00  18.22           O
ATOM    985  CB  LEU A 104      -9.664    9.120   41.633  1.00  14.17           C
ATOM    986  CG  LEU A 104     -10.547   10.017   42.500  1.00  14.18           C
ATOM    987  CD1 LEU A 104     -11.838   10.345   41.772  1.00  13.42           C
ATOM    988  CD2 LEU A 104     -10.843    9.307   43.804  1.00  14.17           C
ATOM    989  H   LEU A 104      -7.915   10.758   42.502  0.00   0.00           H
ATOM    990  N   LYS A 105      -7.196    8.360   40.134  1.00  20.74           N
ATOM    991  CA  LYS A 105      -6.510    7.603   39.086  1.00  20.67           C
ATOM    992  C   LYS A 105      -5.692    8.497   38.154  1.00  19.89           C
ATOM    993  O   LYS A 105      -5.948    9.696   38.038  1.00  21.43           O
ATOM    994  CB  LYS A 105      -7.529    6.806   38.263  1.00  24.07           C
ATOM    995  CG  LYS A 105      -8.765    7.605   37.853  1.00  27.58           C
ATOM    996  CD  LYS A 105      -9.733    6.771   37.027  1.00  30.34           C
ATOM    997  CE  LYS A 105     -10.994    7.557   36.684  1.00  34.49           C
ATOM    998  NZ  LYS A 105     -11.853    7.826   37.876  1.00  35.90           N
ATOM    999  H   LYS A 105      -7.343    9.323   40.023  0.00   0.00           H
ATOM   1000  1HZ LYS A 105     -11.317    8.378   38.576  0.00   0.00           H
ATOM   1001  2HZ LYS A 105     -12.690    8.371   37.584  0.00   0.00           H
ATOM   1002  3HZ LYS A 105     -12.151    6.928   38.306  0.00   0.00           H
ATOM   1003  N   LEU A 106      -4.664    7.927   37.545  1.00  22.51           N
ATOM   1004  CA  LEU A 106      -4.015    8.575   36.411  1.00  24.63           C
ATOM   1005  C   LEU A 106      -4.544    8.044   35.076  1.00  27.28           C
ATOM   1006  O   LEU A 106      -4.969    6.887   34.978  1.00  30.28           O
ATOM   1007  CB  LEU A 106      -2.500    8.385   36.469  1.00  20.64           C
ATOM   1008  CG  LEU A 106      -1.709    9.334   37.369  1.00  25.07           C
ATOM   1009  CD1 LEU A 106      -2.201   10.771   37.213  1.00  26.33           C
ATOM   1010  CD2 LEU A 106      -1.853    8.891   38.791  1.00  25.85           C
ATOM   1011  H   LEU A 106      -4.392    7.031   37.820  0.00   0.00           H
ATOM   1012  N   GLU A 107      -4.660    8.946   34.108  1.00  28.70           N
ATOM   1013  CA  GLU A 107      -4.910    8.585   32.718  1.00  28.85           C
ATOM   1014  C   GLU A 107      -4.122    9.520   31.789  1.00  32.85           C
ATOM   1015  O   GLU A 107      -2.875    9.520   31.888  1.00  37.58           O
ATOM   1016  CB  GLU A 107      -6.410    8.650   32.415  1.00  24.83           C
ATOM   1017  CG  GLU A 107      -7.125    9.812   33.068  1.00  28.14           C
ATOM   1018  CD  GLU A 107      -8.428   10.140   32.379  1.00  33.36           C
```

```
Fig 4-18

ATOM   1019  OE1  GLU A 107     -9.439   9.461  32.672  1.00 26.99           O
ATOM   1020  OE2  GLU A 107     -8.433  11.070  31.534  1.00 36.01           O
ATOM   1021  OXT  GLU A 107     -4.739  10.301  31.034  1.00 39.52           O
ATOM   1022  H    GLU A 107     -4.585   9.896  34.325  0.00  0.00           H
TER    1023       GLU A 107
ATOM   1024  N    ARG B2018    -15.291  37.286   7.064  1.00 42.10           N
ATOM   1025  CA   ARG B2018    -15.622  35.859   7.359  1.00 39.30           C
ATOM   1026  C    ARG B2018    -14.580  34.887   6.780  1.00 38.22           C
ATOM   1027  O    ARG B2018    -13.857  35.228   5.840  1.00 36.64           O
ATOM   1028  CB   ARG B2018    -17.032  35.522   6.831  1.00 40.78           C
ATOM   1029  CG   ARG B2018    -18.205  36.058   7.690  1.00 39.26           C
ATOM   1030  CD   ARG B2018    -18.451  35.201   8.947  1.00 39.90           C
ATOM   1031  NE   ARG B2018    -17.238  35.062   9.755  1.00 40.36           N
ATOM   1032  CZ   ARG B2018    -16.466  33.977   9.783  1.00 36.06           C
ATOM   1033  NH1  ARG B2018    -16.931  32.806   9.364  1.00 32.42           N
ATOM   1034  NH2  ARG B2018    -15.238  34.057  10.282  1.00 33.73           N
ATOM   1035 1H    ARG B2018    -15.235  37.392   6.027  0.00  0.00           H
ATOM   1036 2H    ARG B2018    -16.030  37.925   7.426  0.00  0.00           H
ATOM   1037 3H    ARG B2018    -14.365  37.551   7.457  0.00  0.00           H
ATOM   1038  HE   ARG B2018    -16.986  35.810  10.336  0.00  0.00           H
ATOM   1039 1HH1  ARG B2018    -17.868  32.729   9.020  0.00  0.00           H
ATOM   1040 2HH1  ARG B2018    -16.342  31.999   9.380  0.00  0.00           H
ATOM   1041 1HH2  ARG B2018    -14.887  34.922  10.634  0.00  0.00           H
ATOM   1042 2HH2  ARG B2018    -14.676  33.233  10.320  0.00  0.00           H
ATOM   1043  N    VAL B2019    -14.474  33.705   7.388  1.00 36.94           N
ATOM   1044  CA   VAL B2019    -13.432  32.725   7.052  1.00 30.21           C
ATOM   1045  C    VAL B2019    -13.973  31.314   7.273  1.00 24.65           C
ATOM   1046  O    VAL B2019    -14.934  31.123   8.016  1.00 24.40           O
ATOM   1047  CB   VAL B2019    -12.157  32.939   7.942  1.00 32.18           C
ATOM   1048  CG1  VAL B2019    -12.536  32.966   9.417  1.00 26.50           C
ATOM   1049  CG2  VAL B2019    -11.107  31.853   7.679  1.00 32.10           C
ATOM   1050  H    VAL B2019    -15.146  33.399   8.027  0.00  0.00           H
ATOM   1051  N    ALA B2020    -13.355  30.329   6.635  1.00 22.00           N
ATOM   1052  CA   ALA B2020    -13.693  28.930   6.883  1.00 22.59           C
ATOM   1053  C    ALA B2020    -13.000  28.354   8.125  1.00 22.82           C
ATOM   1054  O    ALA B2020    -11.764  28.295   8.199  1.00 19.38           O
ATOM   1055  CB   ALA B2020    -13.356  28.087   5.664  1.00 21.75           C
ATOM   1056  H    ALA B2020    -12.627  30.546   6.016  0.00  0.00           H
ATOM   1057  N    ILE B2021    -13.805  27.988   9.118  1.00 20.69           N
ATOM   1058  CA   ILE B2021    -13.312  27.233  10.266  1.00 18.46           C
ATOM   1059  C    ILE B2021    -14.413  26.367  10.876  1.00 15.19           C
ATOM   1060  O    ILE B2021    -15.580  26.750  10.885  1.00 15.20           O
ATOM   1061  CB   ILE B2021    -12.730  28.173  11.358  1.00 22.76           C
ATOM   1062  CG1  ILE B2021    -12.249  27.351  12.562  1.00 25.06           C
ATOM   1063  CG2  ILE B2021    -13.769  29.208  11.775  1.00 25.54           C
ATOM   1064  CD1  ILE B2021    -11.140  28.005  13.366  1.00 25.45           C
ATOM   1065  H    ILE B2021    -14.741  28.270   9.101  0.00  0.00           H
ATOM   1066  N    LEU B2022    -14.051  25.164  11.303  1.00 12.39           N
ATOM   1067  CA   LEU B2022    -14.967  24.324  12.072  1.00 10.94           C
ATOM   1068  C    LEU B2022    -15.347  24.946  13.414  1.00 11.66           C
ATOM   1069  O    LEU B2022    -14.489  25.468  14.134  1.00 11.57           O
ATOM   1070  CB   LEU B2022    -14.339  22.958  12.314  1.00  4.40           C
ATOM   1071  CG   LEU B2022    -14.001  22.196  11.041  1.00  3.20           C
ATOM   1072  CD1  LEU B2022    -13.224  20.961  11.400  1.00  2.00           C
ATOM   1073  CD2  LEU B2022    -15.279  21.845  10.295  1.00  2.00           C
ATOM   1074  H    LEU B2022    -13.191  24.841  10.981  0.00  0.00           H
ATOM   1075  N    TRP B2023    -16.628  24.838  13.766  1.00 11.70           N
ATOM   1076  CA   TRP B2023    -17.128  25.262  15.079  1.00 13.42           C
ATOM   1077  C    TRP B2023    -16.359  24.603  16.230  1.00 14.99           C
ATOM   1078  O    TRP B2023    -16.174  25.189  17.292  1.00 20.57           O
```

Fig 4-19

```
ATOM   1079  CB   TRP B2023     -18.624  24.943  15.192  1.00  6.83           C
ATOM   1080  CG   TRP B2023     -19.499  25.971  14.562  1.00  2.00           C
ATOM   1081  CD1  TRP B2023     -19.093  27.063  13.854  1.00  2.00           C
ATOM   1082  CD2  TRP B2023     -20.927  26.075  14.671  1.00  2.00           C
ATOM   1083  NE1  TRP B2023     -20.169  27.839  13.525  1.00  2.00           N
ATOM   1084  CE2  TRP B2023     -21.309  27.257  14.015  1.00  2.00           C
ATOM   1085  CE3  TRP B2023     -21.917  25.288  15.267  1.00  2.00           C
ATOM   1086  CZ2  TRP B2023     -22.640  27.672  13.937  1.00  2.00           C
ATOM   1087  CZ3  TRP B2023     -23.241  25.706  15.188  1.00  2.00           C
ATOM   1088  CH2  TRP B2023     -23.585  26.881  14.528  1.00  2.00           C
ATOM   1089  H    TRP B2023     -17.279  24.666  13.058  0.00  0.00           H
ATOM   1090  HE1  TRP B2023     -20.112  28.705  13.064  0.00  0.00           H
ATOM   1091  N    HIS B2024     -15.921  23.373  15.999  1.00 17.48           N
ATOM   1092  CA   HIS B2024     -14.969  22.689  16.871  1.00 19.39           C
ATOM   1093  C    HIS B2024     -13.728  23.558  17.158  1.00 19.84           C
ATOM   1094  O    HIS B2024     -13.541  24.012  18.280  1.00 22.62           O
ATOM   1095  CB   HIS B2024     -14.560  21.346  16.234  1.00 25.50           C
ATOM   1096  CG   HIS B2024     -15.693  20.627  15.555  1.00 33.39           C
ATOM   1097  ND1  HIS B2024     -16.571  19.807  16.233  1.00 41.22           N
ATOM   1098  CD2  HIS B2024     -16.181  20.726  14.293  1.00 33.72           C
ATOM   1099  CE1  HIS B2024     -17.559  19.450  15.429  1.00 38.35           C
ATOM   1100  NE2  HIS B2024     -17.347  19.999  14.248  1.00 38.10           N
ATOM   1101  H    HIS B2024     -16.377  22.943  15.254  0.00  0.00           H
ATOM   1102  HD1  HIS B2024     -16.490  19.465  17.152  0.00  0.00           H
ATOM   1103  HE2  HIS B2024     -17.975  19.937  13.490  0.00  0.00           H
ATOM   1104  N    GLU B2025     -12.963  23.906  16.127  1.00 20.21           N
ATOM   1105  CA   GLU B2025     -11.732  24.686  16.318  1.00 20.43           C
ATOM   1106  C    GLU B2025     -12.037  26.074  16.875  1.00 17.30           C
ATOM   1107  O    GLU B2025     -11.268  26.641  17.651  1.00 15.80           O
ATOM   1108  CB   GLU B2025     -10.969  24.846  14.994  1.00 27.02           C
ATOM   1109  CG   GLU B2025     -10.961  23.614  14.089  1.00 41.60           C
ATOM   1110  CD   GLU B2025     -10.550  23.937  12.652  1.00 47.27           C
ATOM   1111  OE1  GLU B2025      -9.330  23.903  12.369  1.00 54.42           O
ATOM   1112  OE2  GLU B2025     -11.440  24.219  11.810  1.00 37.45           O
ATOM   1113  H    GLU B2025     -13.279  23.712  15.223  0.00  0.00           H
ATOM   1114  N    MET B2026     -13.159  26.625  16.444  1.00 15.93           N
ATOM   1115  CA   MET B2026     -13.552  27.971  16.816  1.00 18.01           C
ATOM   1116  C    MET B2026     -13.805  28.060  18.325  1.00 18.72           C
ATOM   1117  O    MET B2026     -13.257  28.927  19.012  1.00 18.88           O
ATOM   1118  CB   MET B2026     -14.806  28.354  16.021  1.00 21.46           C
ATOM   1119  CG   MET B2026     -15.619  29.490  16.603  1.00 28.72           C
ATOM   1120  SD   MET B2026     -16.931  30.032  15.505  1.00 34.40           S
ATOM   1121  CE   MET B2026     -15.938  30.642  14.095  1.00 36.70           C
ATOM   1122  H    MET B2026     -13.715  26.119  15.820  0.00  0.00           H
ATOM   1123  N    TRP B2027     -14.553  27.092  18.845  1.00 18.28           N
ATOM   1124  CA   TRP B2027     -14.890  27.047  20.263  1.00 16.52           C
ATOM   1125  C    TRP B2027     -13.736  26.609  21.159  1.00 15.61           C
ATOM   1126  O    TRP B2027     -13.561  27.129  22.254  1.00 18.72           O
ATOM   1127  CB   TRP B2027     -16.087  26.129  20.481  1.00 14.68           C
ATOM   1128  CG   TRP B2027     -17.381  26.861  20.453  1.00 16.26           C
ATOM   1129  CD1  TRP B2027     -18.322  26.831  19.466  1.00 16.17           C
ATOM   1130  CD2  TRP B2027     -17.870  27.760  21.450  1.00 16.49           C
ATOM   1131  NE1  TRP B2027     -19.370  27.656  19.789  1.00 13.89           N
ATOM   1132  CE2  TRP B2027     -19.120  28.239  21.003  1.00 15.26           C
ATOM   1133  CE3  TRP B2027     -17.373  28.214  22.681  1.00 18.70           C
ATOM   1134  CZ2  TRP B2027     -19.886  29.142  21.745  1.00 17.88           C
ATOM   1135  CZ3  TRP B2027     -18.133  29.114  23.421  1.00 17.25           C
ATOM   1136  CH2  TRP B2027     -19.376  29.565  22.950  1.00 21.47           C
ATOM   1137  H    TRP B2027     -14.929  26.414  18.243  0.00  0.00           H
ATOM   1138  HE1  TRP B2027     -20.150  27.816  19.215  0.00  0.00           H
```

Fig 4-20

```
ATOM   1139  N    HIS B2028     -12.906  25.702  20.665  1.00 11.04           N
ATOM   1140  CA   HIS B2028     -11.735  25.275  21.412  1.00 10.15           C
ATOM   1141  C    HIS B2028     -10.827  26.424  21.805  1.00 10.27           C
ATOM   1142  O    HIS B2028     -10.401  26.519  22.941  1.00 10.19           O
ATOM   1143  CB   HIS B2028     -10.920  24.282  20.604  1.00  9.23           C
ATOM   1144  CG   HIS B2028      -9.821  23.642  21.389  1.00 10.39           C
ATOM   1145  ND1  HIS B2028      -8.575  24.215  21.529  1.00 13.26           N
ATOM   1146  CD2  HIS B2028      -9.786  22.484  22.091  1.00  8.51           C
ATOM   1147  CE1  HIS B2028      -7.814  23.433  22.276  1.00 15.69           C
ATOM   1148  NE2  HIS B2028      -8.527  22.377  22.629  1.00 18.29           N
ATOM   1149  H    HIS B2028     -13.152  25.290  19.807  0.00  0.00           H
ATOM   1150  HD1  HIS B2028      -8.284  25.084  21.180  0.00  0.00           H
ATOM   1151  HE2  HIS B2028      -8.221  21.579  23.119  0.00  0.00           H
ATOM   1152  N    GLU B2029     -10.360  27.167  20.817  1.00 19.72           N
ATOM   1153  CA   GLU B2029      -9.433  28.257  21.093  1.00 27.56           C
ATOM   1154  C    GLU B2029     -10.133  29.508  21.642  1.00 27.45           C
ATOM   1155  O    GLU B2029      -9.533  30.277  22.392  1.00 29.68           O
ATOM   1156  CB   GLU B2029      -8.601  28.592  19.843  1.00 34.06           C
ATOM   1157  CG   GLU B2029      -9.401  28.822  18.565  1.00 44.39           C
ATOM   1158  CD   GLU B2029      -8.554  28.678  17.307  1.00 50.63           C
ATOM   1159  OE1  GLU B2029      -7.828  27.664  17.191  1.00 51.32           O
ATOM   1160  OE2  GLU B2029      -8.624  29.570  16.429  1.00 54.55           O
ATOM   1161  H    GLU B2029     -10.688  27.017  19.900  0.00  0.00           H
ATOM   1162  N    GLY B2030     -11.433  29.634  21.380  1.00 25.66           N
ATOM   1163  CA   GLY B2030     -12.214  30.696  21.997  1.00 21.35           C
ATOM   1164  C    GLY B2030     -12.307  30.538  23.504  1.00 16.02           C
ATOM   1165  O    GLY B2030     -11.837  31.390  24.257  1.00 17.01           O
ATOM   1166  H    GLY B2030     -11.843  29.093  20.670  0.00  0.00           H
ATOM   1167  N    LEU B2031     -12.767  29.368  23.932  1.00 11.25           N
ATOM   1168  CA   LEU B2031     -12.805  29.012  25.341  1.00  6.54           C
ATOM   1169  C    LEU B2031     -11.441  29.088  26.024  1.00 10.09           C
ATOM   1170  O    LEU B2031     -11.337  29.538  27.168  1.00 16.95           O
ATOM   1171  CB   LEU B2031     -13.382  27.612  25.511  1.00  2.00           C
ATOM   1172  CG   LEU B2031     -14.869  27.475  25.192  1.00  2.25           C
ATOM   1173  CD1  LEU B2031     -15.347  26.079  25.568  1.00  2.00           C
ATOM   1174  CD2  LEU B2031     -15.656  28.530  25.936  1.00  2.00           C
ATOM   1175  H    LEU B2031     -13.130  28.749  23.264  0.00  0.00           H
ATOM   1176  N    GLU B2032     -10.386  28.657  25.348  1.00  8.34           N
ATOM   1177  CA   GLU B2032      -9.068  28.756  25.957  1.00 12.37           C
ATOM   1178  C    GLU B2032      -8.629  30.210  26.154  1.00 12.81           C
ATOM   1179  O    GLU B2032      -8.263  30.588  27.261  1.00 21.81           O
ATOM   1180  CB   GLU B2032      -8.028  27.986  25.146  1.00 16.26           C
ATOM   1181  CG   GLU B2032      -6.692  27.831  25.861  1.00 23.62           C
ATOM   1182  CD   GLU B2032      -5.792  26.772  25.235  1.00 30.03           C
ATOM   1183  OE1  GLU B2032      -6.241  25.611  25.078  1.00 32.01           O
ATOM   1184  OE2  GLU B2032      -4.617  27.092  24.948  1.00 31.98           O
ATOM   1185  H    GLU B2032     -10.522  28.216  24.483  0.00  0.00           H
ATOM   1186  N    GLU B2033      -8.837  31.053  25.147  1.00 11.47           N
ATOM   1187  CA   GLU B2033      -8.462  32.473  25.225  1.00 12.69           C
ATOM   1188  C    GLU B2033      -9.308  33.226  26.254  1.00 10.31           C
ATOM   1189  O    GLU B2033      -8.808  34.068  26.994  1.00  6.92           O
ATOM   1190  CB   GLU B2033      -8.631  33.140  23.854  1.00 19.44           C
ATOM   1191  CG   GLU B2033      -7.834  34.437  23.650  1.00 30.82           C
ATOM   1192  CD   GLU B2033      -8.155  35.152  22.319  1.00 42.12           C
ATOM   1193  OE1  GLU B2033      -8.759  34.530  21.408  1.00 39.63           O
ATOM   1194  OE2  GLU B2033      -7.793  36.346  22.186  1.00 44.44           O
ATOM   1195  H    GLU B2033      -9.243  30.710  24.323  0.00  0.00           H
ATOM   1196  N    ALA B2034     -10.600  32.933  26.275  1.00  6.18           N
ATOM   1197  CA   ALA B2034     -11.509  33.572  27.205  1.00  2.76           C
ATOM   1198  C    ALA B2034     -11.101  33.257  28.641  1.00  6.07           C
```

Fig 4-21

```
ATOM   1199  O    ALA B2034     -10.907  34.157  29.453  1.00 11.33           O
ATOM   1200  CB   ALA B2034     -12.920  33.101  26.943  1.00  2.50           C
ATOM   1201  H    ALA B2034     -10.945  32.334  25.587  0.00  0.00           H
ATOM   1202  N    SER B2035     -10.811  31.988  28.903  1.00  8.47           N
ATOM   1203  CA   SER B2035     -10.482  31.543  30.250  1.00  4.56           C
ATOM   1204  C    SER B2035      -9.201  32.193  30.749  1.00  5.40           C
ATOM   1205  O    SER B2035      -9.171  32.734  31.846  1.00 11.51           O
ATOM   1206  CB   SER B2035     -10.357  30.016  30.294  1.00  2.00           C
ATOM   1207  OG   SER B2035      -9.012  29.595  30.200  1.00  7.26           O
ATOM   1208  H    SER B2035     -10.871  31.330  28.175  0.00  0.00           H
ATOM   1209  HG   SER B2035      -8.700  29.696  29.288  0.00  0.00           H
ATOM   1210  N    ARG B2036      -8.195  32.265  29.886  1.00  3.96           N
ATOM   1211  CA   ARG B2036      -6.934  32.909  30.233  1.00  6.68           C
ATOM   1212  C    ARG B2036      -7.110  34.382  30.624  1.00  9.31           C
ATOM   1213  O    ARG B2036      -6.463  34.872  31.548  1.00 12.91           O
ATOM   1214  CB   ARG B2036      -5.959  32.792  29.065  1.00  7.24           C
ATOM   1215  CG   ARG B2036      -4.695  33.631  29.210  1.00 17.54           C
ATOM   1216  CD   ARG B2036      -4.229  34.185  27.860  1.00 17.93           C
ATOM   1217  NE   ARG B2036      -3.637  35.515  27.997  1.00 18.57           N
ATOM   1218  CZ   ARG B2036      -4.055  36.595  27.344  1.00 20.32           C
ATOM   1219  NH1  ARG B2036      -5.080  36.518  26.505  1.00 20.76           N
ATOM   1220  NH2  ARG B2036      -3.456  37.762  27.540  1.00 24.32           N
ATOM   1221  H    ARG B2036      -8.314  31.862  28.998  0.00  0.00           H
ATOM   1222  HE   ARG B2036      -2.897  35.626  28.628  0.00  0.00           H
ATOM   1223  1HH1 ARG B2036      -5.564  35.653  26.375  0.00  0.00           H
ATOM   1224  2HH1 ARG B2036      -5.391  37.341  26.030  0.00  0.00           H
ATOM   1225  1HH2 ARG B2036      -2.689  37.827  28.180  0.00  0.00           H
ATOM   1226  2HH2 ARG B2036      -3.766  38.572  27.045  0.00  0.00           H
ATOM   1227  N    LEU B2037      -8.041  35.057  29.964  1.00 10.78           N
ATOM   1228  CA   LEU B2037      -8.309  36.466  30.214  1.00  8.83           C
ATOM   1229  C    LEU B2037      -9.004  36.692  31.543  1.00 12.66           C
ATOM   1230  O    LEU B2037      -8.626  37.583  32.295  1.00 17.85           O
ATOM   1231  CB   LEU B2037      -9.163  37.034  29.084  1.00  9.75           C
ATOM   1232  CG   LEU B2037      -8.302  37.375  27.873  1.00  8.95           C
ATOM   1233  CD1  LEU B2037      -9.130  37.388  26.613  1.00 11.32           C
ATOM   1234  CD2  LEU B2037      -7.624  38.713  28.110  1.00  7.83           C
ATOM   1235  H    LEU B2037      -8.541  34.590  29.261  0.00  0.00           H
ATOM   1236  N    TYR B2038     -10.020  35.886  31.832  1.00 11.90           N
ATOM   1237  CA   TYR B2038     -10.693  35.930  33.132  1.00 11.68           C
ATOM   1238  C    TYR B2038      -9.811  35.403  34.277  1.00 13.86           C
ATOM   1239  O    TYR B2038      -9.408  36.164  35.158  1.00 17.65           O
ATOM   1240  CB   TYR B2038     -12.006  35.138  33.071  1.00  9.29           C
ATOM   1241  CG   TYR B2038     -12.761  35.090  34.375  1.00 12.17           C
ATOM   1242  CD1  TYR B2038     -12.942  36.239  35.143  1.00 10.58           C
ATOM   1243  CD2  TYR B2038     -13.230  33.880  34.884  1.00 17.46           C
ATOM   1244  CE1  TYR B2038     -13.555  36.181  36.391  1.00 17.63           C
ATOM   1245  CE2  TYR B2038     -13.850  33.810  36.131  1.00 17.47           C
ATOM   1246  CZ   TYR B2038     -14.006  34.962  36.880  1.00 18.99           C
ATOM   1247  OH   TYR B2038     -14.596  34.893  38.123  1.00 22.39           O
ATOM   1248  H    TYR B2038     -10.327  35.266  31.130  0.00  0.00           H
ATOM   1249  HH   TYR B2038     -15.321  34.267  38.078  0.00  0.00           H
ATOM   1250  N    PHE B2039      -9.481  34.113  34.235  1.00 13.85           N
ATOM   1251  CA   PHE B2039      -8.717  33.455  35.299  1.00 10.83           C
ATOM   1252  C    PHE B2039      -7.306  33.980  35.460  1.00 14.37           C
ATOM   1253  O    PHE B2039      -6.861  34.248  36.579  1.00 15.23           O
ATOM   1254  CB   PHE B2039      -8.665  31.950  35.054  1.00  2.58           C
ATOM   1255  CG   PHE B2039      -9.988  31.281  35.235  1.00  6.64           C
ATOM   1256  CD1  PHE B2039     -10.540  31.147  36.510  1.00  4.84           C
ATOM   1257  CD2  PHE B2039     -10.745  30.902  34.131  1.00  2.79           C
ATOM   1258  CE1  PHE B2039     -11.828  30.656  36.680  1.00  5.26           C
```

Fig 4-22

```
ATOM   1259  CE2 PHE B2039     -12.039  30.408  34.292  1.00  2.18      C
ATOM   1260  CZ  PHE B2039     -12.581  30.287  35.563  1.00  4.94      C
ATOM   1261  H   PHE B2039      -9.764  33.595  33.452  0.00  0.00      H
ATOM   1262  N   GLY B2040      -6.619  34.155  34.336  1.00 17.70      N
ATOM   1263  CA  GLY B2040      -5.221  34.544  34.369  1.00 19.07      C
ATOM   1264  C   GLY B2040      -4.954  36.026  34.561  1.00 19.43      C
ATOM   1265  O   GLY B2040      -3.957  36.384  35.180  1.00 24.65      O
ATOM   1266  H   GLY B2040      -7.060  34.013  33.471  0.00  0.00      H
ATOM   1267  N   GLU B2041      -5.815  36.881  34.012  1.00 17.18      N
ATOM   1268  CA  GLU B2041      -5.590  38.328  34.019  1.00 16.74      C
ATOM   1269  C   GLU B2041      -6.689  39.108  34.733  1.00 16.00      C
ATOM   1270  O   GLU B2041      -6.754  40.330  34.629  1.00 16.19      O
ATOM   1271  CB  GLU B2041      -5.476  38.867  32.589  1.00 21.26      C
ATOM   1272  CG  GLU B2041      -5.030  37.856  31.544  1.00 34.57      C
ATOM   1273  CD  GLU B2041      -3.792  38.302  30.785  1.00 39.88      C
ATOM   1274  OE1 GLU B2041      -3.772  39.459  30.303  1.00 41.61      O
ATOM   1275  OE2 GLU B2041      -2.844  37.489  30.664  1.00 43.16      O
ATOM   1276  H   GLU B2041      -6.555  36.502  33.494  0.00  0.00      H
ATOM   1277  N   ARG B2042      -7.626  38.392  35.340  1.00 16.54      N
ATOM   1278  CA  ARG B2042      -8.785  39.011  35.974  1.00 17.30      C
ATOM   1279  C   ARG B2042      -9.485  40.015  35.074  1.00 15.46      C
ATOM   1280  O   ARG B2042     -10.031  41.009  35.550  1.00 17.81      O
ATOM   1281  CB  ARG B2042      -8.389  39.691  37.283  1.00 21.74      C
ATOM   1282  CG  ARG B2042      -8.704  38.869  38.515  1.00 29.43      C
ATOM   1283  CD  ARG B2042      -7.650  37.815  38.736  1.00 31.60      C
ATOM   1284  NE  ARG B2042      -6.318  38.396  38.627  1.00 34.93      N
ATOM   1285  CZ  ARG B2042      -5.273  38.026  39.358  1.00 41.93      C
ATOM   1286  NH1 ARG B2042      -5.398  37.089  40.296  1.00 42.95      N
ATOM   1287  NH2 ARG B2042      -4.097  38.606  39.146  1.00 43.89      N
ATOM   1288  H   ARG B2042      -7.540  37.419  35.364  0.00  0.00      H
ATOM   1289  HE  ARG B2042      -6.148  39.074  37.940  0.00  0.00      H
ATOM   1290 1HH1 ARG B2042      -6.289  36.673  40.485  0.00  0.00      H
ATOM   1291 2HH1 ARG B2042      -4.609  36.857  40.865  0.00  0.00      H
ATOM   1292 1HH2 ARG B2042      -4.011  39.312  38.444  0.00  0.00      H
ATOM   1293 2HH2 ARG B2042      -3.309  38.359  39.710  0.00  0.00      H
ATOM   1294  N   ASN B2043      -9.560  39.689  33.789  1.00 13.57      N
ATOM   1295  CA  ASN B2043     -10.219  40.545  32.805  1.00 12.63      C
ATOM   1296  C   ASN B2043     -11.589  39.985  32.399  1.00 11.08      C
ATOM   1297  O   ASN B2043     -11.704  39.254  31.410  1.00 15.73      O
ATOM   1298  CB  ASN B2043      -9.322  40.702  31.567  1.00  9.40      C
ATOM   1299  CG  ASN B2043      -9.673  41.928  30.734  1.00 13.89      C
ATOM   1300  OD1 ASN B2043     -10.778  42.457  30.805  1.00 13.79      O
ATOM   1301  ND2 ASN B2043      -8.725  42.382  29.941  1.00 19.98      N
ATOM   1302  H   ASN B2043      -9.152  38.845  33.525  0.00  0.00      H
ATOM   1303 1HD2 ASN B2043      -8.951  43.171  29.415  0.00  0.00      H
ATOM   1304 2HD2 ASN B2043      -7.861  41.929  29.933  0.00  0.00      H
ATOM   1305  N   VAL B2044     -12.622  40.329  33.164  1.00  7.83      N
ATOM   1306  CA  VAL B2044     -13.996  39.930  32.841  1.00  8.89      C
ATOM   1307  C   VAL B2044     -14.599  40.724  31.680  1.00 12.31      C
ATOM   1308  O   VAL B2044     -15.607  40.328  31.111  1.00 16.97      O
ATOM   1309  CB  VAL B2044     -14.942  40.079  34.049  1.00  4.93      C
ATOM   1310  CG1 VAL B2044     -16.254  39.343  33.783  1.00  2.00      C
ATOM   1311  CG2 VAL B2044     -14.280  39.541  35.300  1.00  6.55      C
ATOM   1312  H   VAL B2044     -12.407  40.817  33.986  0.00  0.00      H
ATOM   1313  N   LYS B2045     -14.013  41.873  31.366  1.00 15.26      N
ATOM   1314  CA  LYS B2045     -14.387  42.614  30.158  1.00 18.66      C
ATOM   1315  C   LYS B2045     -13.912  41.880  28.890  1.00 15.74      C
ATOM   1316  O   LYS B2045     -14.697  41.616  27.982  1.00 15.10      O
ATOM   1317  CB  LYS B2045     -13.791  44.027  30.205  1.00 20.39      C
ATOM   1318  CG  LYS B2045     -13.868  44.787  28.894  1.00 27.87      C
```

Fig 4-23

```
ATOM   1319  CD   LYS B2045     -12.848  45.913  28.846  1.00 36.04           C
ATOM   1320  CE   LYS B2045     -13.013  46.763  27.592  1.00 39.79           C
ATOM   1321  NZ   LYS B2045     -12.203  48.015  27.646  1.00 42.34           N
ATOM   1322  H    LYS B2045     -13.326  42.230  31.961  0.00  0.00           H
ATOM   1323 1HZ   LYS B2045     -12.477  48.555  28.491  0.00  0.00           H
ATOM   1324 2HZ   LYS B2045     -11.194  47.773  27.696  0.00  0.00           H
ATOM   1325 3HZ   LYS B2045     -12.387  48.579  26.791  0.00  0.00           H
ATOM   1326  N    GLY B2046     -12.640  41.493  28.885  1.00 13.71           N
ATOM   1327  CA   GLY B2046     -12.063  40.767  27.768  1.00 11.16           C
ATOM   1328  C    GLY B2046     -12.716  39.427  27.486  1.00 11.68           C
ATOM   1329  O    GLY B2046     -13.079  39.138  26.350  1.00 12.25           O
ATOM   1330  H    GLY B2046     -12.091  41.759  29.647  0.00  0.00           H
ATOM   1331  N    MET B2047     -12.944  38.632  28.522  1.00 14.02           N
ATOM   1332  CA   MET B2047     -13.555  37.327  28.317  1.00 12.90           C
ATOM   1333  C    MET B2047     -14.954  37.413  27.691  1.00 14.99           C
ATOM   1334  O    MET B2047     -15.275  36.624  26.816  1.00 20.34           O
ATOM   1335  CB   MET B2047     -13.571  36.520  29.625  1.00  9.26           C
ATOM   1336  CG   MET B2047     -14.762  36.725  30.521  1.00  6.02           C
ATOM   1337  SD   MET B2047     -15.175  35.189  31.335  1.00  6.46           S
ATOM   1338  CE   MET B2047     -16.865  35.461  31.714  1.00  4.80           C
ATOM   1339  H    MET B2047     -12.639  38.911  29.412  0.00  0.00           H
ATOM   1340  N    PHE B2048     -15.710  38.465  28.001  1.00 13.61           N
ATOM   1341  CA   PHE B2048     -16.992  38.707  27.324  1.00 12.00           C
ATOM   1342  C    PHE B2048     -16.785  39.054  25.839  1.00 11.47           C
ATOM   1343  O    PHE B2048     -17.540  38.619  24.968  1.00  9.57           O
ATOM   1344  CB   PHE B2048     -17.754  39.849  28.012  1.00 15.37           C
ATOM   1345  CG   PHE B2048     -18.356  39.479  29.357  1.00 19.64           C
ATOM   1346  CD1  PHE B2048     -18.849  38.201  29.600  1.00 20.36           C
ATOM   1347  CD2  PHE B2048     -18.506  40.442  30.352  1.00 17.04           C
ATOM   1348  CE1  PHE B2048     -19.481  37.901  30.806  1.00 12.14           C
ATOM   1349  CE2  PHE B2048     -19.137  40.138  31.552  1.00  7.86           C
ATOM   1350  CZ   PHE B2048     -19.623  38.875  31.774  1.00  2.66           C
ATOM   1351  H    PHE B2048     -15.410  39.078  28.703  0.00  0.00           H
ATOM   1352  N    GLU B2049     -15.754  39.843  25.558  1.00 10.97           N
ATOM   1353  CA   GLU B2049     -15.368  40.161  24.189  1.00 12.08           C
ATOM   1354  C    GLU B2049     -15.072  38.890  23.387  1.00 10.88           C
ATOM   1355  O    GLU B2049     -15.771  38.579  22.427  1.00 12.08           O
ATOM   1356  CB   GLU B2049     -14.144  41.090  24.187  1.00 18.49           C
ATOM   1357  CG   GLU B2049     -14.432  42.512  24.700  1.00 28.61           C
ATOM   1358  CD   GLU B2049     -13.244  43.464  24.566  1.00 32.92           C
ATOM   1359  OE1  GLU B2049     -12.598  43.492  23.489  1.00 32.94           O
ATOM   1360  OE2  GLU B2049     -13.006  44.240  25.521  1.00 34.23           O
ATOM   1361  H    GLU B2049     -15.274  40.244  26.315  0.00  0.00           H
ATOM   1362  N    VAL B2050     -14.120  38.096  23.862  1.00 10.17           N
ATOM   1363  CA   VAL B2050     -13.800  36.807  23.247  1.00 10.01           C
ATOM   1364  C    VAL B2050     -14.693  35.680  23.781  1.00 14.92           C
ATOM   1365  O    VAL B2050     -14.244  34.799  24.529  1.00 20.63           O
ATOM   1366  CB   VAL B2050     -12.318  36.446  23.457  1.00  6.62           C
ATOM   1367  CG1  VAL B2050     -11.942  36.639  24.901  1.00 11.08           C
ATOM   1368  CG2  VAL B2050     -12.039  35.006  22.995  1.00 11.04           C
ATOM   1369  H    VAL B2050     -13.667  38.388  24.675  0.00  0.00           H
ATOM   1370  N    LEU B2051     -15.981  35.775  23.454  1.00 12.19           N
ATOM   1371  CA   LEU B2051     -16.971  34.764  23.816  1.00  9.54           C
ATOM   1372  C    LEU B2051     -18.310  35.117  23.188  1.00 10.79           C
ATOM   1373  O    LEU B2051     -19.052  34.237  22.752  1.00 14.03           O
ATOM   1374  CB   LEU B2051     -17.122  34.686  25.336  1.00  8.37           C
ATOM   1375  CG   LEU B2051     -17.216  33.329  26.046  1.00  8.86           C
ATOM   1376  CD1  LEU B2051     -16.110  32.395  25.592  1.00  5.79           C
ATOM   1377  CD2  LEU B2051     -17.118  33.550  27.538  1.00  2.00           C
ATOM   1378  H    LEU B2051     -16.263  36.655  23.111  0.00  0.00           H
```

Fig 4-24

```
ATOM   1379  N   GLU B2052     -18.562  36.413  23.042  1.00 11.63           N
ATOM   1380  CA  GLU B2052     -19.837  36.897  22.525  1.00 13.53           C
ATOM   1381  C   GLU B2052     -20.059  36.587  21.044  1.00  9.88           C
ATOM   1382  O   GLU B2052     -21.045  35.948  20.693  1.00 11.10           O
ATOM   1383  CB  GLU B2052     -19.980  38.399  22.792  1.00 18.53           C
ATOM   1384  CG  GLU B2052     -21.396  38.835  23.103  1.00 29.17           C
ATOM   1385  CD  GLU B2052     -21.530  40.343  23.220  1.00 34.41           C
ATOM   1386  OE1 GLU B2052     -20.605  40.987  23.766  1.00 36.83           O
ATOM   1387  OE2 GLU B2052     -22.567  40.884  22.772  1.00 39.61           O
ATOM   1388  H   GLU B2052     -17.932  37.078  23.408  0.00  0.00           H
ATOM   1389  N   PRO B2053     -19.085  36.922  20.175  1.00  9.83           N
ATOM   1390  CA  PRO B2053     -18.978  36.374  18.814  1.00  9.97           C
ATOM   1391  C   PRO B2053     -19.301  34.882  18.639  1.00 11.69           C
ATOM   1392  O   PRO B2053     -20.157  34.520  17.837  1.00 15.54           O
ATOM   1393  CB  PRO B2053     -17.537  36.674  18.444  1.00 12.18           C
ATOM   1394  CG  PRO B2053     -17.265  37.981  19.139  1.00 11.41           C
ATOM   1395  CD  PRO B2053     -18.104  38.004  20.386  1.00  7.70           C
ATOM   1396  N   LEU B2054     -18.588  34.021  19.362  1.00 12.26           N
ATOM   1397  CA  LEU B2054     -18.813  32.574  19.304  1.00  7.01           C
ATOM   1398  C   LEU B2054     -20.267  32.247  19.621  1.00  6.82           C
ATOM   1399  O   LEU B2054     -20.928  31.510  18.895  1.00  7.84           O
ATOM   1400  CB  LEU B2054     -17.897  31.859  20.296  1.00  2.00           C
ATOM   1401  CG  LEU B2054     -16.431  32.303  20.307  1.00  2.00           C
ATOM   1402  CD1 LEU B2054     -15.603  31.503  21.299  1.00  2.00           C
ATOM   1403  CD2 LEU B2054     -15.873  32.146  18.921  1.00 12.00           C
ATOM   1404  H   LEU B2054     -17.894  34.386  19.944  0.00  0.00           H
ATOM   1405  N   HIS B2055     -20.805  32.908  20.632  1.00  4.28           N
ATOM   1406  CA  HIS B2055     -22.205  32.716  20.965  1.00  5.58           C
ATOM   1407  C   HIS B2055     -23.118  33.276  19.884  1.00  8.31           C
ATOM   1408  O   HIS B2055     -24.215  32.765  19.667  1.00 14.91           O
ATOM   1409  CB  HIS B2055     -22.533  33.366  22.310  1.00  5.95           C
ATOM   1410  CG  HIS B2055     -22.237  32.495  23.491  1.00  2.00           C
ATOM   1411  ND1 HIS B2055     -23.118  31.542  23.952  1.00  2.00           N
ATOM   1412  CD2 HIS B2055     -21.136  32.399  24.270  1.00  2.00           C
ATOM   1413  CE1 HIS B2055     -22.569  30.891  24.960  1.00  2.00           C
ATOM   1414  NE2 HIS B2055     -21.362  31.384  25.166  1.00  3.10           N
ATOM   1415  H   HIS B2055     -20.241  33.532  21.142  0.00  0.00           H
ATOM   1416  HD1 HIS B2055     -24.025  31.364  23.581  0.00  0.00           H
ATOM   1417  HE2 HIS B2055     -20.608  30.877  25.532  0.00  0.00           H
ATOM   1418  N   ALA B2056     -22.644  34.290  19.170  1.00 10.33           N
ATOM   1419  CA  ALA B2056     -23.442  34.935  18.130  1.00 10.51           C
ATOM   1420  C   ALA B2056     -23.731  33.985  16.974  1.00 14.24           C
ATOM   1421  O   ALA B2056     -24.885  33.829  16.556  1.00 17.21           O
ATOM   1422  CB  ALA B2056     -22.729  36.161  17.619  1.00  9.92           C
ATOM   1423  H   ALA B2056     -21.767  34.651  19.397  0.00  0.00           H
ATOM   1424  N   MET B2057     -22.680  33.340  16.476  1.00 11.79           N
ATOM   1425  CA  MET B2057     -22.810  32.294  15.469  1.00 15.13           C
ATOM   1426  C   MET B2057     -23.842  31.222  15.834  1.00 17.76           C
ATOM   1427  O   MET B2057     -24.808  31.000  15.100  1.00 16.63           O
ATOM   1428  CB  MET B2057     -21.452  31.642  15.231  1.00 17.94           C
ATOM   1429  CG  MET B2057     -20.692  32.266  14.087  1.00 27.92           C
ATOM   1430  SD  MET B2057     -18.979  31.767  14.037  1.00 39.79           S
ATOM   1431  CE  MET B2057     -18.164  33.353  14.482  1.00 41.99           C
ATOM   1432  H   MET B2057     -21.792  33.596  16.814  0.00  0.00           H
ATOM   1433  N   MET B2058     -23.679  30.615  17.005  1.00 20.22           N
ATOM   1434  CA  MET B2058     -24.617  29.603  17.489  1.00 21.71           C
ATOM   1435  C   MET B2058     -26.074  30.032  17.295  1.00 25.10           C
ATOM   1436  O   MET B2058     -26.865  29.330  16.659  1.00 28.18           O
ATOM   1437  CB  MET B2058     -24.359  29.323  18.969  1.00 20.36           C
ATOM   1438  CG  MET B2058     -22.991  28.760  19.256  1.00 15.47           C
```

Fig 4-25

```
ATOM   1439  SD  MET B2058     -22.714  27.281  18.302  1.00 20.16           S
ATOM   1440  CE  MET B2058     -23.353  26.049  19.380  1.00 12.03           C
ATOM   1441  H   MET B2058     -22.898  30.870  17.543  0.00  0.00           H
ATOM   1442  N   GLU B2059     -26.375  31.246  17.742  1.00 25.58           N
ATOM   1443  CA  GLU B2059     -27.725  31.798  17.694  1.00 26.53           C
ATOM   1444  C   GLU B2059     -28.224  32.039  16.261  1.00 24.75           C
ATOM   1445  O   GLU B2059     -29.425  32.148  16.022  1.00 24.66           O
ATOM   1446  CB  GLU B2059     -27.759  33.099  18.504  1.00 26.67           C
ATOM   1447  CG  GLU B2059     -29.007  33.941  18.330  1.00 28.36           C
ATOM   1448  CD  GLU B2059     -28.701  35.344  17.828  1.00 34.40           C
ATOM   1449  OE1 GLU B2059     -27.515  35.648  17.560  1.00 37.80           O
ATOM   1450  OE2 GLU B2059     -29.653  36.146  17.699  1.00 36.02           O
ATOM   1451  H   GLU B2059     -25.654  31.794  18.125  0.00  0.00           H
ATOM   1452  N   ARG B2060     -27.303  32.057  15.307  1.00 23.58           N
ATOM   1453  CA  ARG B2060     -27.660  32.296  13.914  1.00 27.89           C
ATOM   1454  C   ARG B2060     -27.992  31.021  13.117  1.00 26.90           C
ATOM   1455  O   ARG B2060     -28.925  31.013  12.317  1.00 26.30           O
ATOM   1456  CB  ARG B2060     -26.547  33.091  13.224  1.00 31.68           C
ATOM   1457  CG  ARG B2060     -26.338  34.497  13.808  1.00 33.63           C
ATOM   1458  CD  ARG B2060     -27.275  35.527  13.173  1.00 36.15           C
ATOM   1459  NE  ARG B2060     -28.381  35.927  14.046  1.00 35.55           N
ATOM   1460  CZ  ARG B2060     -29.635  35.492  13.924  1.00 37.00           C
ATOM   1461  NH1 ARG B2060     -29.933  34.533  13.057  1.00 33.57           N
ATOM   1462  NH2 ARG B2060     -30.590  35.982  14.704  1.00 38.84           N
ATOM   1463  H   ARG B2060     -26.365  31.985  15.562  0.00  0.00           H
ATOM   1464  HE  ARG B2060     -28.189  36.558  14.770  0.00  0.00           H
ATOM   1465 1HH1 ARG B2060     -29.220  34.125  12.486  0.00  0.00           H
ATOM   1466 2HH1 ARG B2060     -30.874  34.210  12.967  0.00  0.00           H
ATOM   1467 1HH2 ARG B2060     -30.376  36.677  15.389  0.00  0.00           H
ATOM   1468 2HH2 ARG B2060     -31.526  35.646  14.601  0.00  0.00           H
ATOM   1469  N   GLY B2061     -27.246  29.945  13.351  1.00 27.44           N
ATOM   1470  CA  GLY B2061     -27.597  28.662  12.758  1.00 23.84           C
ATOM   1471  C   GLY B2061     -26.442  27.751  12.361  1.00 25.08           C
ATOM   1472  O   GLY B2061     -25.500  28.198  11.690  1.00 29.79           O
ATOM   1473  H   GLY B2061     -26.500  30.030  13.976  0.00  0.00           H
ATOM   1474  N   PRO B2062     -26.516  26.448  12.695  1.00 21.10           N
ATOM   1475  CA  PRO B2062     -25.740  25.433  11.976  1.00 19.45           C
ATOM   1476  C   PRO B2062     -26.051  25.463  10.487  1.00 21.95           C
ATOM   1477  O   PRO B2062     -27.208  25.349  10.085  1.00 26.38           O
ATOM   1478  CB  PRO B2062     -26.204  24.110  12.585  1.00 14.25           C
ATOM   1479  CG  PRO B2062     -27.072  24.467  13.734  1.00 14.98           C
ATOM   1480  CD  PRO B2062     -27.590  25.836  13.489  1.00 18.97           C
ATOM   1481  N   GLN B2063     -25.048  25.729   9.670  1.00 21.33           N
ATOM   1482  CA  GLN B2063     -25.258  25.668   8.224  1.00 22.88           C
ATOM   1483  C   GLN B2063     -24.930  24.278   7.701  1.00 19.53           C
ATOM   1484  O   GLN B2063     -25.781  23.568   7.181  1.00 22.10           O
ATOM   1485  CB  GLN B2063     -24.384  26.700   7.510  1.00 25.75           C
ATOM   1486  CG  GLN B2063     -25.131  27.922   7.002  1.00 30.23           C
ATOM   1487  CD  GLN B2063     -24.186  29.035   6.545  1.00 37.47           C
ATOM   1488  OE1 GLN B2063     -23.139  28.776   5.945  1.00 42.91           O
ATOM   1489  NE2 GLN B2063     -24.556  30.280   6.822  1.00 34.40           N
ATOM   1490  H   GLN B2063     -24.240  26.065  10.056  0.00  0.00           H
ATOM   1491 1HE2 GLN B2063     -23.899  30.917   6.484  0.00  0.00           H
ATOM   1492 2HE2 GLN B2063     -25.396  30.488   7.270  0.00  0.00           H
ATOM   1493  N   THR B2064     -23.685  23.880   7.897  1.00 16.77           N
ATOM   1494  CA  THR B2064     -23.220  22.593   7.423  1.00 17.61           C
ATOM   1495  C   THR B2064     -23.743  21.471   8.322  1.00 17.50           C
ATOM   1496  O   THR B2064     -24.272  21.725   9.402  1.00 19.82           O
ATOM   1497  CB  THR B2064     -21.689  22.551   7.414  1.00 18.02           C
ATOM   1498  OG1 THR B2064     -21.213  22.465   8.763  1.00 16.37           O
```

Fig 4-26

```
ATOM   1499  CG2 THR B2064     -21.128  23.812   6.763  1.00 19.18           C
ATOM   1500  H   THR B2064     -23.114  24.477   8.406  0.00  0.00           H
ATOM   1501  HG1 THR B2064     -21.145  21.529   8.956  0.00  0.00           H
ATOM   1502  N   LEU B2065     -23.481  20.231   7.922  1.00 17.20           N
ATOM   1503  CA  LEU B2065     -23.813  19.063   8.731  1.00 13.79           C
ATOM   1504  C   LEU B2065     -22.940  18.949   9.988  1.00 13.22           C
ATOM   1505  O   LEU B2065     -23.445  18.670  11.070  1.00 12.57           O
ATOM   1506  CB  LEU B2065     -23.667  17.808   7.879  1.00 17.73           C
ATOM   1507  CG  LEU B2065     -24.909  16.954   7.614  1.00 18.83           C
ATOM   1508  CD1 LEU B2065     -26.158  17.819   7.466  1.00 19.10           C
ATOM   1509  CD2 LEU B2065     -24.658  16.129   6.365  1.00 14.71           C
ATOM   1510  H   LEU B2065     -23.146  20.079   7.018  0.00  0.00           H
ATOM   1511  N   LYS B2066     -21.649  19.264   9.848  1.00  9.29           N
ATOM   1512  CA  LYS B2066     -20.707  19.308  10.976  1.00  8.13           C
ATOM   1513  C   LYS B2066     -21.072  20.317  12.070  1.00 11.53           C
ATOM   1514  O   LYS B2066     -20.704  20.148  13.226  1.00 16.33           O
ATOM   1515  CB  LYS B2066     -19.297  19.636  10.475  1.00  2.00           C
ATOM   1516  CG  LYS B2066     -18.442  18.438  10.157  1.00  2.00           C
ATOM   1517  CD  LYS B2066     -17.028  18.870   9.846  1.00  2.00           C
ATOM   1518  CE  LYS B2066     -16.122  17.672   9.553  1.00  9.62           C
ATOM   1519  NZ  LYS B2066     -16.549  16.861   8.378  1.00  5.28           N
ATOM   1520  H   LYS B2066     -21.297  19.271   8.935  0.00  0.00           H
ATOM   1521 1HZ  LYS B2066     -17.527  16.533   8.514  0.00  0.00           H
ATOM   1522 2HZ  LYS B2066     -16.491  17.449   7.520  0.00  0.00           H
ATOM   1523 3HZ  LYS B2066     -15.912  16.043   8.283  0.00  0.00           H
ATOM   1524  N   GLU B2067     -21.548  21.479  11.646  1.00 14.92           N
ATOM   1525  CA  GLU B2067     -21.998  22.508  12.569  1.00 15.78           C
ATOM   1526  C   GLU B2067     -23.336  22.108  13.173  1.00 19.42           C
ATOM   1527  O   GLU B2067     -23.693  22.562  14.260  1.00 22.50           O
ATOM   1528  CB  GLU B2067     -22.143  23.842  11.835  1.00 22.50           C
ATOM   1529  CG  GLU B2067     -20.877  24.292  11.105  1.00 25.09           C
ATOM   1530  CD  GLU B2067     -21.032  25.619  10.365  1.00 25.97           C
ATOM   1531  OE1 GLU B2067     -22.161  26.174  10.309  1.00 16.81           O
ATOM   1532  OE2 GLU B2067     -20.002  26.108   9.844  1.00 26.65           O
ATOM   1533  H   GLU B2067     -21.556  21.672  10.692  0.00  0.00           H
ATOM   1534  N   THR B2068     -24.096  21.300  12.435  1.00 19.36           N
ATOM   1535  CA  THR B2068     -25.345  20.731  12.940  1.00 18.73           C
ATOM   1536  C   THR B2068     -25.120  19.751  14.100  1.00 20.11           C
ATOM   1537  O   THR B2068     -25.625  19.971  15.204  1.00 24.18           O
ATOM   1538  CB  THR B2068     -26.140  20.025  11.809  1.00 14.88           C
ATOM   1539  OG1 THR B2068     -26.656  21.013  10.912  1.00 16.48           O
ATOM   1540  CG2 THR B2068     -27.317  19.239  12.370  1.00 13.69           C
ATOM   1541  H   THR B2068     -23.847  21.150  11.501  0.00  0.00           H
ATOM   1542  HG1 THR B2068     -25.961  21.423  10.376  0.00  0.00           H
ATOM   1543  N   SER B2069     -24.303  18.724  13.879  1.00 15.42           N
ATOM   1544  CA  SER B2069     -24.066  17.701  14.898  1.00 11.92           C
ATOM   1545  C   SER B2069     -23.404  18.243  16.180  1.00 14.81           C
ATOM   1546  O   SER B2069     -23.865  17.962  17.295  1.00 17.69           O
ATOM   1547  CB  SER B2069     -23.234  16.555  14.315  1.00  3.97           C
ATOM   1548  OG  SER B2069     -21.951  16.993  13.917  1.00  2.00           O
ATOM   1549  H   SER B2069     -23.872  18.626  13.000  0.00  0.00           H
ATOM   1550  HG  SER B2069     -21.427  16.200  13.756  0.00  0.00           H
ATOM   1551  N   PHE B2070     -22.371  19.070  16.018  1.00 12.68           N
ATOM   1552  CA  PHE B2070     -21.786  19.831  17.132  1.00  6.20           C
ATOM   1553  C   PHE B2070     -22.856  20.601  17.888  1.00  2.60           C
ATOM   1554  O   PHE B2070     -22.752  20.790  19.082  1.00  7.27           O
ATOM   1555  CB  PHE B2070     -20.732  20.811  16.607  1.00  5.44           C
ATOM   1556  CG  PHE B2070     -20.154  21.726  17.656  1.00  2.00           C
ATOM   1557  CD1 PHE B2070     -20.857  22.848  18.092  1.00  2.00           C
ATOM   1558  CD2 PHE B2070     -18.861  21.521  18.130  1.00  2.00           C
```

Fig 4-27

```
ATOM   1559  CE1  PHE B2070    -20.283  23.748  18.980  1.00   2.00      C
ATOM   1560  CE2  PHE B2070    -18.272  22.419  19.016  1.00   2.00      C
ATOM   1561  CZ   PHE B2070    -18.985  23.534  19.441  1.00   2.00      C
ATOM   1562  H    PHE B2070    -21.960  19.083  15.126  0.00   0.00      H
ATOM   1563  N    ASN B2071    -23.836  21.135  17.182  1.00   2.01      N
ATOM   1564  CA   ASN B2071    -24.876  21.880  17.851  1.00   2.00      C
ATOM   1565  C    ASN B2071    -25.784  20.959  18.646  1.00   4.16      C
ATOM   1566  O    ASN B2071    -26.258  21.328  19.711  1.00  10.87      O
ATOM   1567  CB   ASN B2071    -25.689  22.675  16.841  1.00   7.02      C
ATOM   1568  CG   ASN B2071    -26.604  23.677  17.501  1.00   8.30      C
ATOM   1569  OD1  ASN B2071    -27.805  23.463  17.602  1.00  11.66      O
ATOM   1570  ND2  ASN B2071    -26.035  24.766  17.987  1.00  12.66      N
ATOM   1571  H    ASN B2071    -23.831  21.076  16.202  0.00   0.00      H
ATOM   1572  1HD2 ASN B2071    -26.665  25.370  18.419  0.00   0.00      H
ATOM   1573  2HD2 ASN B2071    -25.081  24.904  17.878  0.00   0.00      H
ATOM   1574  N    GLN B2072    -25.998  19.747  18.143  1.00   8.02      N
ATOM   1575  CA   GLN B2072    -26.801  18.741  18.845  1.00   8.00      C
ATOM   1576  C    GLN B2072    -26.101  18.262  20.103  1.00  12.51      C
ATOM   1577  O    GLN B2072    -26.693  18.224  21.178  1.00  19.60      O
ATOM   1578  CB   GLN B2072    -27.061  17.554  17.934  1.00   2.00      C
ATOM   1579  CG   GLN B2072    -28.010  17.884  16.798  1.00   6.79      C
ATOM   1580  CD   GLN B2072    -27.941  16.881  15.665  1.00   8.96      C
ATOM   1581  OE1  GLN B2072    -27.006  16.088  15.570  1.00   4.92      O
ATOM   1582  NE2  GLN B2072    -28.940  16.908  14.798  1.00   6.99      N
ATOM   1583  H    GLN B2072    -25.642  19.564  17.247  0.00   0.00      H
ATOM   1584  1HE2 GLN B2072    -28.875  16.258  14.072  0.00   0.00      H
ATOM   1585  2HE2 GLN B2072    -29.659  17.557  14.919  0.00   0.00      H
ATOM   1586  N    ALA B2073    -24.795  18.054  19.978  1.00  14.16      N
ATOM   1587  CA   ALA B2073    -23.940  17.625  21.077  1.00  14.24      C
ATOM   1588  C    ALA B2073    -23.756  18.666  22.196  1.00  15.13      C
ATOM   1589  O    ALA B2073    -24.013  18.383  23.369  1.00  18.26      O
ATOM   1590  CB   ALA B2073    -22.583  17.223  20.518  1.00  15.34      C
ATOM   1591  H    ALA B2073    -24.426  18.142  19.081  0.00   0.00      H
ATOM   1592  N    TYR B2074    -23.228  19.834  21.832  1.00  12.69      N
ATOM   1593  CA   TYR B2074    -22.791  20.842  22.796  1.00   8.11      C
ATOM   1594  C    TYR B2074    -23.618  22.128  22.804  1.00   8.66      C
ATOM   1595  O    TYR B2074    -23.291  23.074  23.509  1.00   9.77      O
ATOM   1596  CB   TYR B2074    -21.330  21.206  22.547  1.00   3.13      C
ATOM   1597  CG   TYR B2074    -20.444  20.034  22.216  1.00   8.31      C
ATOM   1598  CD1  TYR B2074    -20.045  19.124  23.197  1.00  11.16      C
ATOM   1599  CD2  TYR B2074    -19.990  19.839  20.918  1.00  10.92      C
ATOM   1600  CE1  TYR B2074    -19.205  18.050  22.882  1.00  12.75      C
ATOM   1601  CE2  TYR B2074    -19.160  18.772  20.591  1.00  12.41      C
ATOM   1602  CZ   TYR B2074    -18.771  17.886  21.569  1.00  12.54      C
ATOM   1603  OH   TYR B2074    -17.960  16.836  21.215  1.00  21.64      O
ATOM   1604  H    TYR B2074    -23.091  19.988  20.874  0.00   0.00      H
ATOM   1605  HH   TYR B2074    -17.868  16.773  20.266  0.00   0.00      H
ATOM   1606  N    GLY B2075    -24.714  22.153  22.063  1.00  10.37      N
ATOM   1607  CA   GLY B2075    -25.478  23.380  21.946  1.00  12.34      C
ATOM   1608  C    GLY B2075    -26.130  23.796  23.246  1.00  17.07      C
ATOM   1609  O    GLY B2075    -26.010  24.946  23.660  1.00  24.52      O
ATOM   1610  H    GLY B2075    -24.997  21.355  21.565  0.00   0.00      H
ATOM   1611  N    ARG B2076    -26.770  22.843  23.921  1.00  19.49      N
ATOM   1612  CA   ARG B2076    -27.476  23.089  25.187  1.00  16.21      C
ATOM   1613  C    ARG B2076    -26.574  23.640  26.305  1.00  11.79      C
ATOM   1614  O    ARG B2076    -26.861  24.680  26.885  1.00  11.52      O
ATOM   1615  CB   ARG B2076    -28.162  21.794  25.651  1.00  17.61      C
ATOM   1616  CG   ARG B2076    -28.703  21.826  27.072  1.00  25.98      C
ATOM   1617  CD   ARG B2076    -29.913  20.929  27.228  1.00  33.40      C
ATOM   1618  NE   ARG B2076    -31.135  21.578  26.754  1.00  44.19      N
```

Fig 4-28

```
ATOM   1619  CZ   ARG B2076     -32.351  21.341  27.241  1.00 50.69      C
ATOM   1620  NH1  ARG B2076     -32.532  20.415  28.180  1.00 51.70      N
ATOM   1621  NH2  ARG B2076     -33.396  22.014  26.769  1.00 53.46      N
ATOM   1622  H    ARG B2076     -26.782  21.950  23.516  0.00  0.00      H
ATOM   1623  HE   ARG B2076     -31.060  22.233  26.029  0.00  0.00      H
ATOM   1624  1HH1 ARG B2076     -31.750  19.895  28.525  0.00  0.00      H
ATOM   1625  2HH1 ARG B2076     -33.446  20.249  28.551  0.00  0.00      H
ATOM   1626  1HH2 ARG B2076     -33.274  22.698  26.051  0.00  0.00      H
ATOM   1627  2HH2 ARG B2076     -34.308  21.839  27.144  0.00  0.00      H
ATOM   1628  N    ASP B2077     -25.490  22.936  26.604  1.00  8.15      N
ATOM   1629  CA   ASP B2077     -24.526  23.394  27.594  1.00  6.48      C
ATOM   1630  C    ASP B2077     -24.035  24.809  27.331  1.00  8.55      C
ATOM   1631  O    ASP B2077     -24.126  25.669  28.201  1.00 13.05      O
ATOM   1632  CB   ASP B2077     -23.332  22.448  27.637  1.00  5.61      C
ATOM   1633  CG   ASP B2077     -23.615  21.196  28.425  1.00 10.00      C
ATOM   1634  OD1  ASP B2077     -24.726  21.096  28.999  1.00  9.97      O
ATOM   1635  OD2  ASP B2077     -22.724  20.317  28.479  1.00 12.06      O
ATOM   1636  H    ASP B2077     -25.346  22.086  26.144  0.00  0.00      H
ATOM   1637  N    LEU B2078     -23.544  25.058  26.123  1.00  6.49      N
ATOM   1638  CA   LEU B2078     -23.064  26.386  25.752  1.00  4.74      C
ATOM   1639  C    LEU B2078     -24.146  27.466  25.862  1.00  4.72      C
ATOM   1640  O    LEU B2078     -23.847  28.626  26.118  1.00  2.64      O
ATOM   1641  CB   LEU B2078     -22.495  26.364  24.333  1.00  3.18      C
ATOM   1642  CG   LEU B2078     -21.161  25.653  24.084  1.00  2.91      C
ATOM   1643  CD1  LEU B2078     -20.928  25.574  22.593  1.00  2.37      C
ATOM   1644  CD2  LEU B2078     -20.010  26.387  24.764  1.00  2.00      C
ATOM   1645  H    LEU B2078     -23.477  24.330  25.469  0.00  0.00      H
ATOM   1646  N    MET B2079     -25.401  27.091  25.651  1.00  7.76      N
ATOM   1647  CA   MET B2079     -26.507  28.022  25.850  1.00 14.65      C
ATOM   1648  C    MET B2079     -26.686  28.344  27.330  1.00 17.59      C
ATOM   1649  O    MET B2079     -26.714  29.505  27.716  1.00 21.68      O
ATOM   1650  CB   MET B2079     -27.803  27.434  25.295  1.00 18.67      C
ATOM   1651  CG   MET B2079     -28.999  28.367  25.363  1.00 25.96      C
ATOM   1652  SD   MET B2079     -29.718  28.677  23.724  1.00 40.57      S
ATOM   1653  CE   MET B2079     -30.358  27.004  23.294  1.00 36.64      C
ATOM   1654  H    MET B2079     -25.579  26.181  25.326  0.00  0.00      H
ATOM   1655  N    GLU B2080     -26.769  27.308  28.158  1.00 18.54      N
ATOM   1656  CA   GLU B2080     -26.928  27.477  29.599  1.00 18.17      C
ATOM   1657  C    GLU B2080     -25.773  28.284  30.191  1.00 16.44      C
ATOM   1658  O    GLU B2080     -25.995  29.230  30.940  1.00 17.68      O
ATOM   1659  CB   GLU B2080     -27.006  26.111  30.286  1.00 24.46      C
ATOM   1660  CG   GLU B2080     -27.581  26.144  31.708  1.00 33.04      C
ATOM   1661  CD   GLU B2080     -27.199  24.914  32.530  1.00 37.28      C
ATOM   1662  OE1  GLU B2080     -27.253  23.783  31.991  1.00 40.40      O
ATOM   1663  OE2  GLU B2080     -26.827  25.080  33.714  1.00 39.48      O
ATOM   1664  H    GLU B2080     -26.733  26.408  27.770  0.00  0.00      H
ATOM   1665  N    ALA B2081     -24.555  27.981  29.756  1.00 15.30      N
ATOM   1666  CA   ALA B2081     -23.375  28.743  30.149  1.00 12.75      C
ATOM   1667  C    ALA B2081     -23.591  30.233  29.912  1.00 14.17      C
ATOM   1668  O    ALA B2081     -23.284  31.057  30.767  1.00 17.02      O
ATOM   1669  CB   ALA B2081     -22.163  28.263  29.373  1.00  8.47      C
ATOM   1670  H    ALA B2081     -24.449  27.180  29.211  0.00  0.00      H
ATOM   1671  N    GLN B2082     -24.253  30.560  28.809  1.00 16.91      N
ATOM   1672  CA   GLN B2082     -24.557  31.948  28.477  1.00 18.00      C
ATOM   1673  C    GLN B2082     -25.558  32.584  29.439  1.00 17.54      C
ATOM   1674  O    GLN B2082     -25.442  33.759  29.768  1.00 19.50      O
ATOM   1675  CB   GLN B2082     -25.085  32.032  27.048  1.00 22.74      C
ATOM   1676  CG   GLN B2082     -25.879  33.280  26.739  1.00 26.79      C
ATOM   1677  CD   GLN B2082     -26.176  33.408  25.268  1.00 31.68      C
ATOM   1678  OE1  GLN B2082     -25.360  33.930  24.509  1.00 29.64      O
```

Fig 4-29

```
ATOM   1679  NE2 GLN B2082     -27.299  32.846  24.838  1.00 31.52           N
ATOM   1680  H   GLN B2082     -24.566  29.833  28.233  0.00  0.00           H
ATOM   1681 1HE2 GLN B2082     -27.467  32.967  23.886  0.00  0.00           H
ATOM   1682 2HE2 GLN B2082     -27.890  32.386  25.460  0.00  0.00           H
ATOM   1683  N   GLU B2083     -26.551  31.819  29.875  1.00 18.34           N
ATOM   1684  CA  GLU B2083     -27.523  32.342  30.826  1.00 19.36           C
ATOM   1685  C   GLU B2083     -26.863  32.651  32.166  1.00 13.37           C
ATOM   1686  O   GLU B2083     -27.102  33.701  32.747  1.00 17.15           O
ATOM   1687  CB  GLU B2083     -28.680  31.362  31.021  1.00 26.08           C
ATOM   1688  CG  GLU B2083     -29.802  31.897  31.915  1.00 40.13           C
ATOM   1689  CD  GLU B2083     -30.388  33.226  31.428  1.00 46.90           C
ATOM   1690  OE1 GLU B2083     -30.878  33.280  30.279  1.00 52.86           O
ATOM   1691  OE2 GLU B2083     -30.392  34.207  32.209  1.00 48.07           O
ATOM   1692  H   GLU B2083     -26.603  30.892  29.552  0.00  0.00           H
ATOM   1693  N   TRP B2084     -25.915  31.817  32.563  1.00  6.62           N
ATOM   1694  CA  TRP B2084     -25.139  32.069  33.761  1.00  3.33           C
ATOM   1695  C   TRP B2084     -24.348  33.355  33.677  1.00  4.82           C
ATOM   1696  O   TRP B2084     -24.240  34.076  34.665  1.00 10.80           O
ATOM   1697  CB  TRP B2084     -24.190  30.914  34.037  1.00  5.07           C
ATOM   1698  CG  TRP B2084     -24.879  29.734  34.575  1.00  6.00           C
ATOM   1699  CD1 TRP B2084     -25.110  28.564  33.924  1.00 10.88           C
ATOM   1700  CD2 TRP B2084     -25.606  29.664  35.801  1.00 10.76           C
ATOM   1701  NE1 TRP B2084     -25.972  27.781  34.646  1.00 17.13           N
ATOM   1702  CE2 TRP B2084     -26.292  28.433  35.807  1.00 14.65           C
ATOM   1703  CE3 TRP B2084     -25.765  30.533  36.887  1.00  9.81           C
ATOM   1704  CZ2 TRP B2084     -27.129  28.050  36.853  1.00 14.61           C
ATOM   1705  CZ3 TRP B2084     -26.597  30.156  37.923  1.00 11.54           C
ATOM   1706  CH2 TRP B2084     -27.272  28.924  37.899  1.00 16.36           C
ATOM   1707  H   TRP B2084     -25.769  30.992  32.047  0.00  0.00           H
ATOM   1708  HE1 TRP B2084     -26.397  26.972  34.309  0.00  0.00           H
ATOM   1709  N   CYS B2085     -23.760  33.625  32.514  1.00  7.15           N
ATOM   1710  CA  CYS B2085     -23.062  34.894  32.274  1.00  7.94           C
ATOM   1711  C   CYS B2085     -24.030  36.070  32.284  1.00 11.28           C
ATOM   1712  O   CYS B2085     -23.718  37.138  32.813  1.00 13.68           O
ATOM   1713  CB  CYS B2085     -22.329  34.868  30.935  1.00  2.21           C
ATOM   1714  SG  CYS B2085     -20.748  34.024  30.993  1.00 14.42           S
ATOM   1715  H   CYS B2085     -23.725  32.895  31.856  0.00  0.00           H
ATOM   1716  N   ARG B2086     -25.214  35.864  31.718  1.00 10.58           N
ATOM   1717  CA  ARG B2086     -26.250  36.878  31.749  1.00 11.82           C
ATOM   1718  C   ARG B2086     -26.618  37.180  33.193  1.00 11.93           C
ATOM   1719  O   ARG B2086     -26.536  38.325  33.629  1.00 14.05           O
ATOM   1720  CB  ARG B2086     -27.476  36.405  30.970  1.00 16.71           C
ATOM   1721  CG  ARG B2086     -27.279  36.429  29.458  1.00 22.27           C
ATOM   1722  CD  ARG B2086     -28.160  35.398  28.768  1.00 36.61           C
ATOM   1723  NE  ARG B2086     -29.300  35.986  28.060  1.00 45.02           N
ATOM   1724  CZ  ARG B2086     -30.003  35.357  27.118  1.00 49.39           C
ATOM   1725  NH1 ARG B2086     -29.673  34.120  26.747  1.00 49.75           N
ATOM   1726  NH2 ARG B2086     -31.021  35.971  26.523  1.00 48.26           N
ATOM   1727  H   ARG B2086     -25.382  35.014  31.259  0.00  0.00           H
ATOM   1728  HE  ARG B2086     -29.553  36.906  28.280  0.00  0.00           H
ATOM   1729 1HH1 ARG B2086     -28.913  33.645  27.190  0.00  0.00           H
ATOM   1730 2HH1 ARG B2086     -30.218  33.649  26.053  0.00  0.00           H
ATOM   1731 1HH2 ARG B2086     -31.246  36.916  26.762  0.00  0.00           H
ATOM   1732 2HH2 ARG B2086     -31.538  35.499  25.809  0.00  0.00           H
ATOM   1733  N   LYS B2087     -26.792  36.120  33.976  1.00 14.39           N
ATOM   1734  CA  LYS B2087     -27.104  36.240  35.401  1.00 11.99           C
ATOM   1735  C   LYS B2087     -26.038  37.041  36.144  1.00  9.73           C
ATOM   1736  O   LYS B2087     -26.356  37.859  37.000  1.00 12.76           O
ATOM   1737  CB  LYS B2087     -27.217  34.858  36.040  1.00 12.74           C
ATOM   1738  CG  LYS B2087     -28.510  34.139  35.778  1.00 13.98           C
```

Fig 4-30

```
ATOM   1739  CD   LYS B2087    -28.412  32.700  36.270  1.00 17.19      C
ATOM   1740  CE   LYS B2087    -29.760  31.998  36.220  1.00 26.67      C
ATOM   1741  NZ   LYS B2087    -29.640  30.517  36.341  1.00 33.46      N
ATOM   1742  H    LYS B2087    -26.697  35.240  33.583  0.00  0.00      H
ATOM   1743 1HZ   LYS B2087    -29.051  30.158  35.561  0.00  0.00      H
ATOM   1744 2HZ   LYS B2087    -29.184  30.284  37.245  0.00  0.00      H
ATOM   1745 3HZ   LYS B2087    -30.581  30.076  36.301  0.00  0.00      H
ATOM   1746  N    TYR B2088    -24.771  36.803  35.821  1.00  7.02      N
ATOM   1747  CA   TYR B2088    -23.693  37.592  36.407  1.00 12.48      C
ATOM   1748  C    TYR B2088    -23.872  39.079  36.109  1.00 15.40      C
ATOM   1749  O    TYR B2088    -23.750  39.921  37.000  1.00 21.76      O
ATOM   1750  CB   TYR B2088    -22.327  37.135  35.892  1.00  9.00      C
ATOM   1751  CG   TYR B2088    -21.194  38.013  36.386  1.00 11.53      C
ATOM   1752  CD1  TYR B2088    -20.780  37.953  37.712  1.00 13.53      C
ATOM   1753  CD2  TYR B2088    -20.603  38.967  35.553  1.00  9.73      C
ATOM   1754  CE1  TYR B2088    -19.817  38.822  38.205  1.00 13.24      C
ATOM   1755  CE2  TYR B2088    -19.631  39.835  36.032  1.00  8.20      C
ATOM   1756  CZ   TYR B2088    -19.248  39.758  37.364  1.00 14.19      C
ATOM   1757  OH   TYR B2088    -18.308  40.621  37.881  1.00 21.06      O
ATOM   1758  H    TYR B2088    -24.578  36.057  35.209  0.00  0.00      H
ATOM   1759  HH   TYR B2088    -17.982  41.148  37.148  0.00  0.00      H
ATOM   1760  N    MET B2089    -24.238  39.383  34.870  1.00 14.77      N
ATOM   1761  CA   MET B2089    -24.442  40.757  34.446  1.00 13.39      C
ATOM   1762  C    MET B2089    -25.500  41.475  35.272  1.00 11.34      C
ATOM   1763  O    MET B2089    -25.392  42.669  35.511  1.00 16.85      O
ATOM   1764  CB   MET B2089    -24.813  40.789  32.962  1.00 11.91      C
ATOM   1765  CG   MET B2089    -23.637  40.488  32.049  1.00 11.63      C
ATOM   1766  SD   MET B2089    -24.124  40.080  30.365  1.00 13.84      S
ATOM   1767  CE   MET B2089    -22.620  39.331  29.759  1.00  2.00      C
ATOM   1768  H    MET B2089    -24.371  38.652  34.223  0.00  0.00      H
ATOM   1769  N    LYS B2090    -26.475  40.728  35.775  1.00 13.58      N
ATOM   1770  CA   LYS B2090    -27.591  41.322  36.506  1.00 17.01      C
ATOM   1771  C    LYS B2090    -27.371  41.420  38.023  1.00 18.18      C
ATOM   1772  O    LYS B2090    -28.022  42.230  38.695  1.00 16.27      O
ATOM   1773  CB   LYS B2090    -28.886  40.552  36.209  1.00 17.48      C
ATOM   1774  CG   LYS B2090    -29.218  39.436  37.207  1.00 30.54      C
ATOM   1775  CD   LYS B2090    -30.240  39.892  38.254  1.00 39.03      C
ATOM   1776  CE   LYS B2090    -30.140  39.078  39.545  1.00 40.52      C
ATOM   1777  NZ   LYS B2090    -30.477  39.893  40.756  1.00 38.43      N
ATOM   1778  H    LYS B2090    -26.475  39.771  35.559  0.00  0.00      H
ATOM   1779 1HZ   LYS B2090    -29.826  40.700  40.829  0.00  0.00      H
ATOM   1780 2HZ   LYS B2090    -31.451  40.248  40.672  0.00  0.00      H
ATOM   1781 3HZ   LYS B2090    -30.396  39.308  41.612  0.00  0.00      H
ATOM   1782  N    SER B2091    -26.466  40.597  38.554  1.00 18.19      N
ATOM   1783  CA   SER B2091    -26.302  40.464  40.008  1.00 16.08      C
ATOM   1784  C    SER B2091    -24.917  40.794  40.537  1.00 14.61      C
ATOM   1785  O    SER B2091    -24.761  41.071  41.724  1.00 16.95      O
ATOM   1786  CB   SER B2091    -26.662  39.051  40.465  1.00 15.61      C
ATOM   1787  OG   SER B2091    -25.722  38.108  39.982  1.00 18.00      O
ATOM   1788  H    SER B2091    -25.955  40.047  37.923  0.00  0.00      H
ATOM   1789  HG   SER B2091    -26.010  37.832  39.096  0.00  0.00      H
ATOM   1790  N    GLY B2092    -23.903  40.637  39.691  1.00 10.93      N
ATOM   1791  CA   GLY B2092    -22.536  40.883  40.117  1.00 12.47      C
ATOM   1792  C    GLY B2092    -22.009  39.837  41.083  1.00 13.42      C
ATOM   1793  O    GLY B2092    -20.913  39.974  41.622  1.00 11.96      O
ATOM   1794  H    GLY B2092    -24.107  40.356  38.784  0.00  0.00      H
ATOM   1795  N    ASN B2093    -22.701  38.704  41.127  1.00 14.42      N
ATOM   1796  CA   ASN B2093    -22.465  37.664  42.114  1.00 15.72      C
ATOM   1797  C    ASN B2093    -21.112  36.959  42.015  1.00 20.92      C
ATOM   1798  O    ASN B2093    -20.599  36.466  43.015  1.00 28.74      O
```

Fig 4-31

| | | | | | | | | | |
|---|---|---|---|---|---|---|---|---|---|
| ATOM | 1799 | CB | ASN | B2093 | -23.572 | 36.626 | 42.021 | 1.00 15.84 | C |
| ATOM | 1800 | CG | ASN | B2093 | -23.884 | 35.977 | 43.353 | 1.00 16.87 | C |
| ATOM | 1801 | OD1 | ASN | B2093 | -25.031 | 35.976 | 43.798 | 1.00 23.23 | O |
| ATOM | 1802 | ND2 | ASN | B2093 | -22.879 | 35.381 | 43.975 | 1.00  9.23 | N |
| ATOM | 1803 | H | ASN | B2093 | -23.481 | 38.626 | 40.514 | 0.00  0.00 | H |
| ATOM | 1804 | 1HD2 | ASN | B2093 | -23.187 | 35.027 | 44.822 | 0.00  0.00 | H |
| ATOM | 1805 | 2HD2 | ASN | B2093 | -21.955 | 35.362 | 43.700 | 0.00  0.00 | H |
| ATOM | 1806 | N | VAL | B2094 | -20.653 | 36.711 | 40.797 | 1.00 18.46 | N |
| ATOM | 1807 | CA | VAL | B2094 | -19.386 | 36.003 | 40.528 | 1.00 19.15 | C |
| ATOM | 1808 | C | VAL | B2094 | -19.390 | 34.508 | 40.807 | 1.00 17.55 | C |
| ATOM | 1809 | O | VAL | B2094 | -18.534 | 33.779 | 40.311 | 1.00 20.43 | O |
| ATOM | 1810 | CB | VAL | B2094 | -18.134 | 36.636 | 41.223 | 1.00 17.65 | C |
| ATOM | 1811 | CG1 | VAL | B2094 | -17.885 | 36.035 | 42.612 | 1.00 19.24 | C |
| ATOM | 1812 | CG2 | VAL | B2094 | -16.911 | 36.422 | 40.333 | 1.00 22.37 | C |
| ATOM | 1813 | H | VAL | B2094 | -21.105 | 37.113 | 40.045 | 0.00  0.00 | H |
| ATOM | 1814 | N | LYS | B2095 | -20.415 | 34.016 | 41.485 | 1.00 16.99 | N |
| ATOM | 1815 | CA | LYS | B2095 | -20.615 | 32.570 | 41.511 | 1.00 19.09 | C |
| ATOM | 1816 | C | LYS | B2095 | -21.515 | 32.087 | 40.378 | 1.00 16.91 | C |
| ATOM | 1817 | O | LYS | B2095 | -21.621 | 30.893 | 40.110 | 1.00 15.63 | O |
| ATOM | 1818 | CB | LYS | B2095 | -21.166 | 32.125 | 42.869 | 1.00 24.46 | C |
| ATOM | 1819 | CG | LYS | B2095 | -20.193 | 31.221 | 43.633 | 1.00 33.72 | C |
| ATOM | 1820 | CD | LYS | B2095 | -18.736 | 31.682 | 43.507 | 1.00 32.25 | C |
| ATOM | 1821 | CE | LYS | B2095 | -17.771 | 30.625 | 44.033 | 1.00 37.61 | C |
| ATOM | 1822 | NZ | LYS | B2095 | -17.512 | 29.527 | 43.054 | 1.00 34.92 | N |
| ATOM | 1823 | H | LYS | B2095 | -20.859 | 34.593 | 42.164 | 0.00  0.00 | H |
| ATOM | 1824 | 1HZ | LYS | B2095 | -17.131 | 29.930 | 42.177 | 0.00  0.00 | H |
| ATOM | 1825 | 2HZ | LYS | B2095 | -16.816 | 28.873 | 43.458 | 0.00  0.00 | H |
| ATOM | 1826 | 3HZ | LYS | B2095 | -18.395 | 29.025 | 42.842 | 0.00  0.00 | H |
| ATOM | 1827 | N | ASP | B2096 | -22.168 | 33.029 | 39.710 | 1.00 14.55 | N |
| ATOM | 1828 | CA | ASP | B2096 | -22.850 | 32.737 | 38.459 | 1.00 11.12 | C |
| ATOM | 1829 | C | ASP | B2096 | -21.837 | 32.538 | 37.339 | 1.00 10.59 | C |
| ATOM | 1830 | O | ASP | B2096 | -21.903 | 31.563 | 36.590 | 1.00 13.81 | O |
| ATOM | 1831 | CB | ASP | B2096 | -23.799 | 33.868 | 38.099 | 1.00 12.16 | C |
| ATOM | 1832 | CG | ASP | B2096 | -24.973 | 33.956 | 39.042 | 1.00 14.76 | C |
| ATOM | 1833 | OD1 | ASP | B2096 | -25.630 | 32.925 | 39.259 | 1.00 18.49 | O |
| ATOM | 1834 | OD2 | ASP | B2096 | -25.238 | 35.055 | 39.567 | 1.00 24.14 | O |
| ATOM | 1835 | H | ASP | B2096 | -22.269 | 33.893 | 40.141 | 0.00  0.00 | H |
| ATOM | 1836 | N | LEU | B2097 | -20.816 | 33.386 | 37.326 | 1.00  7.24 | N |
| ATOM | 1837 | CA | LEU | B2097 | -19.723 | 33.244 | 36.383 | 1.00  7.03 | C |
| ATOM | 1838 | C | LEU | B2097 | -19.056 | 31.873 | 36.504 | 1.00 12.75 | C |
| ATOM | 1839 | O | LEU | B2097 | -18.854 | 31.190 | 35.499 | 1.00 17.71 | O |
| ATOM | 1840 | CB | LEU | B2097 | -18.701 | 34.357 | 36.591 | 1.00  2.85 | C |
| ATOM | 1841 | CG | LEU | B2097 | -18.252 | 35.073 | 35.317 | 1.00  7.43 | C |
| ATOM | 1842 | CD1 | LEU | B2097 | -19.451 | 35.345 | 34.428 | 1.00  2.68 | C |
| ATOM | 1843 | CD2 | LEU | B2097 | -17.543 | 36.371 | 35.661 | 1.00  6.68 | C |
| ATOM | 1844 | H | LEU | B2097 | -20.814 | 34.129 | 37.956 | 0.00  0.00 | H |
| ATOM | 1845 | N | THR | B2098 | -18.847 | 31.410 | 37.735 | 1.00 13.89 | N |
| ATOM | 1846 | CA | THR | B2098 | -18.266 | 30.082 | 37.954 | 1.00 14.50 | C |
| ATOM | 1847 | C | THR | B2098 | -19.187 | 28.940 | 37.521 | 1.00 14.65 | C |
| ATOM | 1848 | O | THR | B2098 | -18.733 | 27.967 | 36.924 | 1.00 20.42 | O |
| ATOM | 1849 | CB | THR | B2098 | -17.866 | 29.853 | 39.429 | 1.00 18.86 | C |
| ATOM | 1850 | OG1 | THR | B2098 | -18.952 | 30.231 | 40.288 | 1.00 27.76 | O |
| ATOM | 1851 | CG2 | THR | B2098 | -16.624 | 30.666 | 39.781 | 1.00 14.88 | C |
| ATOM | 1852 | H | THR | B2098 | -19.017 | 31.985 | 38.512 | 0.00  0.00 | H |
| ATOM | 1853 | HG1 | THR | B2098 | -19.663 | 29.576 | 40.325 | 0.00  0.00 | H |
| ATOM | 1854 | N | GLN | B2099 | -20.486 | 29.070 | 37.772 | 1.00 13.41 | N |
| ATOM | 1855 | CA | GLN | B2099 | -21.443 | 28.076 | 37.293 | 1.00 10.97 | C |
| ATOM | 1856 | C | GLN | B2099 | -21.478 | 28.072 | 35.768 | 1.00  9.33 | C |
| ATOM | 1857 | O | GLN | B2099 | -21.842 | 27.085 | 35.147 | 1.00 13.05 | O |
| ATOM | 1858 | CB | GLN | B2099 | -22.843 | 28.371 | 37.838 | 1.00 19.13 | C |

Fig 4-32

```
ATOM   1859  CG   GLN B2099     -23.423  27.264  38.720  1.00 26.63           C
ATOM   1860  CD   GLN B2099     -23.315  25.887  38.084  1.00 33.37           C
ATOM   1861  OE1  GLN B2099     -22.604  25.017  38.580  1.00 35.83           O
ATOM   1862  NE2  GLN B2099     -23.989  25.697  36.959  1.00 38.47           N
ATOM   1863  H    GLN B2099     -20.807  29.834  38.297  0.00  0.00           H
ATOM   1864 1HE2  GLN B2099     -23.848  24.808  36.587  0.00  0.00           H
ATOM   1865 2HE2  GLN B2099     -24.521  26.407  36.558  0.00  0.00           H
ATOM   1866  N    ALA B2100     -21.146  29.211  35.178  1.00  9.52           N
ATOM   1867  CA   ALA B2100     -21.016  29.323  33.738  1.00  3.77           C
ATOM   1868  C    ALA B2100     -19.760  28.586  33.277  1.00  2.86           C
ATOM   1869  O    ALA B2100     -19.823  27.736  32.394  1.00  2.63           O
ATOM   1870  CB   ALA B2100     -20.953  30.796  33.348  1.00  2.00           C
ATOM   1871  H    ALA B2100     -21.074  30.018  35.723  0.00  0.00           H
ATOM   1872  N    TRP B2101     -18.659  28.801  33.988  1.00  2.00           N
ATOM   1873  CA   TRP B2101     -17.367  28.222  33.627  1.00  3.21           C
ATOM   1874  C    TRP B2101     -17.206  26.736  33.960  1.00  8.69           C
ATOM   1875  O    TRP B2101     -16.274  26.065  33.501  1.00 10.67           O
ATOM   1876  CB   TRP B2101     -16.263  29.010  34.300  1.00  3.18           C
ATOM   1877  CG   TRP B2101     -15.704  30.029  33.420  1.00  4.37           C
ATOM   1878  CD1  TRP B2101     -15.775  31.378  33.581  1.00  5.99           C
ATOM   1879  CD2  TRP B2101     -15.003  29.798  32.198  1.00  5.80           C
ATOM   1880  NE1  TRP B2101     -15.158  32.008  32.525  1.00 13.05           N
ATOM   1881  CE2  TRP B2101     -14.676  31.057  31.662  1.00  7.80           C
ATOM   1882  CE3  TRP B2101     -14.625  28.646  31.500  1.00  5.41           C
ATOM   1883  CZ2  TRP B2101     -13.993  31.197  30.456  1.00  6.76           C
ATOM   1884  CZ3  TRP B2101     -13.951  28.786  30.301  1.00  3.13           C
ATOM   1885  CH2  TRP B2101     -13.644  30.052  29.791  1.00  6.31           C
ATOM   1886  H    TRP B2101     -18.717  29.421  34.743  0.00  0.00           H
ATOM   1887  HE1  TRP B2101     -15.113  32.979  32.395  0.00  0.00           H
ATOM   1888  N    ASP B2102     -18.091  26.240  34.807  1.00  8.35           N
ATOM   1889  CA   ASP B2102     -18.235  24.815  35.005  1.00  9.05           C
ATOM   1890  C    ASP B2102     -18.688  24.180  33.686  1.00 10.27           C
ATOM   1891  O    ASP B2102     -18.144  23.158  33.248  1.00 11.33           O
ATOM   1892  CB   ASP B2102     -19.277  24.564  36.099  1.00 13.12           C
ATOM   1893  CG   ASP B2102     -19.127  23.207  36.759  1.00 16.43           C
ATOM   1894  OD1  ASP B2102     -18.048  22.585  36.637  1.00 18.55           O
ATOM   1895  OD2  ASP B2102     -20.084  22.779  37.436  1.00 23.14           O
ATOM   1896  H    ASP B2102     -18.571  26.864  35.388  0.00  0.00           H
ATOM   1897  N    LEU B2103     -19.646  24.828  33.029  1.00  8.01           N
ATOM   1898  CA   LEU B2103     -20.230  24.302  31.794  1.00  7.80           C
ATOM   1899  C    LEU B2103     -19.314  24.486  30.577  1.00  7.45           C
ATOM   1900  O    LEU B2103     -19.177  23.580  29.756  1.00  5.72           O
ATOM   1901  CB   LEU B2103     -21.589  24.951  31.537  1.00  2.00           C
ATOM   1902  CG   LEU B2103     -22.694  24.551  32.512  1.00  2.00           C
ATOM   1903  CD1  LEU B2103     -23.659  25.697  32.675  1.00  2.04           C
ATOM   1904  CD2  LEU B2103     -23.417  23.318  32.012  1.00  2.00           C
ATOM   1905  H    LEU B2103     -19.988  25.662  33.421  0.00  0.00           H
ATOM   1906  N    TYR B2104     -18.594  25.602  30.530  1.00  6.39           N
ATOM   1907  CA   TYR B2104     -17.605  25.821  29.482  1.00  7.03           C
ATOM   1908  C    TYR B2104     -16.506  24.771  29.555  1.00  9.25           C
ATOM   1909  O    TYR B2104     -16.102  24.216  28.536  1.00 12.91           O
ATOM   1910  CB   TYR B2104     -16.987  27.215  29.602  1.00  7.14           C
ATOM   1911  CG   TYR B2104     -17.865  28.342  29.108  1.00  4.21           C
ATOM   1912  CD1  TYR B2104     -18.535  28.256  27.888  1.00  2.00           C
ATOM   1913  CD2  TYR B2104     -18.003  29.508  29.852  1.00  7.88           C
ATOM   1914  CE1  TYR B2104     -19.316  29.308  27.423  1.00  3.76           C
ATOM   1915  CE2  TYR B2104     -18.772  30.564  29.400  1.00  5.53           C
ATOM   1916  CZ   TYR B2104     -19.419  30.462  28.187  1.00  8.86           C
ATOM   1917  OH   TYR B2104     -20.122  31.548  27.727  1.00 12.11           O
ATOM   1918  H    TYR B2104     -18.814  26.319  31.162  0.00  0.00           H
```

Fig 4-33

```
ATOM   1919  HH   TYR B2104     -20.693  31.333  27.011  0.00   0.00           H
ATOM   1920  N    TYR B2105     -16.054  24.475  30.771  1.00  12.79           N
ATOM   1921  CA   TYR B2105     -15.030  23.452  30.996  1.00  10.70           C
ATOM   1922  C    TYR B2105     -15.479  22.070  30.515  1.00  10.02           C
ATOM   1923  O    TYR B2105     -14.702  21.307  29.942  1.00  11.77           O
ATOM   1924  CB   TYR B2105     -14.680  23.376  32.481  1.00   7.06           C
ATOM   1925  CG   TYR B2105     -13.496  22.488  32.765  1.00   4.50           C
ATOM   1926  CD1  TYR B2105     -12.288  22.693  32.111  1.00   8.17           C
ATOM   1927  CD2  TYR B2105     -13.579  21.446  33.684  1.00   6.11           C
ATOM   1928  CE1  TYR B2105     -11.184  21.892  32.360  1.00  12.33           C
ATOM   1929  CE2  TYR B2105     -12.472  20.629  33.946  1.00  12.32           C
ATOM   1930  CZ   TYR B2105     -11.276  20.866  33.279  1.00  15.17           C
ATOM   1931  OH   TYR B2105     -10.155  20.113  33.542  1.00  21.26           O
ATOM   1932  H    TYR B2105     -16.371  25.002  31.536  0.00   0.00           H
ATOM   1933  HH   TYR B2105      -9.397  20.447  33.059  0.00   0.00           H
ATOM   1934  N    HIS B2106     -16.746  21.759  30.737  1.00   9.87           N
ATOM   1935  CA   HIS B2106     -17.298  20.488  30.314  1.00  11.64           C
ATOM   1936  C    HIS B2106     -17.315  20.332  28.787  1.00  14.72           C
ATOM   1937  O    HIS B2106     -16.928  19.284  28.273  1.00  17.34           O
ATOM   1938  CB   HIS B2106     -18.705  20.326  30.881  1.00  15.15           C
ATOM   1939  CG   HIS B2106     -19.294  18.971  30.664  1.00  24.44           C
ATOM   1940  ND1  HIS B2106     -18.578  17.808  30.865  1.00  28.70           N
ATOM   1941  CD2  HIS B2106     -20.529  18.588  30.259  1.00  25.83           C
ATOM   1942  CE1  HIS B2106     -19.346  16.767  30.595  1.00  28.91           C
ATOM   1943  NE2  HIS B2106     -20.535  17.214  30.226  1.00  31.03           N
ATOM   1944  H    HIS B2106     -17.288  22.402  31.250  0.00   0.00           H
ATOM   1945  HD1  HIS B2106     -17.628  17.736  31.114  0.00   0.00           H
ATOM   1946  HE2  HIS B2106     -21.295  16.644  29.972  0.00   0.00           H
ATOM   1947  N    VAL B2107     -17.768  21.355  28.062  1.00  13.33           N
ATOM   1948  CA   VAL B2107     -17.797  21.281  26.599  1.00  10.31           C
ATOM   1949  C    VAL B2107     -16.384  21.294  26.009  1.00  10.92           C
ATOM   1950  O    VAL B2107     -16.047  20.456  25.172  1.00  11.27           O
ATOM   1951  CB   VAL B2107     -18.640  22.425  25.963  1.00   9.70           C
ATOM   1952  CG1  VAL B2107     -20.082  22.296  26.372  1.00  11.91           C
ATOM   1953  CG2  VAL B2107     -18.116  23.780  26.371  1.00  15.79           C
ATOM   1954  H    VAL B2107     -18.077  22.171  28.519  0.00   0.00           H
ATOM   1955  N    PHE B2108     -15.518  22.127  26.576  1.00   9.62           N
ATOM   1956  CA   PHE B2108     -14.109  22.164  26.187  1.00   8.05           C
ATOM   1957  C    PHE B2108     -13.423  20.810  26.364  1.00   9.13           C
ATOM   1958  O    PHE B2108     -12.685  20.368  25.493  1.00  10.33           O
ATOM   1959  CB   PHE B2108     -13.371  23.223  27.007  1.00   4.20           C
ATOM   1960  CG   PHE B2108     -11.923  23.366  26.651  1.00   2.00           C
ATOM   1961  CD1  PHE B2108     -10.961  22.606  27.295  1.00   3.42           C
ATOM   1962  CD2  PHE B2108     -11.519  24.292  25.702  1.00   4.15           C
ATOM   1963  CE1  PHE B2108      -9.613  22.760  27.000  1.00   9.05           C
ATOM   1964  CE2  PHE B2108     -10.170  24.461  25.396  1.00   8.79           C
ATOM   1965  CZ   PHE B2108      -9.214  23.692  26.045  1.00  12.56           C
ATOM   1966  H    PHE B2108     -15.849  22.771  27.234  0.00   0.00           H
ATOM   1967  N    ARG B2109     -13.609  20.198  27.528  1.00  11.74           N
ATOM   1968  CA   ARG B2109     -13.001  18.905  27.832  1.00  12.27           C
ATOM   1969  C    ARG B2109     -13.454  17.829  26.849  1.00  11.58           C
ATOM   1970  O    ARG B2109     -12.682  16.939  26.509  1.00  11.33           O
ATOM   1971  CB   ARG B2109     -13.358  18.476  29.256  1.00  18.36           C
ATOM   1972  CG   ARG B2109     -12.193  18.477  30.239  1.00  32.13           C
ATOM   1973  CD   ARG B2109     -11.939  17.082  30.819  1.00  43.37           C
ATOM   1974  NE   ARG B2109     -13.169  16.442  31.297  1.00  53.59           N
ATOM   1975  CZ   ARG B2109     -13.573  15.218  30.956  1.00  54.76           C
ATOM   1976  NH1  ARG B2109     -12.812  14.444  30.188  1.00  53.94           N
ATOM   1977  NH2  ARG B2109     -14.732  14.754  31.413  1.00  54.90           N
ATOM   1978  H    ARG B2109     -14.125  20.671  28.212  0.00   0.00           H
```

Fig 4-34

| | | | | | | | | | | |
|---|---|---|---|---|---|---|---|---|---|---|
| ATOM | 1979 | HE | ARG | B2109 | -13.738 | 16.951 | 31.910 | 0.00 | 0.00 | H |
| ATOM | 1980 | 1HH1 | ARG | B2109 | -11.931 | 14.776 | 29.851 | 0.00 | 0.00 | H |
| ATOM | 1981 | 2HH1 | ARG | B2109 | -13.130 | 13.529 | 29.944 | 0.00 | 0.00 | H |
| ATOM | 1982 | 1HH2 | ARG | B2109 | -15.288 | 15.321 | 32.021 | 0.00 | 0.00 | H |
| ATOM | 1983 | 2HH2 | ARG | B2109 | -15.033 | 13.832 | 31.173 | 0.00 | 0.00 | H |
| ATOM | 1984 | N | ARG | B2110 | -14.710 | 17.911 | 26.412 | 1.00 | 10.43 | N |
| ATOM | 1985 | CA | ARG | B2110 | -15.260 | 16.952 | 25.455 | 1.00 | 10.64 | C |
| ATOM | 1986 | C | ARG | B2110 | -14.810 | 17.200 | 24.014 | 1.00 | 12.51 | C |
| ATOM | 1987 | O | ARG | B2110 | -14.818 | 16.280 | 23.209 | 1.00 | 15.19 | O |
| ATOM | 1988 | CB | ARG | B2110 | -16.795 | 16.947 | 25.499 | 1.00 | 12.47 | C |
| ATOM | 1989 | CG | ARG | B2110 | -17.418 | 16.320 | 26.743 | 1.00 | 19.35 | C |
| ATOM | 1990 | CD | ARG | B2110 | -17.423 | 14.786 | 26.714 | 1.00 | 31.28 | C |
| ATOM | 1991 | NE | ARG | B2110 | -16.091 | 14.194 | 26.900 | 1.00 | 41.95 | N |
| ATOM | 1992 | CZ | ARG | B2110 | -15.762 | 13.332 | 27.865 | 1.00 | 41.41 | C |
| ATOM | 1993 | NH1 | ARG | B2110 | -16.633 | 13.017 | 28.820 | 1.00 | 36.79 | N |
| ATOM | 1994 | NH2 | ARG | B2110 | -14.534 | 12.815 | 27.899 | 1.00 | 36.39 | N |
| ATOM | 1995 | H | ARG | B2110 | -15.280 | 18.632 | 26.748 | 0.00 | 0.00 | H |
| ATOM | 1996 | HE | ARG | B2110 | -15.389 | 14.432 | 26.260 | 0.00 | 0.00 | H |
| ATOM | 1997 | 1HH1 | ARG | B2110 | -17.547 | 13.422 | 28.830 | 0.00 | 0.00 | H |
| ATOM | 1998 | 2HH1 | ARG | B2110 | -16.368 | 12.373 | 29.538 | 0.00 | 0.00 | H |
| ATOM | 1999 | 1HH2 | ARG | B2110 | -13.866 | 13.068 | 27.201 | 0.00 | 0.00 | H |
| ATOM | 2000 | 2HH2 | ARG | B2110 | -14.282 | 12.171 | 28.621 | 0.00 | 0.00 | H |
| ATOM | 2001 | N | ILE | B2111 | -14.494 | 18.447 | 23.670 | 1.00 | 14.35 | N |
| ATOM | 2002 | CA | ILE | B2111 | -14.033 | 18.769 | 22.314 | 1.00 | 18.50 | C |
| ATOM | 2003 | C | ILE | B2111 | -12.510 | 18.791 | 22.163 | 1.00 | 22.21 | C |
| ATOM | 2004 | O | ILE | B2111 | -11.963 | 19.586 | 21.395 | 1.00 | 27.42 | O |
| ATOM | 2005 | CB | ILE | B2111 | -14.644 | 20.117 | 21.784 | 1.00 | 14.09 | C |
| ATOM | 2006 | CG1 | ILE | B2111 | -14.044 | 21.333 | 22.500 | 1.00 | 13.58 | C |
| ATOM | 2007 | CG2 | ILE | B2111 | -16.148 | 20.108 | 21.982 | 1.00 | 19.97 | C |
| ATOM | 2008 | CD1 | ILE | B2111 | -14.821 | 22.615 | 22.301 | 1.00 | 2.00 | C |
| ATOM | 2009 | H | ILE | B2111 | -14.598 | 19.149 | 24.342 | 0.00 | 0.00 | H |
| ATOM | 2010 | N | SER | B2112 | -11.840 | 17.887 | 22.870 | 1.00 | 27.11 | N |
| ATOM | 2011 | CA | SER | B2112 | -10.410 | 17.634 | 22.673 | 1.00 | 32.50 | C |
| ATOM | 2012 | C | SER | B2112 | -10.155 | 16.126 | 22.525 | 1.00 | 35.63 | C |
| ATOM | 2013 | O | SER | B2112 | -10.552 | 15.361 | 23.432 | 1.00 | 36.42 | O |
| ATOM | 2014 | CB | SER | B2112 | -9.590 | 18.179 | 23.852 | 1.00 | 31.61 | C |
| ATOM | 2015 | OG | SER | B2112 | -9.589 | 19.601 | 23.899 | 1.00 | 28.34 | O |
| ATOM | 2016 | OXT | SER | B2112 | -9.613 | 15.712 | 21.474 | 1.00 | 41.38 | O |
| ATOM | 2017 | H | SER | B2112 | -12.312 | 17.230 | 23.418 | 0.00 | 0.00 | H |
| ATOM | 2018 | HG | SER | B2112 | -9.617 | 19.750 | 24.846 | 0.00 | 0.00 | H |
| TER | 2019 | | SER | B2112 | | | | | | |
| HETATM | 2020 | C1 | RAP | 108 | -6.816 | 26.014 | 40.365 | 1.00 | 5.94 | C |
| HETATM | 2021 | O1 | RAP | 108 | -7.715 | 26.739 | 39.504 | 1.00 | 6.16 | O |
| HETATM | 2022 | O2 | RAP | 108 | -5.659 | 25.863 | 39.953 | 1.00 | 4.69 | O |
| HETATM | 2023 | C2 | RAP | 108 | -7.234 | 25.472 | 41.742 | 1.00 | 2.10 | C |
| HETATM | 2024 | C3 | RAP | 108 | -6.748 | 24.038 | 41.963 | 1.00 | 2.00 | C |
| HETATM | 2025 | C4 | RAP | 108 | -7.531 | 22.968 | 41.204 | 1.00 | 2.86 | C |
| HETATM | 2026 | C5 | RAP | 108 | -9.027 | 23.085 | 41.430 | 1.00 | 2.00 | C |
| HETATM | 2027 | C6 | RAP | 108 | -9.492 | 24.485 | 41.139 | 1.00 | 2.08 | C |
| HETATM | 2028 | N7 | RAP | 108 | -8.685 | 25.389 | 41.985 | 1.00 | 3.45 | N |
| HETATM | 2029 | C8 | RAP | 108 | -9.287 | 26.223 | 42.852 | 1.00 | 2.80 | C |
| HETATM | 2030 | O3 | RAP | 108 | -8.653 | 27.066 | 43.484 | 1.00 | 4.16 | O |
| HETATM | 2031 | C9 | RAP | 108 | -10.645 | 26.309 | 43.120 | 1.00 | 3.33 | C |
| HETATM | 2032 | O4 | RAP | 108 | -11.026 | 25.607 | 44.055 | 1.00 | 2.89 | O |
| HETATM | 2033 | C10 | RAP | 108 | -11.647 | 27.189 | 42.361 | 1.00 | 7.35 | C |
| HETATM | 2034 | O5 | RAP | 108 | -11.749 | 26.675 | 41.029 | 1.00 | 5.80 | O |
| HETATM | 2035 | O6 | RAP | 108 | -12.815 | 27.195 | 43.206 | 1.00 | 7.04 | O |
| HETATM | 2036 | C11 | RAP | 108 | -11.102 | 28.623 | 42.177 | 1.00 | 5.50 | C |
| HETATM | 2037 | C12 | RAP | 108 | -12.102 | 29.453 | 41.362 | 1.00 | 2.25 | C |
| HETATM | 2038 | C13 | RAP | 108 | -12.661 | 28.755 | 40.117 | 1.00 | 3.81 | C |

Fig 4-35

```
HETATM 2039  C14 RAP   108     -12.744  27.225  40.197  1.00  5.55         C
HETATM 2040  C15 RAP   108     -12.476  26.558  38.844  1.00  6.36         C
HETATM 2041  C16 RAP   108     -13.491  26.688  37.700  1.00  7.22         C
HETATM 2042  O7  RAP   108     -14.764  26.288  38.070  1.00  6.77         O
HETATM 2043  C17 RAP   108     -13.020  25.794  36.553  1.00  7.17         C
HETATM 2044  C18 RAP   108     -12.702  26.344  35.400  1.00 12.19         C
HETATM 2045  C19 RAP   108     -12.183  25.694  34.165  1.00 14.38         C
HETATM 2046  C20 RAP   108     -12.264  26.351  33.003  1.00 13.32         C
HETATM 2047  C21 RAP   108     -11.719  25.829  31.760  1.00 10.57         C
HETATM 2048  C22 RAP   108     -10.967  26.472  30.890  1.00  7.17         C
HETATM 2049  C23 RAP   108     -10.527  25.696  29.671  1.00  3.85         C
HETATM 2050  C24 RAP   108      -9.009  25.760  29.546  1.00  5.00         C
HETATM 2051  C25 RAP   108      -8.217  25.354  30.783  1.00  6.28         C
HETATM 2052  C26 RAP   108      -6.853  26.023  30.751  1.00  9.09         C
HETATM 2053  O8  RAP   108      -5.913  25.475  30.185  1.00 17.77         O
HETATM 2054  C27 RAP   108      -6.684  27.414  31.356  1.00 14.08         C
HETATM 2055  O9  RAP   108      -5.514  27.884  30.789  1.00 14.20         O
HETATM 2056  C28 RAP   108      -6.426  27.335  32.858  1.00 13.28         C
HETATM 2057  O10 RAP   108      -5.394  26.369  33.097  1.00 17.10         O
HETATM 2058  C29 RAP   108      -7.657  26.973  33.703  1.00  7.79         C
HETATM 2059  C30 RAP   108      -7.814  25.804  34.281  1.00  5.36         C
HETATM 2060  C31 RAP   108      -8.914  25.353  35.171  1.00  5.26         C
HETATM 2061  C32 RAP   108      -8.560  25.557  36.644  1.00  8.61         C
HETATM 2062  O11 RAP   108      -8.235  24.591  37.334  1.00 12.38         O
HETATM 2063  C33 RAP   108      -8.639  26.961  37.262  1.00  6.28         C
HETATM 2064  C34 RAP   108      -7.455  27.273  38.205  1.00  7.20         C
HETATM 2065  C35 RAP   108      -7.353  28.808  38.512  1.00  4.56         C
HETATM 2066  C36 RAP   108      -6.618  29.542  37.393  1.00  6.95         C
HETATM 2067  C37 RAP   108      -5.242  29.057  36.926  1.00 11.47         C
HETATM 2068  C38 RAP   108      -4.839  29.836  35.667  1.00  9.55         C
HETATM 2069  C39 RAP   108      -3.488  29.508  35.015  1.00 14.00         C
HETATM 2070  O12 RAP   108      -3.117  30.527  34.126  1.00 21.91         O
HETATM 2071  C40 RAP   108      -2.354  29.491  36.072  1.00 15.37         C
HETATM 2072  O13 RAP   108      -1.167  28.920  35.507  1.00  6.26         O
HETATM 2073  C41 RAP   108      -2.766  28.682  37.309  1.00 13.80         C
HETATM 2074  C42 RAP   108      -4.078  29.130  37.914  1.00  9.01         C
HETATM 2075  C43 RAP   108     -10.856  29.287  43.527  1.00 10.83         C
HETATM 2076  C44 RAP   108     -12.882  24.304  36.817  1.00  5.39         C
HETATM 2077  C45 RAP   108     -11.166  26.303  28.459  1.00  2.00         C
HETATM 2078  C46 RAP   108      -8.066  23.836  30.825  1.00  4.71         C
HETATM 2079  C47 RAP   108      -8.663  28.083  33.806  1.00  2.00         C
HETATM 2080  C48 RAP   108      -9.109  23.870  34.864  1.00  3.40         C
HETATM 2081  C49 RAP   108      -8.736  29.425  38.657  1.00  2.00         C
HETATM 2082  C50 RAP   108     -15.819  26.946  37.457  1.00  2.69         C
HETATM 2083  C51 RAP   108      -5.711  28.919  29.903  1.00 21.98         C
HETATM 2084  C52 RAP   108      -4.002  31.014  33.140  1.00 21.11         C
HETATM 2085  HO6 RAP   108     -12.593  27.124  44.143  0.00  0.00         H
HETATM 2086  HO1 RAP   108      -4.969  26.537  33.948  0.00  0.00         H
HETATM 2087  HO3 RAP   108      -0.427  29.516  35.649  0.00  0.00         H
HETATM 2088  O   HOH   301     -13.963  32.282  39.005  1.00 20.07         O
HETATM 2089  1H  HOH   301     -14.436  33.059  39.326  0.00 20.00         H
HETATM 2090  2H  HOH   301     -13.909  31.701  39.771  0.00 20.00         H
HETATM 2091  O   HOH   302      -0.900  21.657  34.783  1.00 23.80         O
HETATM 2092  1H  HOH   302      -1.021  21.041  35.510  0.00 20.00         H
HETATM 2093  2H  HOH   302      -1.478  21.246  34.123  0.00 20.00         H
HETATM 2094  O   HOH   303      -6.938  34.185  40.131  1.00 41.17         O
HETATM 2095  1H  HOH   303      -6.199  34.542  39.638  0.00 20.00         H
HETATM 2096  2H  HOH   303      -6.527  33.918  40.941  0.00 20.00         H
HETATM 2097  O   HOH   304     -10.919  15.222  48.819  1.00 28.06         O
HETATM 2098  1H  HOH   304     -10.331  15.994  48.864  0.00 20.00         H
```

Fig 4-36

```
HETATM 2099  2H  HOH  304  -10.602  14.763  48.037  0.00  20.00      H
HETATM 2100  O   HOH  305  -21.400  35.769  26.707  1.00  26.77      O
HETATM 2101  1H  HOH  305  -21.139  35.329  27.513  0.00  20.00      H
HETATM 2102  2H  HOH  305  -22.356  35.778  26.710  0.00  20.00      H
HETATM 2103  O   HOH  306    0.813  27.087  37.460  1.00  15.38      O
HETATM 2104  1H  HOH  306    0.278  27.451  36.742  0.00  20.00      H
HETATM 2105  2H  HOH  306    0.156  26.516  37.895  0.00  20.00      H
HETATM 2106  O   HOH  307  -30.428  31.660  28.013  1.00  46.41      O
HETATM 2107  1H  HOH  307  -30.299  30.737  27.805  0.00  20.00      H
HETATM 2108  2H  HOH  307  -30.248  31.722  28.946  0.00  20.00      H
HETATM 2109  O   HOH  308   -4.519  32.837  47.558  1.00  15.92      O
HETATM 2110  1H  HOH  308   -4.435  32.964  48.515  0.00  20.00      H
HETATM 2111  2H  HOH  308   -4.287  31.920  47.465  0.00  20.00      H
HETATM 2112  O   HOH  309  -18.089  22.614  12.803  1.00  25.97      O
HETATM 2113  1H  HOH  309  -17.511  23.005  12.138  0.00  20.00      H
HETATM 2114  2H  HOH  309  -18.955  22.733  12.394  0.00  20.00      H
HETATM 2115  O   HOH  310  -22.152  21.619  36.180  1.00  41.59      O
HETATM 2116  1H  HOH  310  -22.437  22.341  36.738  0.00  20.00      H
HETATM 2117  2H  HOH  310  -22.872  21.464  35.569  0.00  20.00      H
HETATM 2118  O   HOH  311   -6.459   3.543  52.877  1.00  32.94      O
HETATM 2119  1H  HOH  311   -6.280   2.752  52.368  0.00  20.00      H
HETATM 2120  2H  HOH  311   -5.832   4.191  52.543  0.00  20.00      H
HETATM 2121  O   HOH  312   -5.993  11.471  28.804  1.00  18.59      O
HETATM 2122  1H  HOH  312   -6.909  11.725  28.881  0.00  20.00      H
HETATM 2123  2H  HOH  312   -5.782  11.031  29.653  0.00  20.00      H
HETATM 2124  O   HOH  313   -0.619  20.784  55.049  1.00  19.50      O
HETATM 2125  1H  HOH  313   -0.854  20.074  55.637  0.00  20.00      H
HETATM 2126  2H  HOH  313   -1.113  21.551  55.388  0.00  20.00      H
HETATM 2127  O   HOH  314   -5.598  26.321  58.876  1.00  36.20      O
HETATM 2128  1H  HOH  314   -6.497  26.108  58.602  0.00  20.00      H
HETATM 2129  2H  HOH  314   -5.118  25.491  58.861  0.00  20.00      H
HETATM 2130  O   HOH  315   -3.023  33.604  37.769  1.00  26.43      O
HETATM 2131  1H  HOH  315   -2.394  34.283  37.516  0.00  20.00      H
HETATM 2132  2H  HOH  315   -3.855  33.984  37.469  0.00  20.00      H
HETATM 2133  O   HOH  316  -25.006  29.561  22.950  1.00  41.75      O
HETATM 2134  1H  HOH  316  -24.532  29.047  23.605  0.00  20.00      H
HETATM 2135  2H  HOH  316  -25.677  28.934  22.652  0.00  20.00      H
HETATM 2136  O   HOH  317  -23.638  29.893  10.609  1.00  16.55      O
HETATM 2137  1H  HOH  317  -23.016  29.169  10.621  0.00  20.00      H
HETATM 2138  2H  HOH  317  -24.395  29.529  11.101  0.00  20.00      H
HETATM 2139  O   HOH  318   -7.744   6.880  50.272  1.00  20.83      O
HETATM 2140  1H  HOH  318   -7.080   6.901  49.564  0.00  20.00      H
HETATM 2141  2H  HOH  318   -7.480   6.116  50.785  0.00  20.00      H
HETATM 2142  O   HOH  319   -2.748   2.703  46.777  1.00  31.05      O
HETATM 2143  1H  HOH  319   -3.202   3.462  46.395  0.00  20.00      H
HETATM 2144  2H  HOH  319   -3.353   2.352  47.432  0.00  20.00      H
HETATM 2145  O   HOH  320  -19.295  42.654  40.303  1.00  39.42      O
HETATM 2146  1H  HOH  320  -19.042  41.825  39.876  0.00  20.00      H
HETATM 2147  2H  HOH  320  -18.638  43.269  39.991  0.00  20.00      H
HETATM 2148  O   HOH  321    0.583  32.369  55.901  1.00  39.29      O
HETATM 2149  1H  HOH  321   -0.191  32.008  55.428  0.00  20.00      H
HETATM 2150  2H  HOH  321    1.272  31.719  55.776  0.00  20.00      H
HETATM 2151  O   HOH  322  -16.781  17.874  51.246  1.00  33.48      O
HETATM 2152  1H  HOH  322  -17.172  18.545  50.688  0.00  20.00      H
HETATM 2153  2H  HOH  322  -15.838  18.064  51.228  0.00  20.00      H
HETATM 2154  O   HOH  323  -19.829  12.916  46.549  1.00  26.46      O
HETATM 2155  1H  HOH  323  -19.808  13.873  46.697  0.00  20.00      H
HETATM 2156  2H  HOH  323  -19.224  12.538  47.193  0.00  20.00      H
```

CRYSTALLINE FRAP COMPLEX

This is a divisional of application Ser. No. 08/735,848, filed on Oct. 23, 1996.

COPYRIGHT NOTICE

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates to a complex, in crystalline form, of two proteins, FKBP12 and the FRB domain of FRAP, in association with rapamycin, a small organic molecule to which the proteins bind. The crystalline form of this ternary complex is particularly useful for the determination of the three-dimensional structure of the complex at the atomic level. The three dimensional structure provides information useful for the design of pharmaceutical compositions which inhibit the biological function of proteins such as FRAP which contain an FRB domain, particularly those biological functions mediated by molecular interactions involving rapamycin or other compounds capable of binding to an FRB domain.

BACKGROUND

Rapamycin (sometimes called sirolimus) was first described in 1975 as an antifungal agent isolated from *Streptomyces hygroscopicus* (Vezina, 1975; Sehgal, 1975). In 1987, the structurally related compound FK506 (sometimes called tacrolimus) was characterized as a potent immunosuppressive agent (Tanaka, 1987), and shortly thereafter, rapamycin was also shown to have potent immunosuppressive activity. In spite of rapamycin's immunosuppressive activity and structural similarity to FK506, the two compounds suppress the immune response in completely different ways (Schreiber, 1992). FK506 inhibits the T cell receptor (TCR) signal and prevents activation of a resting helper T cell. Rapamycin inhibits the autocrine signaling pathway involving interleukin-2 (IL-2) and the IL-2 receptor (IL-2R). These latter signals commit the cell to a program of cell division by communicating with the components of the cell cycle machinery necessary for DNA replication.

Both FK506 and rapamycin are potentially useful in the treatment of human disease. FK506 has been approved by the FDA for use in treating the rejection of transplanted organs. A similar use has been envisioned for rapamycin, and its demonstrated activity in organ transplantation and autoimmune animal models indicate a high clinical potential. Rapamycin has been shown to have antitumor activity against B16 melanocarcinoma, colon 26 tumor, EM ependymoblastoma, CD8F1 mammary and colon 38 murine tumors (Sehgal, 1993). Rapamycin has also shown immunosuppressive activity in assays to measure prevention of development of autoimmune adjuvant arthritis, experimental allergic encephalomyelitis and autoimmune uveoretinitis in the rat (Sehgal, 1993).

The biological activity and structural novelty of both rapamycin and FK506 led to a search for their cellular target(s), and the target of both compounds was identified as the plentiful cytoplasmic protein FKBP12 (for FK506 binding protein) of 12 kDa molecular mass. Since FK506 and rapamycin bound to the same target (Kd of 0.4 and 0.2 nM, respectively) and affected different pathways, a new function was attributed to the FKBP12-ligand complex. This new function arises from the ability of FKBP12-FK506 and FKBP12-rapamycin complexes, but not the individual components, to bind to and inhibit still other protein targets. The FKBP12-FK506 complex inhibits the phosphatase activity of calcineurin, a crucial component of the TCR pathway. Calcineurin is a serine/threonine phosphatase also called PP2B. The FKBP12-rapamycin complex inhibits the IL-2R signal by binding to a large (289 kDa) protein named FRAP in humans (Brown et al, 1994) or RAFT in rats (Sabatini et al, 1994; Chiu et al, 1994).

The structural basis for the tight binding of FK506 and rapamycin by FKBP12 has been investigated by both X-ray diffraction and NMR techniques (Clardy, 1995). In particular, high resolution X-ray structures are available for FKBP12-FK506 (1.4 Å resolution) and FKBP12-rapamycin (1.7 Å resolution) (Van Duyne et al, 1991; Van Duyne et al, 1991a; Van Duyne et al, 1993). These structures reveal, among other things, the fold of FKBP12, the atomic details of the hydrophobic binding pocket, and the details of how FK506 and rapamycin interact with the binding pocket. A structural analysis of the complex formed between FKBP12-FK506-caldneurin is also available (Griffith et al, 1995). That structure reveals how the portion of FK506 not involved in binding FKBP12 interacts with calcineurin and inhibits its phosphatase activity.

The biochemical characterization of FRAP, the target of the FKBP12-rapamycin complex, remains incomplete. The C-terminal domain resembles a phosphatidylinositol (PI) kinase, but to date no PI or protein kinase activity has been convincingly demonstrated. FRAP (RAFT, TOR) are members of a rapidly growing and important family of proteins that have been identified only recently (Zakian, 1995). ATM, TEL1, DNA-PK and MEC1 are some of the recently characterized members of this family of PIK-related kinases. (See e.g., Keith, 1995). ATM (for ataxia telngiectasia mutant) is responsible for a human autosomal hereditary disease characterized by cerebellar degeneration, progressive mental retardation, uneven gait, dilation of blood vessels, immune deficiencies, premature aging and a hundredfold increase in cancer susceptibility (Zakian, 1995). Persons who are heterozygous in ATM are believed to be at elevated risk for cancer. Mutations to TEL1 lead to abnormally short telomeres, and in conjunction with other mutations can lead to sensitivity to X-rays, UV radiation and hydroxyurea. DNA-PK is, as the name suggests, a DNA-dependent protein kinase that recognizes damaged DNA, and human cells without DNA-PK activity are radiation sensitive and repair deficient. MEC1 is required for both S-M and G2-M checkpoint progression as well as for meiotic recombination in yeast. Thus MEC1 is arguably the master checkpoint gene in yeast.

FRAP is a large protein (2549 amino acid residues), and only a small fraction can be involved in recognizing the FKBP12-rapamycin complex. Fortunately all of these residues are in one domain, and this domain, which is called the FKBP12-rapamycin binding (FRB) domain, is the protein used in this invention. It was identified through tryptic digests of FRAP and independently produced as an 11 kDa soluble protein (Chen et al, 1995)

Unfortunately, until now, three-dimensional structural details of the association of FKBP12-rapamycin with the FRB domain of FRAP have remained completely unknown. In the absence of such three-dimensional structural details, it has been impossible to design compounds based on that structure which would be capable of mimicking rapamycin's binding to the FRB domain. We have now obtained crystals of that ternary complex and have determined its three dimensional structure. With this information, it is now possible for the first time to rationally design compounds capable of binding to an FRB domain and mimicking the pharmacological activity of rapamycin. Such mimics may be used in place of rapamycin as immunosuppressive agents or in other pharmacological applications.

SUMMARY OF THE INVENTION

This invention centers on the FRB domain of human FRAP and begins with obtaining crystals of human FKBP12-rapamycin-FRB of sufficient quality to determine the three dimensional (tertiary) structure of the complex by X-ray diffraction methods.

In considering our work, it should be appreciated that obtaining protein crystals in any case is a somewhat unpredictable art, especially in cases in which the practitioner lacks the guidance of prior successes in preparing and/or crystalizing any closely related proteins. Obtaining our first crystals of the ternary complex was therefore itself an unexpected result. In addition, our data represents the first detailed information available on the three dimensional structure of FRAP or of any of the PIK-related kinases and revealed an unpredicted array of surface features.

Our results are useful in a number of applications. As previously mentioned, the atomic details of how the FKBP12-rapamycin complex interacts with the FRB domain is essential for the structure-based design of rapamycin analogs. As noted above, rapamycin has several promising clinical indications, and improved rapamycin analogs would be useful therapeutic agents. This structure can be used as an essential starting point in predicting, via homology modeling, the structures of related proteins which contain homologous FRB domains, including other members of the PIK-related kinase family.

Furthermore, the structure shows—in atomic detail—how a small organic molecule, rapamycin, can be used to hold two proteins, FKBP12 and FRB, in close proximity. As such, this structure contains important lessons for the design of heterodimerizing agents.

Thus, the knowledge obtained concerning the FRB of FRAP can be used to model the tertiary structure of related proteins. By way of example, the structure of renin has been modeled using the tertiary structure of endothiapepsin as a starting point for the derivation. Model building of cercarial elastase and tophozoite cysteine protease were each built from known serine and cysteine proteases that have less than 35% sequence identity. The resultant models were used to design inhibitors in the low micromolar range. (*Proc. Natl. Acad. Sci.* 1993, 90, 3583). Furthermore, alternative methods of tertiary structure determination that do not rely on X-ray diffraction techniques and thus do not require crystallization of the protein, such as NMR techniques, are simplified if a model of the structure is available for refinement using the additional data gathered by the alternative technique. Thus, knowledge of the tertiary structure of the FRB region of FRAP provides a significant window to the structure of other proteins containing a homologous FRB domain, including the other PIK-related kinases.

Accordingly, one object of this invention is to provide a composition, in crystalline form, comprising a protein containing an FRB domain. The protein may have a bound ligand or may be part of a complex with a second protein molecule and a shared ligand. For instance, the crystalline composition may contain a complex containing a first protein having a peptide sequence derived or selected from that of an FKBP12 protein, e.g., human FKBP12; a second protein having a peptide sequence derived or selected from that of an FRB domain of a PIK-related kinase family member, e.g. the FRB domain of human FRAP; and a ligand such as rapamycin which is capable of binding to both proteins to form a ternary complex. Such a crystalline composition may contain one or more heavy atoms, e.g., one or more lead, mercury, gold and/or selenium atoms. Such a heavy atom derivative may be obtained, for example, by expressing a gene encoding the protein of interest under conditions permitting the incorporation of one or more heavy atom labels (e.g. as in the incorporation of selenomethionine), reacting the protein with a reagent capable of linking a heavy atom to the protein (e.g. trimethyl lead acetate) or soaking a substance containing a heavy atom into the crystals.

Preferred crystalline compositions of this invention are capable of diffracting x-rays to a resolution of better than about 3.5 Å, and more preferably to a resolution of 2.7 Å or better, and are useful for determining the three-dimensional structure of the material. (The smaller the number of angstroms, the better the resolution.)

Crystalline compositions of this invention specifically include those in which the crystals are characterized by the structural coordinates of the FRB protein set forth in the accompanying FIG. 4 or characterized by coordinates having a root mean square deviation therefrom, with respect to backbone atoms of amino acids listed in FIG. 4, of 1.5 Å or less. Furthermore, our crystalline compositions include crystals characterized by the structural coordinates of both the FRB and FKBP12 proteins set forth in FIG. 4, optionally including a molecule of rapamycin as defined structurally by the accompanying coordinates therefor.

Structural coordinates of a crystalline composition of this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. For example, data defining the three dimensional structure of a composition of this invention or a portion thereof containing an FRB domain-containing protein of the PIK-related kinase family, or portions or structurally similar homologues of such proteins, may be stored in a machine-readable storage medium, and may be displayed as a graphical three-dimensional representation of the protein structure, typically using a computer capable of reading the data from said storage medium and programmed with instructions for creating the representation from such data. This invention thus encompasses a machine, such as a computer, having a memory which contains data representing the structural coordinates of a crystalline composition of this invention, e.g. the coordinates set forth in FIG. 4, together with additional optional data and instructions for manipulating such data. Such data may be used for a variety of purposes, such as the elucidation of other related structures and drug discovery.

A first set of such machine readable data may be combined with a second set of machine, readable data using a machine programmed with instructions for using the first data set and the second data set to determine at least a portion of the coordinates corresponding to the second set of machine-readable data. For instance, the first set of data may comprise a Fourier transform of at least a portion of the coordinates for the complex set forth in FIG. 4, while the second data set may comprise X-ray diffraction data of a molecule or molecular complex.

More specifically, one of the objects of this invention is to provide three-dimensional structural information on the FRB domain of FRAP, of other members of the PIK-related kinase family which containg homologous FRB domains, and of homologs or variants thereof, preferably in association with a bound ligand or bound ligand:protein complex (such as FKBP12-rapamycin). To that end, we provide for the use of the structural coordinates of a crystalline composition of this invention, or portions thereof, to solve, e.g. by molecular replacement, the three dimensional structure of a crystalline form of another such protein, protein:ligand complex, or protein:ligand:protein complex. Doing so involves obtaining x-ray diffraction data for crystals of the protein or complex for which one wishes to determine the three dimensional structure. Then, one determines the three-dimensional structure of that protein or complex by analyzing the x-ray diffraction data using molecular replacement techniques with reference to the previous structural coordinates. As described in U.S. Pat. No. 5,353,236, for instance, molecular replacement uses a molecule having a known structure as a starting point to model the structure of an unknown crystalline sample. This technique is based on the principle that two molecules which have similar structures, orientations and positions in the unit cell diffract similarly. Molecular replacement involves positioning the known structure in the unit cell in the same location and orientation as the unknown structure. Once positioned, the atoms of the known structure in the unit cell are used to calculate the structure factors that would result from a hypothetical diffraction experiment. This involves rotating the known structure in the six dimensions (three angular and three spatial dimensions) until alignment of the known structure with the experimental data is achieved. This approximate structure can be fine-tuned to yield a more accurate and often higher resolution structure using various refinement techniques. For instance, the resultant model for the structure defined by the experimental data may be subjected to rigid body refinement in which the model is subjected to limited additional rotation in the six dimensions yielding positioning shifts of under about 5%. The refined model may then be further refined using other known refinement methods.

For example, one may use molecular replacement to exploit a set of coordinates such as set forth in FIG. 4 to determine the structure of a crystalline co-complex of the FRB domain, FKBP12 and a ligand other than rapamycin. Likewise one may use that same approach to determine the three dimensional structure of a complex of FKBP12, rapamycin and a protein containing a modified FRAP FRB domain or an FRB domain from a homolog of FRAP.

Another object of the invention is to provide a method for determining the three-dimensional structure of a protein containing an FRB domain, or a complex of the protein with a ligand therefor, using homology modeling techniques and structural coordinates for a composition of this invention. Homology modeling involves constructing a model of an unknown structure using structural coordinates of one or more related proteins, protein domains and/or subdomains. Homology modeling may be conducted by fitting common or homologous portions of the protein or peptide whose three dimensional structure is to be solved to the three dimensional structure of homologous structural elements. Homology modeling can include rebuilding part or all of a three dimensional structure with replacement of amino acids (or other components) by those of the related structure to be solved. The structural coordinates obtained for the related protein or complex may be stored, displayed, manipulated and otherwise used in like fashion as those for the ternary complex of FKBP12-rapamycin-FRB set forth in FIG. 4.

Crystalline compositions of this invention thus provide a starting material, and their three dimensional structure coordinates a point of reference, for use in solving the three-dimensional structure of other proteins containing an FRB domain homologous to that of FRAP, as well as complexes containing such a protein. Sequence similarity may be determined using any conventional similarity matrix. (See e.g. Dayhoff, 1979; Greer, 1981; and Gonnet, 1992). Proteins containing at least one FRB domain having at least 15% peptide sequence identity or similarity with respect to our FRB, as determined by any of the approaches described above, are considered FRAP homologs for the purpose of this disclosure.

By way of further example, the three dimensional structure defined by the machine readable data for the FRB domain (with or without the FKBP12 component) may be computationally evaluated for its ability to associate with various chemical entities. The term "chemical entity", as used herein, refers to chemical compounds, complexes of at least two chemical compounds, and fragments of such compounds or complexes.

For instance, a first set of machine-readable data defining the 3-D structure of FRAP or a FRAP homolog, or a portion or complex thereof, is combined with a second set of machine-readable data defining the structure of a chemical entity or moiety of interest using a machine programmed with instructions for evaluating the ability of the chemical entity or moiety to associate with the FRAP or FRAP homolog protein or portion or complex thereof and/or the location and/or orientation of such association. Such methods provide insight into the location, orientation and energetics of association of protein surfaces with such chemical entities.

Chemical entities that are capable of mimicking rapamycin's ability to associate with FRAP or a FRAP homolog should share part or all of rapamycin's pharmacologic activities, e.g. immunosuppressive activity, but may be designed for more convenient or economical preparation, improved pharmacokinetics, reduced side effects, etc. Such chemical entities therefore include potential drug candidates.

The three dimensional structure defined by the data may be displayed in a graphical format permitting visual inspection of the structure, as well as visual inspection of the association of the protein component(s) with rapamycin or other chemical entities. Alternatively, more quantitative or computational methods may be used. For example, one method of this invention for evaluating the ability of a chemical entity to associate with any of the molecules or molecular complexes set forth herein comprises the steps of: (a) employing computational means to perform a fitting operation between the chemical entity and a binding pocket or other surface feature of the molecule or molecular complex; and (b) analyzing the results of said fitting operation to quantify the association between the chemical entity and the binding pocket.

This invention further provides for the use of the structural coordinates of a crystalline composition of this invention, or portions thereof, to identify reactive amino acids, such as cysteine residues, within the three-dimensional structure, preferably within or adjacent to a ligand binding site; to generate and visualize a molecular surface, such as a water-accessible surface or a surface comprising the space-filling van der Waals surface of all atoms; to calculate and visualize the size and shape of surface features of the protein or complex, e.g., ligand binding pockets; to locate potential H-bond donors and acceptors within the three-dimensional structure, preferably within or adjacent to a ligand binding site; to calculate regions of hydrophobicity and hydrophilicity within the three-dimensional structure, preferably within or adjacent to a ligand binding site; and to calculate and visualize regions on or adjacent to the protein surface of favorable interaction energies with respect to selected functional groups of interest (e.g. amino, hydroxyl, carboxyl, methylene, alkyl, alkenyl, aromatic carbon, aromatic rings, heteroaromatic rings, etc.). One may use the foregoing approaches for characterizing the FRB domain-containing protein and its interactions with moieties of potential ligands to design or select compounds capable of specific covalent attachment to reactive amino acids (e.g., cysteine) and to design or select compounds of complementary characteristics (e.g., size, shape, charge, hydrophobicity/hydrophilicity, ability to participate in hydrogen bonding, etc.) to surface features of the protein, a set of which may be preselected. Using the structural coordinates, one may also predict or calculate the orientation, binding constant or relative affinity of a given ligand to the protein in the complexed state, and use that information to design or select compounds of improved affinity.

In such cases, the structural coordinates of the FRAP or FRAP homolog protein, or portion or complex thereof, are entered in machine readable form into a machine programmed with instructions for carrying out the desired operation and containing any necessary additional data, e.g. data defining structural and/or functional characteristics of a potential ligand or moiety thereof, defining molecular characteristics of the various amino acids, etc.

One method of this invention provides for selecting from a database of chemical structures a compound capable of binding to FRAP or a FRAP homolog. The method starts with structural coordinates of a crystalline composition of the invention, e.g., coordinates defining the three dimensional structure of FRAP or a FRAP homolog or a portion thereof or a complex thereof. Points associated with that three dimensional structure are characterized with respect to the favorability of interactions with one or more functional groups. A database of chemical structures is then searched for candidate compounds containing one or more functional groups disposed for favorable interaction with the protein based on the prior characterization. Compounds having structures which best fit the points of favorable interaction with the three dimensional structure are thus identified.

It is often preferred, although not required, that such searching be conducted with the aid of a computer. In that case a first set of machine-readable data defining the 3D structure of a FRAP or FRAP homolog protein, or a portion or protein-ligand complex thereof, is combined with a second set of machine readable data defining one or more moieties or functional groups of interest, using a machine programmed with instructions for identifying preferred locations for favorable interaction between the functional group (s) and atoms of the protein. A third set of data, i.e. data defining the location(s) of favorable interaction between protein and functional group(s) is so generated. That third set of data is then combined with a fourth set of data defining the 3D structures of one or more chemical entities using a machine programmed with instructions for identifying chemical entities containing functional groups so disposed as to best fit the locations of their respective favorable interaction with the protein.

Compounds having the structures selected or designed by any of the foregoing means may be tested for their ability to bind to FRAP or a FRAP homolog, inhibit the binding of FRAP or a FRAP homolog to a natural or non-natural ligand therefor (e.g. FKBP12-rapamycin, in the case of FRAP), and/or inhibit a biological function mediated by FRAP or the FRAP homolog.

This invention also permits methods for designing a compound capable of binding to a FRAP or FRAP homolog based on the three dimensional structure of bound rapamycin. One such method involves graphically displaying a three-dimensional representation based on coordinates defining the three-dimensional structure of a FRAP or FRAP homolog protein or a portion thereof complexed with a ligand such as the FKBP12:rapamycin complex. Interactions between portions of ligand and protein are characterized in order to identify candidate moieties of the ligand for replacement. One or more portions of the ligand which interact with the protein may be replaced with substitute moieties selected from a knowledge base of one or more candidate substitute moieties, and/or moieties may be added to the ligand to permit additional interactions with the protein. Compounds first identified by any of the methods described herein are also encompassed by this invention.

BRIEF DESCRIPTION OF THE DRAWINGS

FIGS. 4.1–4.60 depicts the atomic coordinates of the FKBP12:rapamycin:FRB complex obtained by X-ray diffraction studies of the crystals as discussed in detail in the Examples.

DETAILED DESCRIPTION OF THE INVENTION

Figure 1:
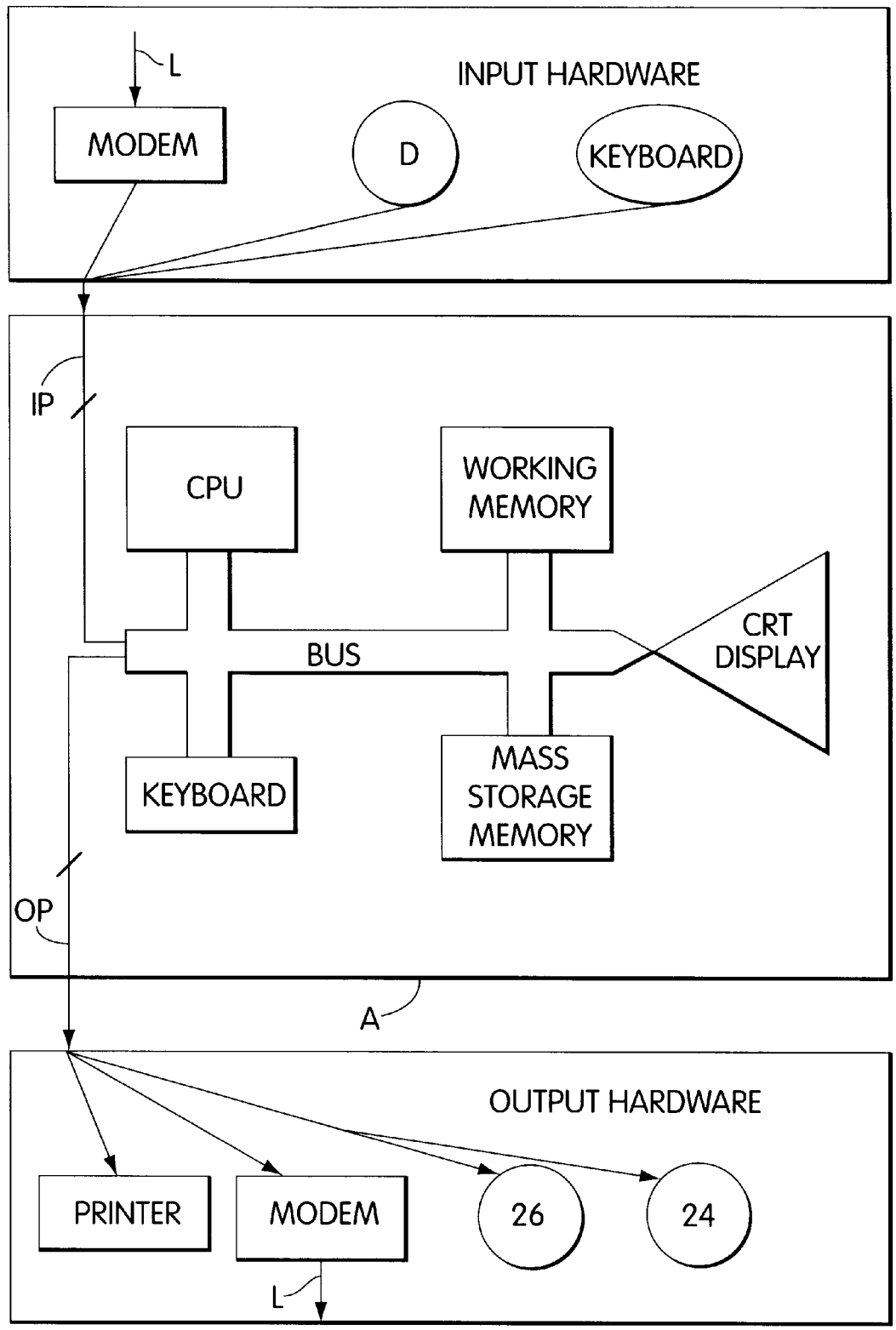
FIG. 1 depicts a computer system.

Despite the key role played by the FKBP12:rapamycin:FRAP complex in the IL-2/IL-2R signaling pathway, and despite the growing appreciation of the biological importance of the PIK-related kinase family, nothing was known of the three-dimensional architecture by which the FRB domain of FRAP (or of any FRAP homolog) engages the FKBP12:rapamycin complex required for its biological activity. X-ray crystallographic techniques could in principle address such issues. However, notwithstanding the key biological functions mediated by FRAP, there have been no reports disclosing that suitable crystals had been or could be obtained, let alone reports disclosing any x-ray crystallographic data or other information concerning the three-dimensional structure of any FRB domain. Even in the event that crystals had been obtained, then-available three-dimensional structural data relating to the FKBP12:rapamycin complex would not have been been sufficient for solving the ternary complex structure, at least in part, because the initial electron density maps wouldn't have permitted the chain of FRB to be traced. Even if parts of the chain could have been traced, they would not have refined under least-squares minimization techniques.

Nonetheless, we have succeeded in producing FKBP12 and FRAP FRB proteins, and have obtained crystals of their ternary complex with rapamycin. We have solved the three-dimensional structure of the crystalline complex using x-ray diffraction techniques. In view of our successes as disclosed herein, it can now be said that proteins comprising FRB domains can be produced in stable form, purified, and crystallized, and that their three-dimensional structures can be determined, all using materials and methods such as disclosed herein.

As mentioned elsewhere, FRAP is one of a number of PIK-related kinase family members that contain an FRB domain. PIK-related kinase family members share regions of homology including lipid kinase homologous regions, kinase domains and, in at least a number of cases, FRB domains. The presence and boundaries of homologous regions in a protein sequence can be identified by using a computer alignment program that identifies amino acid sequence homology to a known sequence or domain. For example, the FRB domain (amino acids 2015–2114) of FRAP may be used for such analysis, but FRB domains from other proteins such as RAPT or TOR1 or TOR2 can be used as well. The alignment method typically used by such programs is the Needleman-Wunch alignment. See e.g., "A General Method Applicable to the Search for Similarities in the Amino Acid Sequence of Two Proteins." Needlman, S. B.; Wunch, C. D. *J. Mol. Biol.* 1970, 48, 443–453.

We expressed the FRAP FRB domain as a glutathione-S-transferase (GST) fusion protein. The cDNA encoding residues 2015–2114 from human FRAP (Chen et al, 1995) was cloned into a pGEX vector and expressed in *E coli*, the resulting fusion protein was recovered and cleaved to yield the FRB protein which was then purified, all as described in detail below. FKBP12 protein was similarly obtained using a cDNA encoding residues 1–107 from human FKBP12 (Standaert et al, 1990, Nature 346: 671–674.

Other proteins containing an FRB domain may also be used, including larger FRAP fragments containing the FRB and flanking peptide sequence, including up to the entire FRAP protein. Additionally, FRB proteins can be prepared by analogous means containing homologous FRB regions from other proteins, including RAPT, TOR1, TOR2 or other members of the PIK-related kinase family. It should further be appreciated that other expression systems may be readily employed., including, e.g., materials and methods for expression in *E. coli* using T7, maltose-binding protein fusion (MBP), with epitope tags (His6, HA, myc, Flag) included or cleaved off. Baculoviral expression may be used, e.g. using pVL1393 or derivatives, for tFRB domain, fused (or not) to epitope tag or fusion partner such as GST. Conventional materials and methods for expression in mammalian, yeast or other cells may also be used.

Rapamycin may be prepared by known methods or may be obtained from commercial sources. Rapamycin analogs such as disclosed, e.g., in Luengo et al, 1995, Chemistry & Biology 2(7):471–481, may be used in place of rapamycin, in forming complexes of this invention.

Complex formation, crystallization, X ray diffraction experiments and interpretation of the diffraction data were conducted as described in detail in the Experimental Examples below. The resulting structural coordinates for a crystalline composition comprising FKBP12:rapamycin:FRB of FRAP (one molecule of complex per asymmetric unit) are set forth in Protein Database format in FIG. 4. Solving the X-ray crystal structure of the ternary complex allowed us to conduct the first three dimensional characterization of an FRB:ligand complex (viewing FKBP12:rapamycin as the "ligand"). The complex, depicted in schematic form in FIG. 3, involves an elaborate array of contacts between the two protein domains and their mutual small molecule ligand. This work reveals the first structural insights into an FRB domain-containing protein.

Structure of the Ternary Complex

The ternary complex of FKBP12-rapamycin-FRB has overall dimensions of 60 Å×45 Å×35 Å with the rapamycin sandwiched between FKBP12 and FRB. The FKBP12 structure is basically the same as in previously reported binary structures, with a five stranded anti parallel 5-sheet and a short α-helix. This binary structure was originally determined in the FKBP12-FK506 complex and later in the FKBP12-rapamycin complex (Van Duyne et al, 1993). The four helix bundle of FRB does not wrap around the effector site of FKBP12-rapamycin; it just touches the effector (i.e., FRB-binding) interface of the binary complex with few protein-protein interactions. All of the interactions between rapamycin and FRB are hydrophobic interactions, and protein-protein interactions between FKBP12 and FRB are limited to the 80 s loop and one side chain of the 40 s loop of FKBP12 (Table 2). The solvent accessible surface areas of FKBP12 and FRB are 5348 Å$^2$ and 5711 Å$^2$, respectively. Since the solvent accessible surface area of the FKBP12-FRB complex (protein only) is 10342 Å$^2$, binding results in a very modest 6% reduction of solvent accessible surface area. Two long side chains in the 40 s loop (Lys44 and Lys47) and three residues in the 80 s loop (Thr85, Gly86 and His87) of FKBP12 appear to make crucial contact in the ternary complex. In the FRB site, two residues at the end of α1 and the α1–α2 loop (Arg2042 and Tyr2038) contact the 80 s loop of FKBP12, and two residues in helix α4 (Tyr2105 and Asp2102) form direct or water-mediated hydrogen bonds to the 40 s loop of FKBP12. The loop-loop interaction between 80 s loop (FKBP12) and the α1–α2 loop (FRB) and the loop-helix interaction between 40 s loop (FKBP12) and helix α4 are the main protein-protein interactions in this ternary complex and thus contribute all of the protein-protein binding force forming the ternary complex.

Structure of FRB domain of FRAP

The FRB domain of the FRAP forms a typical four helix bundle, which is one of the most common structural motifs in globular proteins. The overall dimensions of this domain are 45 Å×30 Å×30 Å. All four helices (termed α1–α4) are connected with short underhand loops. The longest helix α3 (residues 2065–2091) has a bend at residue 2074 of 590. Except for a small bent part of α3 (residues 1065–2073), all four helices have similar lengths (16–19 residues, about 30 Å in length). The α2 helix also has a small bend around residues Glu2049, Val2050 and Leu2051 to form a $3_{10}$-helical turn rather than a normal α-helix. The angle between α1 and α2 is 22° and the angle between α3 and α4 is 20°. The angles between these pairs are in the range of 40–60°, which indicates that this four helix bundle is close to the 'X' type interhelical

TABLE 1

Intra-molecular hydrogen bonds and close contacts in the ternary complex

Inter-helical interactions in the FRB domain of FRAP

| | | | | Distance (Å) |
|---|---|---|---|---|
| His 2055 (α2) | Nε2 | Tyr 2104 (α4) | OH | 2.85 |
| His 2028 (α1) | Nε2 | Ser 2112 (C terminal) | Oγ | 3.23 |

TABLE 1-continued

Intra-molecular hydrogen bonds and close contacts in the ternary complex

Close contacts of rapamycin and FRB domain of FRAP

| Rapamycin | FRB domain of FRAP | | Distance (Å) |
|---|---|---|---|
| C50 | Thr 2098 | O | 3.13 |
| C27 | Ser 2035 | Oγ | 3.39 |
| C51 | Ser 2035 | Oγ | 3.38 |

Interactions of FKBP12 and FRB domain of FRAP

| FKBP12 | | FRB domain of FRAP | | Distance (Å) |
|---|---|---|---|---|
| Lys 47 | O | Tyr 2105 | OH | 2.56 |
| Thr 85 | Oγ1 | Arg 2042 | NH1 | 3.10 |
| Thr 85 | Oγ1 | Arg 2042 | NH2 | 2.88 |
| Gly 86 | O | Arg 2042 | NH2 | 2.79 |
| His 87 | Nε2 | Tyr 2038 | OH | via H$_2$O 301 |
| His 87 | Nδ1 | Arg 2042 | NH2 | via H$_2$O 303 |
| Lys 44 | Nζ | Asp 2102 | Oδ1 | via H$_2$O 310 | pattern which is the alternating pattern of parallel and perpendicular helix-helix interactions (Harris et al, 1994). As usual, most of the hydrophobic and aromatic residues are located in the inter-helical interface and most of the hydrophilic residues are in the outside of the bundle, which is exposed to the solvent. Only two strong hydrogen bonds were found for the inter-helical interactions (Table 1) and could be key interactions maintaining the overall conformation of the four helix bundle. Helices α1 and α4, which have an interhelical angle of 44°, form a deep cleft on the molecular surface of this domain. This cleft is surrounded by six aromatic side chains forming the 'aromatic pocket' which has exquisite steric complementary for the rapamycin effector domain binding.

Structure of FKBP12-rapamycin

The structure of FKBP12 in the ternary complex is basically the same as that in the binary complex of FKBP12-rapamycin or FKBP12-FK506. The protein fold and the architecture of the secondary structure are exactly the same as in the binary complex, and the interaction with rapamycin is also the same as that of the binary complex. The overall r.m.s. deviation between the FKBP12 in the ternary complex and that in the FKBP12-rapamycin complex is 1.14 Å (0.49 Å for the main chain), and the deviation between FKBP12 in the ternary complex and that in the FKBP12-FK506 complex is 1.11 Å (0.48 Å for the main chain), which implies that binding of FKBP12:rapamycin to the FRAP FRB domain is not accompanied by significant changes in the conformation of the FRB binding site on FKBP12 or of the effector domain of rapamycin. Even the 40 s loop and 80 s loop regions in the FKBP12, that have direct interaction to the FRB domain, are not significantly different in 3D structure from that seen in the binary complexes. These r.m.s. values were calculated by the rigid-body fitting on the main chain atoms in the FKBP12 using QUANTA. The overlay of FKBP12-FK506 to the ternary complex clearly confirmed the fact that FKBP12-FK506 complex can't bind FRAP as FK506's effector region does not extend enough. The protein-protein interactions by themselves between FKBP12 and FRB are not enough for the formation of a binary complex; rapamycin is essential to mediate the interaction of the two proteins.

FKBP12-rapamycin binding to FRAP

While the interactions of rapamycin with FRB are all hydrophobic, rapamycin-FKBP12 interactions employ five hydrogen bonds which are the same found in the binary complex of FKBP12-rapamycin, to govern this interaction. Rapamycin is surrounded by five conserved aromatic residues in FKBP12, which makes the binding pocket for the rapamycin a complete 'aromatic pocket' along with six aromatic residues in FRB domain. Comparing the sequence of these aromatic residues of FRB domain with other FKBP-rapamycin target proteins, these six aromatic residues are all conserved in RAFT (Sabatini et al, 1994), TOR1, and TOR2 (Stan, et al, 1994)—suggesting that these structural results will be applicable to other members of the PIK-related kinase family. It is expected that binding domains of these other proteins have a similar structure with FRB domain. For the interaction between rapamycin and FRB domain, two major sites on FRB are considered crucial for rapamycin binding. Ser2035, which is also conserved in other FKBP12-rapamycin target proteins, has close contact with C27 and C51 of rapamycin (Table 2). The other site is Thr2098 which has a close contact with C50 of rapamycin. C50 of the rapamycin is at the end of C16 methoxy group, which has been a key target for substituted analogs. All of the hydrophobic interactions between rapamycin and FRB including Ser2035 and Thr2098 can be considered as the main force contributing to complete ternary complex.

Mutational studies

Ser2035 in FRB has been the major site for the site-directed mutation studies of FRAP (Chen et al, 1995). Those studies revealed that the substitution of this residue to other residues larger than alanine abolish binding affinity toward FKBP12-rapamycin. The crystal structure of the ternary complex shows the direct effect of steric hindrance when this position is substituted by longer side chains. It has been suggested that this conserved serine site is a phosphorylation site, and phosphorylation would abrogate binding. By the binding of FKBP12-rapamycin, this serine site, which is open to the solvent when unbound, is protected from phosphorylation and this probably causes the inhibition of the downstream of the signaling pathway.

For rapamycin, C16 has been the main site for substitution in published structure-activity studies (Luengo et al, 1995). The studies of C16 analogs of rapamycin showed that the bulky group substitutions on this position have lower affinity for the FKBP12 binding and lower activity. However some analogs with different stereochemistry or different groups showed retained activity and affinity to FKBP12. Such C-16 substituted analogs could be of therapeutic use.

Applications of the invention

This invention encompasses crystalline compositions containing FRAP or a FRAP homolog protein or portion thereof having a region characterized by structural coordinates of the FRB domain set forth in FIG. 4, or by coordinates having a root mean square deviation therefrom of less than about 1.5 Å, preferably less than about 1 Å, and even more preferably less than about 0.5 Å, with respect to backbone atoms of amino acid residues listed there.

As practitioners in this art will appreciate, various computational analyses may be used to determine the degree of similarity between the three dimensional structure of a given protein (or a portion or complex thereof) and FRAP or a FRAP homolog protein or portion (e.g. the FRB domain) or complex thereof such as are described herein. Such analyses may be carried out with commercially available software applications, such as the Molecular Similarity application of QUANTA (Molecular Simulations Inc., Waltham, Mass.) version 3.3, and as described in the accompanying User's Guide, Volume 3 pgs. 134–135.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we define equivalent atoms as protein backbone atoms (N, Cα, C and O) for all conserved residues between the two structures being compared and consider only rigid fitting operations.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any set of structural coordinates of a FRAP or FRAP homolog protein, portion of a FRAP or FRAP homolog protein or molecular complex thereof that has a root mean square deviation of conserved residue backbone atoms (N, Cα, C, O) of less than 1.5 Å when superimposed-using backbone atoms-on the relevant structural coordinates of a protein or complex of this invention, e.g. the coordinates listed in FIG. 4, are considered identical. More preferably, the root mean square deviation is less than 1.0 Å. Most preferably, the root mean square deviation is less than 0.5 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of a protein of this invention, such as the FRB of FRAP, as defined by the structural coordinates of FIG. 4 and described herein.

The term "least squares" refers to a method based on the principle that the best estimate of a value is that in which the sum of the squares of the deviations of observed values is a minimum.

In order to use the structural coordinates generated for a crystalline substance of this invention, e.g. the structural coordinates of the FRB of FRAP set forth in FIG. 4, it is often necessary or desirable to display them as, or convert them to, a three-dimensional shape, or to otherwise manipulate them. This is typically accomplished by the use of commercially available software such as a program which is capable of generating three-dimensional graphical representations of molecules or portions thereof from a set of structural coordinates.

By way of illustration, a non-exclusive list of computer programs for viewing or otherwise manipulating protein structures include the following:

| | |
|---|---|
| Midas (Univ. of California, San Francisco) | X-Plor |
| MidasPlus (Univ. of Cal., San Francisco) | (Molecular Simulations, Inc.; Yale Univ.) |
| MOIL (University of Illinois) | Spartan (Wavefunction, Inc.) |

-continued

| | |
|---|---|
| Yummie (Yale University) | Catalyst(Molecular Simulations, Inc.) |
| Sybyl (Tripos, Inc.) | Molcadd(Tripos, Inc.) |
| Insight/Discover(Biosym Technologies) | VMD(Univ. of Illinois/ Beckman Institute) |
| MacroModel(Columbia University) | Sculpt(Interactive Simulations, Inc.) |
| Quanta(Molecular Simulations, Inc.) | Procheck(Brookhaven Nat'l Laboratory) |
| Cerius(Molecular Simulations, Inc.) | DGEOM(QCPE) |
| Alchemy(Tripos, Inc.) | RE__VIEW(Brunel University) |
| LabVision(Tripos, Inc.) | Modellar(Birbeck Col., Univ. of London) |
| Rasmol(Glaxo Research and Development) | Xmol(Minnesota Super- computing Center) |
| Ribbon(University of Alabama) | Protein Expert(Cambridge Scientific) |
| NAOMI(Oxford University) | HyperChem(Hypercube) |
| Explorer Eyechem(Silicon Graphics, Inc.) | MD Display(University of Washington) |
| Univision(Cray Research) | PKB |
| Molscript(Uppsala University) | (Nat'l Center for Biotech. Info., NIH) |
| Chem-3D(Cambridge Scientific) | ChemX(Chemical Design, Ltd.) |
| Chain(Baylor College of Medicine) | Cameleon(Oxford Molecular, Inc.) |
| O(Uppsala University) | Iditis(Oxford Molecular, Inc.) |
| GRASP(Columbia University) | |

For storage, transfer and use with such programs of structural coordinates for a crystalline substance of this invention, a machine-readable storage medium is provided comprising a data storage material encoded with machine readable data which, when using a machine programmed with instructions for using said data, e.g. a computer loaded with one or more programs of the sort identified above, is capable of displaying a graphical three-dimensional representation of any of the molecules or molecular complexes described herein. Machine-readable storage media comprising a data storage material include conventional computer hard drives, floppy disks, DAT tape, CD-ROM, and other magnetic, magneto-optical, optical, floptical and other media which may be adapted for use with a computer.

Figure 3:
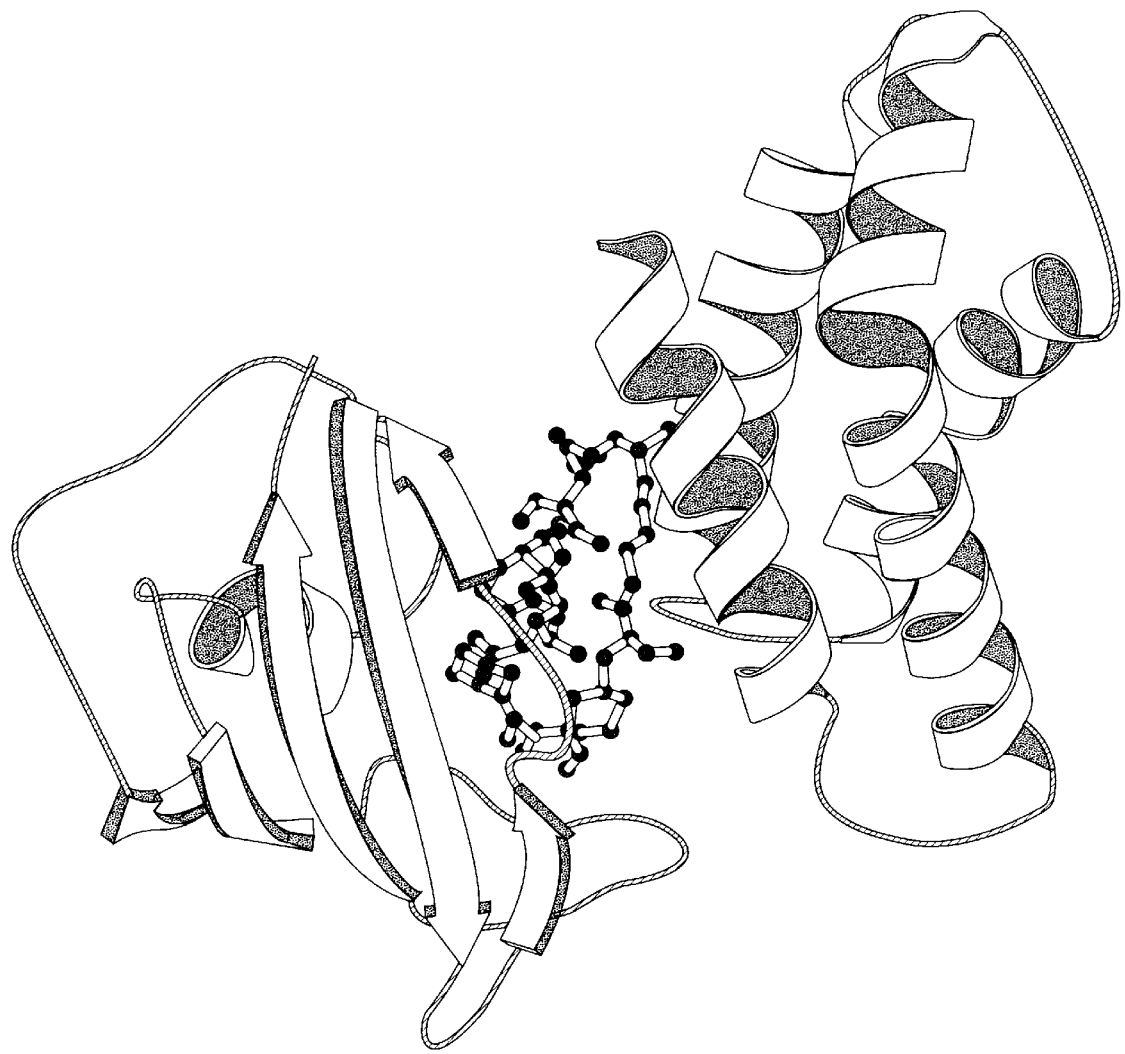
FIG. 3 depicts a ribbon diagram of the three dimensional structure of the FKBP12:rapamycin:FRB domain complex, as defined by the coordinates of FIG. 4.

Even more preferred is a machine-readable data storage medium that is capable of displaying a graphical three-dimensional representation of a molecule or molecular complex that is defined by the structural coordinates of a complex, FRB-containing protein component thereof, or portion thereof, comprising structural coordinates of an FRB domain such as the FRAP FRB coordinates set forth in our attached FIG. 4 ± a root mean square deviation from the conserved backbone atoms of the amino acids thereof of not more than 1.5 Å. An illustrative embodiment of this aspect of the invention is a conventional 3.5" diskette, DAT tape or hard drive encoded with a data set, preferably in PDB format, comprising the coordinates of our FIG. 4. FIG. 3 illustrates a printout of a graphical three-dimensional representation of such a complex.

In another embodiment, the machine-readable data storage medium comprises a data storage material encoded with a first set of machine readable data which comprises the Fourier transform of the structural coordinates set forth in FIG. 4 (or again, a derivative thereof), and which, when using a machine programmed with instructions for using said data, can be combined with a second set of machine readable data comprising the X-ray diffraction pattern of a molecule or molecular complex to determine at least a portion of the structural coordinates corresponding to the second set of machine readable data.

FIG. 1 illustrates one version of these embodiments. The depicted system includes a computer A comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines (IP), and one or more output lines (OP), all of which are interconnected by a conventional bidirectional system bus.

Input hardware B, coupled to computer A by input lines, may be implemented in a variety of ways. Machine-readable data of this invention may be inputted via the use of a modem or modems connected by a telephone line or dedicated data line L. Alternatively or additionally, the input hardware may comprise CD-ROM drives or disk drives D. In conjunction with the CRT display terminal, a keyboard may also be used as an input device.

Output hardware, coupled to computer A by output lines, may similarly be implemented by conventional devices. By way of example, output hardware may include a CRT display terminal for displaying a graphical representation of a protein of this invention (or portion thereof) using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Examples of such programs are discussed in reference to the computational methods of drug discovery as described herein. Specific references to components of the hardware system of FIG. 1 are included as appropriate throughout the following description of the data storage medium.

Figure 2A:
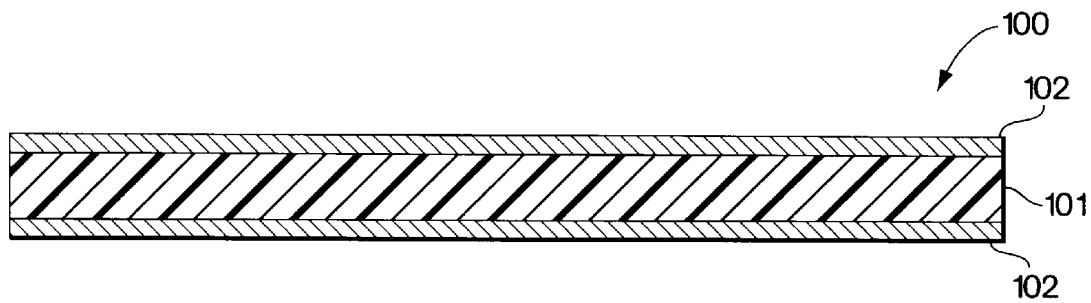
FIG. 2 depicts storage media of this invention.

FIG. 2A shows a cross section of a magnetic data storage medium 100 which can be encoded with a machine-readable data that can be carried out by a system such as a system of FIG. 1. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in a manner which may be conventional, machine readable data such as that described herein, for execution by a system such as a system of FIG. 1.

Figure 2B:
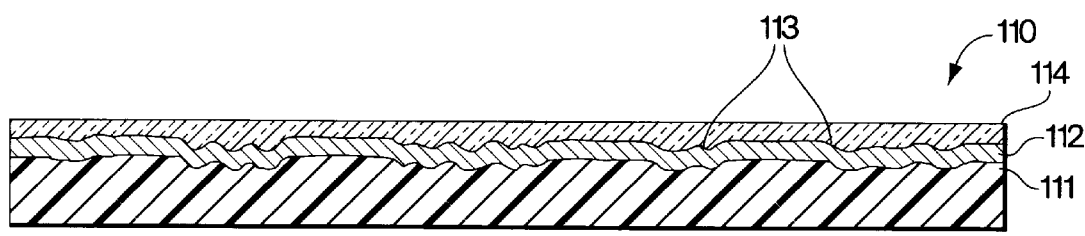

FIG. 2B shows a cross section of an optically-readable data storage medium 110 which also can be encoded with such machine-readable data, or set of instructions, which can be carried out by a system such as a system of FIG. 1. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Use of Structure in Drug Discovery

The availability of the three-dimensional structure of the ternary complex of FKBP12:rapamycin:FRB of FRAP makes structure-based drug discovery approaches possible. Structure-based approaches include de Novo molecular design, computer-aided optimization of lead molecules, and computer-based selection of candidate drug structures based on structural criteria.

Rapamycin mimetics may be developed from the bound conformation of rapamycin by design, by searching databases for replacements of one or more structural segments of rapamycin, or by enhancement of existing ligand-protein interactions (i.e., by replacing a component moiety of a ligand with a substitute moiety capable of greater interaction with the target protein, whether through accessible protein contact points or by extrusion of otherwise sequestered waters). Knowledge of the bound conformation of a ligand can suggest avenues for conformational restriction and replacement of atoms and/or bonds of rapamycin. A less biased approach involves computer algorithms for searching databases of three dimensional structures to identify replacements for one or more portions of the ligand. By this method, one can generate compounds for which the bioactive conformation is heavily populated, i.e., compounds which are based on particularly biologically relevant conformations of the ligand. Algorithms for this purpose are implemented in programs such as Cast-3D (Chemical Abstracts Service), 3DB Unity (Tripos, Inc.), Quest-3D (Cambridge Crystallographic Data Center), and MACCS/ISIS-3D (Molecular Design Limited). These geometric searches can be augmented by steric searching, in which the size and shape requirements of the binding site are used to weed out hits that have prohibitive dimensions. Programs that may be used to synchronize the geometric and steric requirements in a search applied to the FRB of FRAP include CAVEAT (P. Bartlett, University of California, Berkeley), HOOK (MSI), ALADDIN (Daylight Software) and DOCK (I.D. Kuntz, University of California, San Francisco; see e.g. http://www.cmpharm.ucsf.edu/kuntz-/kuntz.html and references cited therein). All of these searching protocols may be used in conjunction with existing corporate databases, the Cambridge Structural Database, or available chemical databases from chemical suppliers.

Characterization of Compounds

Compounds designed, selected and/or optimized by methods described above may be evaluated for binding activity with respect to proteins containing one or more FRB domains using various approaches, a number of which are well known in the art. For instance, compounds may be evaluated for activity as competitive inhibitors of the binding of a natural ligand for the FRB, e.g. FKBP12:rapamycin in the case of the FRAP FRB. Competitive inhibition may be determined using any of the numerous available technologies known in the art.

Such compounds may be further evaluated for activity in inhibiting cellular or other biological events mediated by a pathway involving the interaction of interest using a suitable cell-based assay or an animal model. Cell-based assays and animal models suitable for evaluating inhibitory actvity of a compound with respect to a wide variety of cellular and other biological events are known in the art. New assays and models are regularly developed and reported in the scientific literature.

For example, compounds which mimic the binding of rapamycin or FKBP12:rapamycin with respect to FRAP may be evaluated for biological activity in the mouse spelocyte mitogenesis assay or the high-flux yeast-based assay of Luengo et al, supra. A battery of in vivo models may be used to profile the breadth of the compound's immunosuppressive (or other) activity and compare the profile to those of positive controls such as rapamycin itself. Comparisons may also be made to other currently accepted immunosuppressive compounds, e.g. cyclophosphamide, and leflunomide. Initial in vivo screening models include: Delayed type hypersensitivity testing, Allogeneic skin transplantation, and Popliteal lymph iode hyperplasia. Compounds demonstrating optimal profiles in the above models are advanced into more sophisticated models designed to confirm immunosuppressive activity in specific therapeutic areas including: Rheumatoid arthritis, Transplantation, Graft vs. host disease, and Asthma.

By way of further illustration, compounds may be evaluated in relevant conventional in vitro and in vivo assays for inhibition of the initiation, maintenance or spread of cancerous growth. See e.g., Ishii et al., J. Antibiot. XLII:1877–1878 (1989) (in vitro evaluation of cytotoxic/ antitumor activity); Sun et al, U.S. Pat. No. 5,206,249 (issued 27 Apr. 1993) (in vitro evaluation of growth inhibitory activity on cultured leukemia cells); and Sun et al, supra (xenograft models using various human tumor cell lines xenografted into mice, as well as various transgenic animal models).

Single and multiple (e.g., 5 to 7 days) dose investigative toxicology studies are typically performed in the efficacy test species using the intended route of administration for the efficacy study. These investigative toxicology studies are performed to identify maximum tolerated dose, subjective bioavailability from the intraperitoneal or oral routes of administration, and estimation of an initial safety margin. Initial bioavailability and pharmacokinetics (blood clearance) of the compounds may be determined, with standard cold or radioactive assay methods, to assist in defining appropriate dosing regimens for the compounds in the animal models.

Pharmaceutical Compositions and Uses of rapamycin mimetics and other FRAP-binding compounds Compounds which bind to an FRB domain may be used as biological reagents in binding assays as described herein for functional classification of members of the PIK-related kinase family, particularly newly discovered proteins, based on ligand specificity.

Moreover, compounds identified as described above can be used for their immunosuppressive or other pharmacologic activity in place of rapamycin.

A compound selected or identified in accordance with this invention can be formulated into a pharmaceutical composition containing a pharmaceutically acceptable carrier and/ or other excipient(s) using conventional materials and means. Such a composition can be administered as an immunosuppresant, for example, to an animal, either human or non-human. Administration of such composition may be by any conventional route (parenteral, oral, inhalation, and the like) using appropriate formulations as are well known in this art. The compound can be employed in admixture with conventional excipients, i.e., pharmaceutically acceptable organic or inorganic carrier substances suitable for parenteral administration.

Pharmaceutical applications

By virtue of its capacity to mimic the interaction of rapamycin with FRAP, a compound identified as described herein may be used in pharmaceutical compositions and methods for treatment or prevention of various diseases and disorders in a mammal in need thereof.

Mammals include rodents such as mice, rats and guinea pigs as well as dogs, cats, horses, cattle, sheep, non-human primates and humans.

The preferred method of such treatment or prevention is by administering to a mammal an effective amount of the compound to prevent, alleviate or cure said disease or disorder. Such effective amounts can be readily determined by evaluating the compounds of this invention in conventional assays well-known in the art, including assays described herein.

Therapeutic/Prophylactic Administration & Pharmaceutical Compositions

The invention provides methods of treating, preventing and/or alleviating the symptoms and/or severity of an untoward immune response or other disease or disorder referred to above by administration to a subject of a in an amount effective therefor. The subject will be an animal, including but not limited to animals such as cows, pigs, chickens, etc., and is preferably a mammal, and most preferably human.

Various delivery systems are known and can be used to administer the compound, e.g., encapsulation in liposomes, micropartides, microcapsules, etc. One mode of delivery of interest is via pulmonary administration, as detailed more fully infra. Other methods of introduction include but are not limited to intradermal, intramuscular, intraperitoneal, intravenous, subcutaneous, intranasal, epidural and oral routes. The compound may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In specific embodiments, it may thus be desirable to administer the compound locally to the area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

This invention also provides pharmaceutical compositions. Such compositions comprise a therapeutically (or prophylactically) effective amount of the compound, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary.

In addition, in certain instances, it is expected that the compound may be disposed within devices placed upon, in, or under the skin. Such devices include patches, implants, and injections which release the compound into the skin, by either passive or active release mechanisms. Materials and methods for producing the various formulations are well known in the art [see e.g. U.S. Pat. Nos. 5,182,293 and 4,837,311 (tablets, capsules and other oral formulations as well as intravenous formulations)].

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of the compound which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level of the compound, as the active component(s), should be determined as in the case of all pharmaceutical treatments, by the attending physician or other health care provider and will depend upon well known factors, including route of administration, and the age, body weight, sex and general health of the individual; the nature, severity and clinical stage of the disease; and the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Pulmonary Administration

In one embodiment of this invention, the compound is administered by pulmonary administration, e.g. via aerosolization. This route of administration may be particularly useful for treatment or prophylaxis of bronchial or pulmonary infection or tumors.

Pulmonary administration can be accomplished, for example, using any of various delivery devices known in the art (see e.g., Newman, S. P., 1984, in Aerosols and the Lung, Clarke and Davia (eds.), Butterworths, London, England, pp. 197–224; PCT Publication No. WO 92/16192 dated Oct. 1, 1992; PCT Publication No. WO 91/08760 dated Jun. 27, 1991; NTIS Patent Application 7-504-047 filed Apr. 3, 1990 by Roosdorp and Crystal), including but not limited to nebulizers, metered dose inhalers, and powder inhalers. Various delivery devices are commercially available and can be employed, e.g., Ultravent nebulizer (Mallinckrodt, Inc., St. Louis, Mo.); Acorn II nebulizer (Marquest Medical Products, Englewood, Colo.), Ventolin metered dose inhaler (Glaxo Inc., Research Triangle Park, N.C.); Spinhaler powder inhaler (Fisons Corp., Bedford, Mass.) or Turbohaler (Astra). Such devices typically entail the use of formulations suitable for dispensing from such a device, in which a propellant material may be present.

Ultrasonic nebulizers tend to be more efficient than jet nebulizers in producing an aerosol of respirable size from a liquid (Smith and Spino, "Pharmacokinetics of Drugs in Cystic Fibrosis," Consensus Conference, Clinical Outcomes for Evaluation of New CF Therapies, Rockville, Md., Dec. 10–11, 1992, Cystic Fibrosis Foundation).

A nebulizer may be used to produce aerosol particles, or any of various physiologically acceptable inert gases may be used as an aerosolizing agent. Other components such as physiologically acceptable surfactants (e.g., glycerides), excipients (e.g., lactose), carriers, and diluents may also be included.

This invention is not to be limited in scope by the specific embodiments described herein. Indeed, various modifications of the invention in addition to those described herein will become apparent to those skilled in the art from the foregoing description. Such modifications are intended to fall within the the scope of the appended claims.

Various patents, patent applications and publications are cited herein, the disclosures of which are incorporated by reference in their entireties.

EXPERIMENTAL EXAMPLES

I. Protein Preparation cDNAs encoding human FKBP12 (Standaert et al, 1990) and the 12-kDa FRAP fragment containing the FRB domain (Chen et al, 1995) (FRAP12) were subcloned into pGEX-2T (Pharmacia) for the expression of GST-FKBP12 and GST-FRAP12 fusion proteins in $E.$ $coli$ strain BL21. Typically, a 2-liter culture was grown to $OD_{600} \sim 0.6$ at 30° C. and induced with 0.3 mM IPTG at room temperature for 6 hours.

Purification and thrombin cleavage of the fusion proteins were performed according to standard procedures (manual from Pharmacia). After removal of free GST, the samples containing FKBP12 or FRAP12 were concentrated to ~10 mL in a 50 mL stir-cell ultraconcentrator (Amicon) with a 3-kDa cutoff filter, and fractionated on a Sephacryl S-100 column (2.5 cm×85 cm) equilibrated in 10 mM phosphate buffer (pH 7.4) containing 136 mM NaCl, 3 mM KCl, 1 mM DTT. Fractions containing pure FKBP12 or FRAP12 (>95% purity judged by SDS-PAGE) were combined and concentrated to ~10 mg/mL using a stir-cell ultraconcentrator. The concentrated samples were stored in the same phosphate buffer at 4° C.

II. Crystallization & Structure Determination

Crystallization

Recombinant human FKBP12 purified from *E. coli* was used at 10 mg/mL in 10 mM tris-HCl pH 8.0. Rapamycin was dissolved in methanol and mixed with FKBP12 in a 2:1 molar ratio. The mixture was lightly vortexed and stored overnight at 4° C. to insure complete complex formation. Purified 12-kDa FRB domain of FRAP at 10 mg/mL in 50 mM tris-HCl pH 8.0 was added to this mixture in a 1:1 (FKBP12-rapamycin complex:FRB domain) molar ratio. This mixture was also lightly vortexed and let sit overnight at 4° C. to insure complete complex formation. Crystallization conditions were screened using the hanging drop method, and rectangular rod-shaped crystals were obtained using: 20% PEG 8000, 10% MPD and 10 mM tris-HCl at pH 8.5. For the hanging drop method, drops of 4 $\mu$L containing 2 $\mu$L of complex solution and 2 $\mu$L of reservoir solution were equilibrated against 0.5 mL of the reservoir solution. Microseeding techniques were used to prepare additional crystals. The initial crystals were crushed and diluted to prepare a seed solution that was added to newly prepared drops. After two weeks, a shower of tiny crystals was obtained. Macroseeding techniques were then applied to get large crystals suitable for X-ray diffraction. A tiny but well-formed crystal was picked and used as a crystallization seed. After two to three weeks, rectangular rod-shaped crystals with a maximum size of 0.3×0.2×0.1 mm$^3$ were obtained, and these crystals were suitable for data collection. The Hg-derivative crystal was obtained by soaking the native crystal in 2 mM HgCl$_2$ solution overnight. All of the crystallization experiments were done at 4° C.

Data Collection

All data sets were collected at room temperature on a San Diego multiwire area detector system mounted on a Rigaku RU-200 rotating anode X-ray source operating at 50 kV and 150 mA. The detector was positioned at a 20-value of −30° with a 544 mm detector-crystal distance for the high resolution data and 12° with a 506 mm detector-crystal distance for the low resolution data. The data collection was performed using an ω-scan with an increment of 0.10° for each frame and 40 second exposure time per frame. Crystals belong to the orthorhombic space group P2$_1$2$_1$2$_1$ with unit-cell dimension of a=44.63, b=52.14, c=102.53 Å and one FKBP12-rapamycin-FRB complex in the asymmetric unit. Hg-derivative crystal data were collected under the same conditions. For the native data set, the measured intensity data were processed using SCALEPACK (Otwinski et al, 1992) giving 6920 unique reflections out of 43447 measured reflections to 2.7 Å resolution (98.5% data coverage) with Rsym of 7.1%. For the Hg-derivative data set, the number of unique reflection was 6884 out of 42681 measured reflections to 2.7 Å (98.0% data coverage), with R$_{sym}$ of 7.1%.

Structure determination

The crystal structure of the ternary complex was solved using the molecular replacement (MR) method combined with the single isomorphous replacement with anomalous scattering (SIRAS) method. Initial phases were obtained from the molecular replacement search using the FKBP12-rapamycin complex structure as a search model. The cross rotation search revealed a clear peak at $\Theta_1$=10.8°, $\Theta_2$=70.0°, $\Theta_3$=309.4° with height/r.m.s. ratio of 12.9 and the translation search also showed a clear peak at x=0.000, y=0.230, z=0.417 with height/r.m.s. ratio of 10.5. Rigid body refinement resulted in an R factor of 0.449 (10–2.7 Å). All molecular replacement calculations used the X-PLOR program (Brunger, 1990). However, the resulting difference electron density map was noisy and hard to interpret. In order to improve the map quality, an Hg derivative crystal was obtained. These data were compared with the native data to give an R$_{diff}$ of 12.7%. Two heavy atom sites were found from the difference Patterson map and were refined using the program PHASES (Furey et al, 1990). One Hg is bound to Cys22 of FKBP12 with full occupancy—the same Hg site seen in the FKBP12-FK506 complex. The other heavy atom site is in the middle of FRB domain where it is bound to Cys2085 of FRAP with an occupancy factor of 0.6. Both Patterson-deduced heavy atom positions were validated in the Fo-Fc difference map using Fo of the heavy atom derivative and Fc from the molecular replacement solution. Anomalous dispersion measurements were included in this data set and 16 cycles of a solvent flattening procedure were applied, resulting in a phasing power of 2.76 and mean figure of merit of 0.840. All of these calculations were performed using the program PHASES. The electron density map was calculated using the combined phase from the SIRAS and the molecular replacement solution, which dearly showed four helix bundle architecture of FRB domain of FRAP.

Model Building and refinement

The FKBP12-rapamycin part was well defined in the initial electron density map; only minor changes in the backbone of 30 s loop and some side chains were enough to fit the model of FKBP12-rapamycin structure to this electron density map. For the FRB domain part, most of a polyalanine chain could be traced for the helix regions in the initial map. After several cycles of the positional refinement using X-PLOR, loop regions could be traced and the amino acid sequence could be assigned. The program CHAN (Sack, 1988) was used for the model fitting and building the ternary complex. A total of 95 residues were built for the FRB domain of FRAP; three residues in the N-terminal and two residues in the C-terminal of FRB domain had no electron density and were not included. Positional refinement was followed by simulated annealing (slow cooling from 3000K to 300K in 25 K steps, 0.0005 ps per step and 50 total steps were used in the simulation at each temperature) and restrained B-factor refinement. All refinements were done using the X-PLOR package. Solvent molecules were assigned during the iterative positional and B-factor refinement procedure, if they appeared at the 3.5 σ level of Fo-Fc map, showed good hydrogen bonding geometry and had a low B-factor (less than 50 Å$^2$). The current structure includes 202 amino acids (107 for FKBP12 and 95 for FRB domain), one rapamycin, and 23 water molecules. The final R factor is 19.3% with an R$_{free}$ of 29.9%. The free R-factor is calculated with 10% of the data that were selected at the beginning of the analysis. Crystallographic statistics are summarized in Table 2.

Quality of the coordinates

The final coordinates have good geometry and r.m.s. deviations from the ideality are 0.008 Å for bond lengths and 1.5° for bond angles. Examined by the program PROCHECK (Laskowski, 1993), the current 2.7 Å resolution structure shows that the main-chain and side-chain geometrical parameters are better than expected at this resolution with an overall G-factor of 0.0. Ramachandran plots of φ, ψ, angles showed that 86% of the nonglycine and nonproline residues are in energetically most favored regions. The average temperature factors for total atoms and main-chain atoms are 17.0 and 14.7 Å² respectively. The r.m.s. variation in the B-factor of bonded atoms is 2.5 Å². The Luzzati plot (Luzzati, 1952) indicates that the average coordinate error of this complex structure is between 0.25 and 0.30 Å.

Those structural coordinates are set forth in Protein Databank format in FIG. 4, below. Such data may be transferred to any desired medium, and formatted as desired, for the practitioner's computer.

This invention encompasses those coordinates as well as any translation or rotation or the like thereof which maintains the internal coordinates, i.e., which maintains their intrinsic, internal relationship. Those skilled in the art will appreciate that the coordinates may be subjected to other transformations including, e.g. molecular mechanics calculations such as dynamic simulation, minimization, etc. This invention further encompasses the use of coordinates of the FRB of FRAP, of the ternary complex, or of the corresponding region of FRAP homologs, and in particular, the coordinates set forth in FIG. 4, in conducting such transformations (or more extensive transformations such as the generation of alternative conformations), as well as the products of such transformations (i.e., derivatives of the coordinates).

TABLE 2

Crystallographic statistics of the ternary complex FKBP12-rapamycin-FKB domain of FRAP

| | | Data collection statistics | | | |
|---|---|---|---|---|---|
| Data Set | Resolution (Å) | No. of Reflections | | Data coverage(%) | $R_{sym}(\%)$* |
| | | Measured | Unique | | |
| Native | 2.7 | 43447 | 6920 | 98.5 | 7.1 |
| $HgCl_2$ | 2.7 | 42681 | 6884 | 98.0 | 7.1 |

| Molecular replacement results | | | | |
|---|---|---|---|---|
| Rotation function | $\Theta_1 = 10.82°$ | $\Theta_2 = 70.00°$ | $\Theta_2 = 309.35°$ | Height/r.m.s. = 12.9σ |
| Translation function | x = 0.000 | y = 0.230 | z = 0.417 | Height/r.m.s. = 10.5σ |

| Heavy atom data statistics (SIRAS) | | | |
|---|---|---|---|
| Sites | $R_{diff}(\%)$† | Phasing power+800 | Mean figure-of-merit |
| 2 | 12.7 | 2.76 | 0.840 |

| Refinement statistics | | | | | |
|---|---|---|---|---|---|
| | | | | R.M.S. deviation | |
| Resolution (Å) | Reflections (with \|F\| > 3σ) | Number of atoms | R-factor (%) | $R_{free}$ (%) | Bond lengths (Å) | Bond angles (°) |
| 8–2.7 | 6206 | 1727 | 19.3 | 29.9 | 0.008 | 1.48 |

*$R_{sym} = \Sigma|I - <I>|/\Sigma I$, where I is the observed intensity and <I> is the average intensity from multiple measurement.
†$R_{diff} = \Sigma|F_{PH} - F_p|/\Sigma F_{PH}$, where $F_p$ and $F_{PH}$ are the amplitudes of native and derivative structure factors, respectively.
+800 Phasing power = r.m.s. ($F_H/\epsilon$), where $F_H$ is heavy-atom structure factor amplitude and $\epsilon$ is residual lack of closure error.

III. Assays

Compounds which bind to the FRB of FRAP may be evaluated using materials and methods useful for testing the biological or pharmacological activity of rapamycin analogs. See e.g. Luengo et al, 1995. In addition, the following animal models may be used for further evaluation of such compounds:

(a) DELAYED TYPE HYPERSENSITIVITY

Mouse abdomens are painted with sensitizing chemicals (sensitization) such as dinitroflourobenzene or oxazalone. Seven days later the ears of sensitized mice are painted (challenge) with a lower concentration of the compound. Antigen processing and presentation, T lymphocyte activation, leukocyte infiltration, humoral mediator release, increased microvascular permeability, and plasma exudation all result from challenge of sensitized mice and lead to edema formation. Edema presents as a two- to three- fold increase in ear thickness within twenty-four hours.

The test compounds or standards can be applied (topical or parenteral) at various times before or after the sensitization or challenge phases. Increased ear thickness is prevented by several compounds including immunosuppressive agents and steroids. This model is a primary model for contact dermatitis.

(b) ALLOGENEIC SKIN TRANSPLANTATION

An allogeneic skin transplant model is used to identify immunosuppressive activity of test compounds. In this model, donor mouse thoracic skin (Balb/c) is surgically grafted onto the thorax of recipient mice (C57bl/6). Host rejection of the graft is evidenced by erythema, drying out, and retraction of donor skin. The mean graft survival time is 10 to 11 days, with 80% of the grafts being rejected by 12 days. Active novel immunosuppressive compounds, like existing immunosuppressive compounds, will prolong graft survival.

(c) POPLITEAL LYMPH NODE HYPERPLASIA

This model directly assesses T lymphocyte proliferation in vivo. Spleen cells, obtained from Balb/c mice, are isolated and administered into the foot pads of C3H mice. Within four days, the popliteal lymph nodes can be removed from the recipient mice and weighed. Other hematological assessments including FACS scanning for T lymphocyte subpopulations may also be performed. Active compounds, like existing immunosuppressive compounds, will inhibit the increase in node mass.

(d) RHEUMATOID ARTHRITIS

Several models are available for assessment of anti-arthritic activity, including adjuvant-induced, carageenan-induced, and collagen-induced arthritis in rats and/or mice. Paw pads are injected with one of these agents. Paws increase in volume, and measurements are made between 20 and 30 days later. The ability of test compounds to prevent the induction of paw swelling is tested with daily treatment for 12 consecutive days following the injection of inducing agent. The ability for the test compounds to reverse the progression of the paw swelling is tested by administration of the compound for 12 consecutive days beginning on the twelfth day following the injection of inducing agent. Paw swelling measurements are made by water displacement plethysmography. Histology is also an appropriate endpoint for these studies. The MRL/lpr-mouse model, described above, is required for the rheumatoid arthritis indication. This model is a spontaneous autoimmune model that develops rheumatoid arthritis resembling the human condition, including the presence of circulating rheumatoid factor, pannus formation, and bone and cartilage erosion.

(e) SYSTEMIC LUPUS ERYTHEMATOSUS

Systemic lupus erythematosus is another autoimmune disease with several animal models. Several murine strains develop spontaneous SLE. One such strain is MRL/lpr-mice. These mice, over time (20 to 30 weeks) develop autoantibodies against dsDNA, nuclear antigens, and renal basement membrane. This leads to complement fixation and immune complex formation. Damage to the kidney becomes apparent with the onset of proteinuria. Many of the other physiologic, hematologic, and immunologic aberrations described below for the CGVHD model are present. Immunosuppressive compounds such as cyclosporin, cyclophosphamide, and leflunomide can prevent and reverse the course of disease in this model. Interestingly, these mice also develop pathologies akin to rheumatoid arthritis.

The murine chronic graft versus host disease model (CGVHD, described below) is a model of SLE that contains many of the clinical features of SLE. Activity in this model has been shown to be predictive of activity in the more clinically relevant SLE models.

(f) TRANSPLANTATION

Allograft transplantation (skin graft) assay is often used as an initial test of immunosuppressive activity. While this model is useful as a screen, it may be supplemented with assays based on animal transplant models involving transplantation of internal organ (heart, liver, kidney, bone marrow) with use of "clinically acceptable" physiologic endpoints to assess graft survival. Efficacy of test compounds in only a very limited number of these rodent models is required. Following observation of activity in a rodent model, the test compounds are typically tested in further animal models (e.g., canine, porcine or non-human primate). Active compounds decrease acute and chronic rejection and prolong transplant survival.

(g) GRAF VS. HOST DISEASE

Chronic GVHD (CGVHD) can be used to model $CD4^+$-dependent humoral immunity. It is induced in BDF1 mice (which are progeny of DBA/2 male×C57BL/6 female matings) by administering to them isolated spleen:lymph node cells from DBA/2 mice. This results in: a) disregulation and stimulation of $CD4^+T$ lymphocyte ($Ly1^+$; murine marker) activity due to incompatibilities at MHC II molecules, and b) abnormal T-B lymphocyte cooperation. The resulting pathological state, in many ways, mimics systemic lupus erythematosus (SLE). Several measurable endpoints develop within 14 days; including, circulating anti-host IgG and IgE antibodies, altered T and B lymphocyte proliferation activity measured in vitro, complement utilization, hemagglutination, slow progressive wasting, dermal aberrations, splenomegaly, lymphoid hyperplasia, and proteinuria. Only a few of these endpoints need to be measured. Active compounds are are those which limit T lymphocyte disregulation and abrogate changes in these variables. Many steroids (e.g., prednisolone), cyclosporine, FK-506, cyclophosphamide, and leflunomide are all active in this model and can be used as positive controls.

The acute GVHD model (AGVHD) is also produced in $BDF_1$ mice. In this case, isolated spleen:lymph node cells from C57BL/6 mice are administered. This results in disregulation and stimulation of $CD8^+T$ lymphocytes due to incompatibilities in the MHC I molecules. Elevated cytokine levels and donor clonal expansion occurs. Ultimately, donor cytotoxic T lymphocytes and NK cells rapidly reject host tissue and cause relatively rapid death of the recipient. The progression of AGVHD in this model is assessed by measurement of hematologic abnormalities (including T cell number and type), cytokine elevations (TNF, IL-1, IL-2, and/or IL-4), low body weight, hypoyglobulinemia, circulating hematologic characteristics indicative of aplastic anemia (granulocytopenia, thrombocytopenia), ex vivo NK or CTL activity, and host survival. Active compounds are those which abrogate changes in the variables, and prolong survival over 4 to 6 weeks.

(h) ASTHMA

Asthma offers another opportunity for safe immunosuppressive therapy. Atopic asthmatics have antibody mediated hypersensitivity and the often occurring late phase reaction is likened to a DTH response. Asthma has only recently been defined as an inflammatory disease (1992). Since then, several publications from prominent asthmatologists demonstrate the presence of activated $CD4^+$ and $CD8^+T$ lymphocytes in bronchoalveolar lavage fluid and blood of atopic asthmatics. The ratios of these cells changes in asthmatic conditions. Furthermore, several of the T cell associated cytokines (IL-1, IL-2, IL-4, IL-5, and TNF) are all implicated in clinical and experimental asthma. Inflammatory events in asthma are now considered to be T lymphocyte driven. Initial clinical trials with inhaled cyclosporin suggest that local immunosuppression can ameliorate airway hyperreactivity—the underlying defect in asthma.

The guinea pig model of antigen-induced pulmonary aberrations is used as a model for asthma. These animals are actively sensitized to ovalbumin to generate high circulating titers of anti-ovalbumin antibody with seroconversion to the IgE class, as is the case with atopic asthmatics. Aerosol challenge of sensitized guinea pigs results in measurable eosinophil rich pulmonary infiltrates (approximately a 16-fold increase in eosinophils), pulmonary edema, and mucous plugging of the small airways; all culminating in the expression of the underlying defect in asthma- airway hyperreactivity (approximately a 3 to 4-fold increase in reactivity). Acute bronchoconstriction is obviously present and points the aforementioned presence of the pathophysiologic sequelae. Active compounds are those which lessen or abrogate such symptoms.

The above description is meant to illustrate, rather than limit the scope of the invention. Given the foregoing description, numerous variations in the materials or methods employed in performing the invention will be obvious to one skilled in the art. Any such obvious variation is to be considered within the scope of the invention. Full references to literature cited above (by reference to author and year) are provided below:

References

Brown, E. J., Albers, M. W., Shin, T. B., Ichickawa, K., Keith, C. T., Lane, W. S. & Schreiber, S. L. Nature 369, 756–758 (1994).

Brunger, A. T. *X-PLOR Version* 3.1 *Manual* (Yale Univ. Press, New Haven, Conn., 1992)

Chen, J., Zheng, X.-F., Brown, E. J. & Schreiber, S. L. Proc. Natl. Acad. Sci. USA 92, 4947–4951 (1995).

Chiu, M. I., Katz, H & Berlin, V. Proc. Natl. Acad. Sci. USA 91, 12574–12578 (1994).

Clardy, J. . Proc. Natl. Acad. Sci. USA 92, 56–61 (1995).

Dayhoff, M. O.; Schwartz, R. M.; Orcutt, B. C., Atlas of Protein Sequence and Structure, 5, Suppl. 3,345 (1979)

Furey, W. and Swaminathan, S. *American Crystallographic Association Mtg. Abstr. Ser.* 2 18, 73 (1990)

Gonnet, G. H., Cohen, M. A., Benner, S. A. Science, 256, 1443 (1992)

Greer, J., J. Mol. Biol., 153, 1027 (1981)

Griffith, J. P., Kim, J. L., Kim, E. E., Sintchak, M. D., Thomson, J. A., Fitzgibbon, M. J., Fleming, M. A., Caron, P. R., Hsiao, K. & Navia, M. A. Cell 82, 507–522 (1995).

Harris, N. L., Presnell, S. R., and Cohen, F. E. *J. Mol. Biol.* 236, 1356–1368 (1994)

Keith & Schreiber, 1995, Science 270:50–51.

Laskowski, R. A. J. *Appl. Cryst.* 26, 283–291 (1993)

Luengo, J. I., Yamashita, D. S., Dunnington, D., Konialian Beck, A., Rozamus, L. W., Yen, H., Bossard, M. J., Levy, M. A., Hand, A., Newman-Tarr, T., Badger, A., Faucette, L., Johnson, R. K., D'Alessio, K., Porter, T., Shu, A. Y., Heys, R., Choi, J., Kongsaeree, P., Clardy, J., and Holt, D. A. *Chemistry & Biology* 2, 471–481 (1995).

Luzzati, P. V. *Acta Cryst.* 5, 802–810 (1952)

Otwinski, Z. *The SCALEPACK Manual* (Howard Hughes Medical Institute, Yale Univ., New Haven, Conn., 1992).

Sabatini, D. M., Erdjument-Bromage, H., Lui, M., Tempst, P. & Snyder, S. H. Cell 78, 35–43 (1994).

Sack, J. S. *J. Mol. Graphics* 6, 224–225 (1988)

Schreiber, S. L. Cell 70, 365–368 (1992).

Sehgal, S. N., Baker, H. & Vezina, C. J. Antibiot. 6, 727–732 (1975).

Sehgal, S. N. Ann. N.Y. Acad. Sci. 696, 1–8 (1993).

Stan, R., McLaughlin, M. M., Cafferkey, R., Johnson, R. K., Rosenberg, M., and Livi, G. P. *J. Biol. Chem.* 269, 32027–32030 (1994)

Standaert, R. F., Galat, A., Verdine, G. L. & Schreiber, S. L. *Nature* 346, 671–674 (1990)

Tanaka, H., Kuroda, A., Marusawa, H., Hatanaka, H., Kino, T., Goto, T. & Hashimoto, M. J. Amer. Chem. Soc. 109, 5031–5033 (1987).

VanDuyne, G. D., Standaert, R. F., Schreiber, S. L. & Clardy, J. Science 251, 839–842 (1991).

VanDuyne, G. D., Standaert, R. F., Schreiber, S. L. & Clardy, J. J. Am. Chem. Soc. 113, 7433–7434 (1991a).

Van Duyne, G. D., Standaert, R. F., Karplus, A., Schreiber, S. L. & Clardy, J. J. Mol. Biol. 229, 105–124 (1993).

Vezina, C., Kudelski, A. & Sehgal, S. N. J. Antibiot. 28, 721–726 (1975).

Zakian, V. A. Cell 82, 685–687 (1995)

---

We claim:

1. An orthorhombic crystalline composition in the space group P2₁2₁2₁ which diffracts X-rays at a resolution of 2.7 Å or better, each asymmetric unit of which containing one complex comprising:

(a) a first protein comprising a peptide sequence derived or selected from the peptide sequence of human FK506 binding protein 12 (FKBP12), (b) a second protein comprising a peptide sequence derived or selected from the peptide sequence of an FKBP:rapamycin binding domain of human FKBP:Rapamycin Associated Protein (FRAP), and (c) rapamycin or a rapamycin derivative capable of forming a ternary complex with the first and second proteins.

2. The crystalline composition of claim 1, wherein the first protein comprises the peptide sequence of SEQ ID No. 1 and the second protein comprises the peptide sequence of SEQ ID No. 2.

3. The composition of any of claims 1 or 2 in which the proteins of the complex are characterized by the coordinates of FIG. 4, or by coordinates having a root mean square deviation therefrom, with respect to conserved backbone atoms of the listed amino acids, of not more than 1.5 Å.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 107 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
                100                 105
```

(2) INFORMATION FOR SEQ ID NO:2:

(i) SEQUENCE CHARACTERISTICS:
      (A) LENGTH: 100 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Glu Leu Ile Arg Val Ala Ile Leu Trp His Glu Met Trp His Glu Gly
1               5                   10                  15

Leu Glu Glu Ala Ser Arg Leu Tyr Phe Gly Glu Arg Asn Val Lys Gly
            20                  25                  30
```

```
Met Phe Glu Val Leu Glu Pro Leu His Ala Met Met Glu Arg Gly Pro
        35              40                  45

Gln Thr Leu Lys Glu Thr Ser Phe Asn Gln Ala Tyr Gly Arg Asp Leu
        50              55                  60

Met Glu Ala Gln Glu Trp Cys Arg Lys Tyr Met Lys Ser Gly Asn Val
65                  70              75                      80

Lys Asp Leu Thr Gln Ala Trp Asp Leu Tyr Tyr His Val Phe Arg Arg
                85              90                  95

Ile Ser Lys Gln
            100
```